(12) United States Patent
Krieg et al.

(10) Patent No.: US 7,935,675 B1
(45) Date of Patent: *May 3, 2011

(54) IMMUNOSTIMULATORY NUCLEIC ACID MOLECULES

(75) Inventors: Arthur M. Krieg, Iowa City, IA (US); Joel N. Kline, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 878 days.

This patent is subject to a terminal disclaimer.

(21) Appl. No.: 09/337,584

(22) Filed: Jun. 21, 1999

Related U.S. Application Data

(60) Division of application No. 08/960,774, filed on Oct. 30, 1997, now Pat. No. 6,239,116, which is a continuation-in-part of application No. 08/738,652, filed on Oct. 30, 1996, now Pat. No. 6,207,646, which is a continuation-in-part of application No. 08/386,063, filed on Feb. 7, 1995, now Pat. No. 6,194,388, which is a continuation-in-part of application No. 08/276,358, filed on Jul. 15, 1994, now abandoned.

(51) Int. Cl.
*A61K 31/70* (2006.01)
*A61K 48/00* (2006.01)
*A61K 39/00* (2006.01)
*A61K 39/38* (2006.01)
*A01N 43/04* (2006.01)
*C07H 21/02* (2006.01)

(52) U.S. Cl. .................. 514/44 R; 536/23.1; 424/184.1
(58) Field of Classification Search .................. 514/44, 514/2; 536/23.1, 24.1
See application file for complete search history.

(56) References Cited

U.S. PATENT DOCUMENTS

| | | | |
|---|---|---|---|
| 3,906,092 A | 9/1975 | Hilleman et al. | 424/209.1 |
| 5,023,243 A | 6/1991 | Tullis | |
| 5,248,670 A | 9/1993 | Draper et al. | 514/44 |
| 5,284,656 A | 2/1994 | Platz et al. | |
| 5,451,569 A | 9/1995 | Wong et al. | |
| 5,498,410 A | 3/1996 | Gleich | |
| 5,585,479 A | 12/1996 | Hoke et al. | 536/24.5 |
| 5,663,153 A | 9/1997 | Hutcherson et al. | |
| 5,681,555 A | 10/1997 | Gleich | |
| 5,723,335 A | 3/1998 | Hutcherson et al. | |
| 5,726,160 A | 3/1998 | McMichael | |
| 5,780,448 A | 7/1998 | Davis | |
| 5,786,189 A | 7/1998 | Locht et al. | 435/172.3 |
| 5,804,566 A | 9/1998 | Carson et al. | 514/44 |
| 5,830,877 A | 11/1998 | Carson et al. | |
| 5,849,719 A | 12/1998 | Carson et al. | 514/44 |
| 5,955,442 A | 9/1999 | McMichael | |
| 5,985,847 A | 11/1999 | Carson et al. | |
| 6,086,898 A | 7/2000 | DeKruyff et al. | |
| 6,096,721 A | 8/2000 | McMichael | |
| 6,100,244 A | 8/2000 | McMichael | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,221,882 B1 | 4/2001 | Macfarlane | |
| 6,225,292 B1 | 5/2001 | Raz et al. | |
| 6,239,116 B1 | 5/2001 | Krieg et al. | |
| 6,339,068 B1 | 1/2002 | Krieg et al. | |
| 6,399,630 B1 | 6/2002 | Macfarlane | |
| 6,406,705 B1 | 6/2002 | Davis et al. | |
| 6,426,336 B1 | 7/2002 | Carson et al. | |
| 6,429,199 B1 | 8/2002 | Krieg et al. | |
| 6,479,504 B1 | 11/2002 | Macfarlane et al. | |
| 6,498,148 B1 | 12/2002 | Raz | |
| 6,514,948 B1 | 2/2003 | Raz et al. | |
| 6,521,637 B2 | 2/2003 | Macfarlane | |
| 6,534,062 B2 | 3/2003 | Raz et al. | |
| 6,552,006 B2 | 4/2003 | Raz et al. | |
| 6,558,670 B1 | 5/2003 | Friede et al. | |
| 6,562,798 B1 | 5/2003 | Schwartz | |
| 6,589,940 B1 | 7/2003 | Raz et al. | |
| 6,610,308 B1 | 8/2003 | Haensler | |
| 6,610,661 B1 | 8/2003 | Carson et al. | |
| 6,653,292 B1 | 11/2003 | Krieg et al. | |
| 6,727,230 B1 | 4/2004 | Hutcherson et al. | |
| 6,787,524 B2 | 9/2004 | Chang et al. | |
| 6,797,276 B1 * | 9/2004 | Glenn et al. | 424/278.1 |
| 6,815,429 B2 * | 11/2004 | Agrawal | 514/44 |
| 6,821,957 B2 * | 11/2004 | Krieg et al. | 514/44 |
| 6,843,992 B2 * | 1/2005 | Diamond | 424/186.1 |
| 6,887,464 B1 * | 5/2005 | Coleman et al. | 424/93.21 |
| 6,936,261 B2 * | 8/2005 | Granoff et al. | 424/249.1 |
| 6,943,240 B2 * | 9/2005 | Bauer et al. | 536/23.1 |
| 6,949,520 B1 * | 9/2005 | Hartmann et al. | 514/44 |

(Continued)

FOREIGN PATENT DOCUMENTS

EP     0 468 520 A2     1/1992

(Continued)

OTHER PUBLICATIONS

Berg et al, J. Clin Invest. 96: 2339 (1995).*
Blanchard et al, J. Immunol. 136: 963 (1986).*
D'Andrea et al, J. Exp. Med. 178: 1041 (1993).*
Schwartz et al, Am. J. Physiol. 267 (5 Pt 1), L609 (1994).*
Schwartz et al, Am. J. Respir. Crit. Care Med. 152: 603 (1995).*
Wohlleben et al, Trends in Immunology, Nov. 2001, 22/11:618-626.*
Kline et al, J. Immunology, 1998, 160:2555-2559.*
Lewis, Current Opinion in Immunology, 2002, 14:644-651.*
Chisholm et al, J. Allergy Clin. Immunology, 2004, 113:448-454.*

(Continued)

*Primary Examiner* — N. M Minnifield
(74) *Attorney, Agent, or Firm* — Wolf, Greenfield & Sacks, P.C.; Gregg C. Benson

(57) ABSTRACT

Nucleic acid sequences containing unmethylated CpG dinucleotides that modulate an immune response including stimulating a Th1 pattern of immune activation, cytokine production, NK lytic activity, and B cell proliferation are disclosed. The sequences are also useful a synthetic adjuvant.

25 Claims, 19 Drawing Sheets

U.S. PATENT DOCUMENTS

| | | |
|---|---|---|
| 6,951,845 B2 | 10/2005 | Carson et al. |
| 6,977,245 B2 | 12/2005 | Klinman et al. |
| 6,994,870 B2 | 2/2006 | Tsai |
| 7,001,890 B1 | 2/2006 | Wagner et al. |
| 7,034,007 B1 | 4/2006 | Nyce et al. |
| 7,129,222 B2 | 10/2006 | Van Nest et al. |
| 7,208,478 B2 | 4/2007 | Carson et al. |
| 7,223,398 B1 | 5/2007 | Tusk et al. |
| 7,223,741 B2 | 5/2007 | Krieg |
| 7,271,156 B2 | 9/2007 | Krieg et al. |
| 7,306,782 B2 | 12/2007 | Borel et al. |
| 7,354,711 B2 | 4/2008 | Macfarlane |
| 7,402,572 B2 | 7/2008 | Krieg et al. |
| 7,410,975 B2 | 8/2008 | Lipford et al. |
| 7,488,490 B2 * | 2/2009 | Davis et al. ............... 424/278.1 |
| 7,514,414 B2 | 4/2009 | Klinman et al. |
| 7,514,415 B2 | 4/2009 | Klinman et al. |
| 7,517,861 B2 | 4/2009 | Krieg et al. |
| 7,521,063 B2 | 4/2009 | Klinman et al. |
| 7,524,828 B2 | 4/2009 | Krieg et al. |
| 7,534,772 B2 | 5/2009 | Weiner et al. |
| 7,541,040 B2 | 6/2009 | Puri et al. |
| 7,566,703 B2 | 7/2009 | Krieg et al. |
| 7,569,553 B2 | 8/2009 | Kreig |
| 7,576,066 B2 | 8/2009 | Krieg |
| 7,585,847 B2 | 9/2009 | Bratzler et al. |
| 7,605,138 B2 | 10/2009 | Krieg |
| 7,605,738 B2 | 10/2009 | Kuramochi et al. |
| 7,615,227 B2 | 11/2009 | Klinman et al. |
| 7,615,539 B2 | 11/2009 | Krieg et al. |
| 7,674,777 B2 | 3/2010 | Krieg et al. |
| 7,713,529 B2 | 5/2010 | Krieg et al. |
| 7,723,022 B2 * | 5/2010 | Krieg et al. ........................ 435/5 |
| 7,723,500 B2 * | 5/2010 | Krieg et al. ................. 536/23.1 |
| 2001/0044416 A1 | 11/2001 | McCluskie et al. |
| 2001/0046967 A1 | 11/2001 | Van Nest et al. |
| 2002/0028784 A1 | 3/2002 | Van Nest et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0086839 A1 | 7/2002 | Raz et al. |
| 2002/0091097 A1 | 7/2002 | Bratzler et al. |
| 2002/0098199 A1 | 7/2002 | Van Nest et al. |
| 2002/0102255 A1 | 8/2002 | Chang |
| 2002/0107212 A1 | 8/2002 | Van Nest et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0022852 A1 | 1/2003 | Van Nest et al. |
| 2003/0026801 A1 | 2/2003 | Weiner et al. |
| 2003/0027782 A1 | 2/2003 | Carson et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0059773 A1 | 3/2003 | Van Nest et al. |
| 2003/0064064 A1 | 4/2003 | Dina et al. |
| 2003/0078223 A1 | 4/2003 | Raz et al. |
| 2003/0087848 A1 | 5/2003 | Bratzler et al. |
| 2003/0091599 A1 | 5/2003 | Davis et al. |
| 2003/0092663 A1 | 5/2003 | Raz et al. |
| 2003/0100527 A1 | 5/2003 | Krieg et al. |
| 2003/0104523 A1 | 6/2003 | Bauer et al. |
| 2003/0109469 A1 | 6/2003 | Carson et al. |
| 2003/0119773 A1 | 6/2003 | Raz et al. |
| 2003/0125284 A1 | 7/2003 | Raz et al. |
| 2003/0129251 A1 | 7/2003 | Van Nest et al. |
| 2003/0130217 A1 | 7/2003 | Raz et al. |
| 2003/0133988 A1 | 7/2003 | Fearon et al. |
| 2003/0139364 A1 | 7/2003 | Krieg et al. |
| 2003/0143213 A1 | 7/2003 | Raz et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0181406 A1 | 9/2003 | Schetter et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0203861 A1 | 10/2003 | Carson et al. |
| 2003/0212028 A1 | 11/2003 | Raz et al. |
| 2003/0216340 A1 | 11/2003 | Van Nest et al. |
| 2003/0225016 A1 | 12/2003 | Fearon et al. |
| 2003/0232074 A1 | 12/2003 | Lipford et al. |
| 2003/0232780 A1 | 12/2003 | Carson et al. |
| 2003/0232856 A1 | 12/2003 | MacFarlane |
| 2004/0006010 A1 | 1/2004 | Carson et al. |
| 2004/0006034 A1 | 1/2004 | Raz et al. |
| 2004/0009942 A1 | 1/2004 | Van Nest et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0053880 A1 | 3/2004 | Krieg |
| 2004/0063880 A1 | 4/2004 | Chisholm et al. |
| 2004/0064064 A1 | 4/2004 | Zhou et al. |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0131628 A1 | 7/2004 | Bratzler et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0248837 A1 | 12/2004 | Raz et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0042203 A1 | 2/2005 | Davis et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Jurk et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |

| | | |
|---|---|---|
| 2005/0171047 A1 | 8/2005 | Krieg et al. |
| 2005/0175630 A1 | 8/2005 | Raz et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0209183 A1 | 9/2005 | Kippenberger et al. |
| 2005/0209184 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0261215 A1 | 11/2005 | Garren et al. |
| 2005/0267057 A1* | 12/2005 | Krieg .................. 514/44 |
| 2005/0267064 A1 | 12/2005 | Krieg et al. |
| 2005/0276756 A1 | 12/2005 | Hoo et al. |
| 2005/0277604 A1 | 12/2005 | Krieg et al. |
| 2005/0277609 A1 | 12/2005 | Krieg et al. |
| 2006/0002959 A1 | 1/2006 | Glenn et al. |
| 2006/0002962 A1 | 1/2006 | Jacobi et al. |
| 2006/0003955 A1* | 1/2006 | Krieg et al. .................. 514/44 |
| 2006/0003962 A1 | 1/2006 | Ahluwalia et al. |
| 2006/0019239 A1* | 1/2006 | Ivins et al. .................. 435/5 |
| 2006/0019909 A1 | 1/2006 | Agrawal et al. |
| 2006/0019916 A1* | 1/2006 | Krieg et al. .................. 514/44 |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0171968 A1 | 8/2006 | Brimnes et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2007/0243209 A1 | 10/2007 | Segal et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2008/0260751 A1 | 10/2008 | Karp et al. |
| 2009/0017021 A1 | 1/2009 | Davis et al. |
| 2009/0060927 A1 | 3/2009 | Wagner et al. |
| 2009/0117132 A1 | 5/2009 | Readett et al. |
| 2009/0137519 A1 | 5/2009 | Krieg et al. |
| 2009/0142362 A1 | 6/2009 | Krieg et al. |
| 2009/0155212 A1 | 6/2009 | Bratzler et al. |
| 2009/0155307 A1 | 6/2009 | Davis et al. |
| 2009/0191188 A1 | 7/2009 | Krieg et al. |
| 2009/0202575 A1 | 8/2009 | Krieg et al. |
| 2009/0214578 A1 | 8/2009 | Bauer |
| 2009/0306177 A1 | 12/2009 | Uhlmann et al. |
| 2009/0311277 A1 | 12/2009 | Krieg |
| 2010/0104507 A1* | 4/2010 | Klinman et al. .................. 424/1.21 |
| 2010/0130593 A1* | 5/2010 | Garren et al. .................. 514/44 R |
| 2010/0183639 A1* | 7/2010 | Uhlmann et al. .................. 424/184.1 |

FOREIGN PATENT DOCUMENTS

| | | |
|---|---|---|
| EP | 0468520 A3 | 1/1992 |
| EP | 0302758 B1 | 3/1994 |
| EP | 0 766571 B1 * | 12/2001 |
| EP | 1 671 646 A2 | 6/2006 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO 96/02555 A1 | 2/1996 |
| WO | WO 96/32138 A1 * | 10/1996 |
| WO | WO 96/35782 | 11/1996 |
| WO | WO 96/40162 A1 | 12/1996 |
| WO | WO 97/28259 | 8/1997 |
| WO | WO 97/28259 A1 | 8/1997 |
| WO | WO 98/14210 | 4/1998 |
| WO | WO 98/16247 A1 | 4/1998 |
| WO | WO 98/18810 | 5/1998 |
| WO | WO 98/32462 A1 | 7/1998 |
| WO | WO 98/37919 | 9/1998 |
| WO | WO 98/40100 | 9/1998 |
| WO | WO 98/49288 A1 | 11/1998 |
| WO | WO 98/52581 | 11/1998 |
| WO | WO 98/55495 A2 | 12/1998 |
| WO | WO 98/55609 A1 | 12/1998 |
| WO | WO99/11275 A2 | 3/1999 |
| WO | WO 99/56755 A1 | 11/1999 |
| WO | WO 99/58118 A2 | 11/1999 |
| WO | WO 00/06588 A1 | 2/2000 |
| WO | WO 00/14217 A2 | 3/2000 |
| WO | WO 00/15256 A2 | 3/2000 |
| WO | WO 00/54803 A2 | 9/2000 |
| WO | WO 00/61151 A2 | 10/2000 |
| WO | WO 00/67023 A1 | 11/2000 |
| WO | WO 01/22990 A2 | 4/2001 |
| WO | WO 01/35991 A2 | 5/2001 |
| WO | WO 01/45750 A1 | 6/2001 |
| WO | WO 01/68116 A2 | 9/2001 |
| WO | WO 02/28428 A2 | 4/2002 |
| WO | WO 02/069369 A2 | 9/2002 |
| WO | WO 03/043572 A2 | 5/2003 |
| WO | WO 2004/007743 A2 | 1/2004 |
| WO | WO 2004/026888 A2 | 4/2004 |
| WO | WO 2004/041183 A2 | 5/2004 |
| WO | WO 2004/094671 A2 | 11/2004 |
| WO | WO 2006/080946 A2 | 8/2006 |
| WO | WO 2006/091591 A1 | 8/2006 |
| WO | WO 2006/096497 A2 | 9/2006 |
| WO | WO 2007/031877 A2 | 3/2007 |
| WO | WO 2007/038720 A2 | 4/2007 |
| WO | WO 2007/095316 A2 | 8/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Agrawal et al, International Immunopharmacology, 2004, 4:127-138.*
Norman, J. Allergy Clin. Immunology, 2004, 113:1013-1023.*
Agrawal et al, Trends in Molecular Medicine, Mar. 2002, 8/3:114-121.*
Zhu et al, International Immunopharmacology, 2004, 4:851-862.*
Grunig et al, Pharmacology and Therapeutics, 2004, 22 pages Article in Press.*
Kline et al, J. Allergy Clin. Immunol., Feb. 2004, 113/2:S254, Abstract #915 Abstract only.*

Bochner et al, J. Allergy Clin. Immunol., 2004, 113:868-875.*
Chang t al, J. All rgy Clin. Immunol., 2004, 113/2:S323, Abstract # 1196 Abstract only.*
Roy et al, J. Allergy Clin. Immunol., 2003, 112:571-578.*
Verthelyi et al, Clinical Immunology, 2003, 109:64-71.*
Jain et al, Expert Opinion Biol. Ther., 2004, 4/9:1533-1540.*
Redecke et al, J. Immunology, 2004, 172:2739-2743.*
Silverman et al, Am. J. Respir. Cell Mol. Biol., 2003, 28:645-647.*
Chiang et al, Am J. Respir. Crit. Care Med., 2003, 168:575-580.*
Choudhury et al, J. Immunology, 2002, 169:5955-5961.*
Kitagaki et al, Clinical and Diagnostic Laboratory Immunology, Nov. 2002, 9/6:1260-1269.*
Creticos et al, Immunol. Allergy Clin. North Am., Nov. 2004, 24/4:569-281 Abstract Only.*
Stokes et al, Ann. Allergy Asthma Immunol., Sep. 2004, 93/3:212-217 Abstract Only.*
Metzger et al, J. Allergy Clin. Immunol., 1999, 104/2 Pt. 1:260-266 Abstract Only.*
Boushey, Allerg. Immunol., Nov. 2000, 32/9:336-341 Abstract Only.*
Kline, Curr. Opin. Allergy Clin. Immunol., 2002, 2/1:69-73 Abstract Only.*
Jain et al, J. Allergy Clin. Immunol., 2002, 110:867-872.*
Satoh et al, Fukushima Igaku Zasshi, 2002, 52/3:237-250 Abstract only.*
Dziadzio et al, Handbook of Experimental Pharmacology, 2004, 161(Pharmacology and Therapeutics of Asthma and COPD):273-285 Abstract only.*
Krieg et al, Immunology Today, 2000, 21/10:521-226.*
Weiner et al, J. Leucocyte Biology, 2000, 68:455-463.*
Agrawal et al, Molecular Med. Today, 2000, 6:72-81.*
McCluskie et al, Mol cular Med. Today, 1999, 5/5:287-300.*
McCluskie et al, Vaccine, 2001, 19:2657-2660.*
McCluskie et al, Critical Reviews in Immunology, 2001, 21:103-120.*
Barnes, European J. Internal Medicine, 2000, 11:9-20.*
Ser brisky t al, J. Immunology, 2000, 165:5906-5912.*
Jain et al, Clin. Exp. Allergy, 2003, 33:1330-1335.*
Litzinger et al, BBA, 1996, 1281:139-149.*
Singh et al, Pharmaceutical Research, 2001, 18/10:1476-1479.*
Jain et al, Recent Res. Develop. Resp. Critical Care Med., 2002, 2:7-18.*
Milligan et al, J. Medicinal Chemistry, 1993, 36/14:1923-1937.*
Alm et al, Nature, 1997, 350:400-403.*
Silverman et al, Nature, 1997, 350:380-381.*
Vandenulcke et al, Int. Arch. Allergy Immunol., 2006, 139/2:159-165, abstract only.*
Humlova, Cas. Lek. Cesk., 2004, 143/1:21-25 abstract only.*
Chisholm et al, J. Allergy Clin. Immunol., 2004, 113:448-454.*
Liu et al, J. Allergy Clin. Immunol., 2003, 111:471-478.*
Felesko et al, European J. Pharmacology, 2006, 533:308-318.*
Sander et al, Immunolgy, 1995, 86/4:512-518 abstract only.*
Racila et al, J. Allergy Clin. Immunol., 2005, 116:1202-1205.*
Bauer et al., Human TLR9 confers responsiveness to bacterial DNA via species-specific CpG motif recognition. Proc Natl Acad Sci U S A. Jul. 31, 2001;98(16):9237-42. Epub Jul. 24, 2001.
Cooper et al., CPG 7909, an immunostimulatory TLR9 agonist oligodeoxynucleotide, as adjuvant to Engerix-B HBV vaccine in healthy adults: a double-blind phase I/II study. J Clin Immunol. Nov. 2004;24(6):693-701.
Friedberg et al., Combination immunotherapy with a CpG oligonucleotide (1018 ISS) and rituximab in patients with non-Hodgkin lymphoma: increased interferon-alpha/beta-inducible gene expression, without significant toxicity. Blood. Jan. 15, 2005;105(2):489-95. Epub Sep. 9, 2004.
Hemmi et al., Toll-like receptor recognizes bacterial DNA. Nature. Dec. 7, 2000;408(6813):740-5.
Hemmi et al., The roles of Toll-like receptor 9, MyD88, and DNA-dependent protein kinase catalytic subunit in the effects of two distinct CpG DNAs on dendritic cell subsets. J Immunol. Mar. 15, 2005;170(6):3059-64.
Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.
Lukacs et al., Interleukin-4-dependent pulmonary eosinophil infiltration in a murine model of asthma. Am J Respir Cell Mol Biol. May 1994;10(5):526-32.
Lukacs et al., C-C chemokine-induced eosinophil chemotaxis during allergic airway inflammation. J Leukoc Biol. Nov. 1996;60(5):573-8.
Padrid et al., CTLA4Ig inhibits airway eosinophilia and hyper-responsiveness by regulating the development of Th1/Th2 subsets in a murine model of asthma. Am J Respir Cell Mol Biol. Apr. 1998;18(4):453-62.
Siegrist et al., Co-administration of CpG oligonucleotides enhances the late affinity maturation process of human anti-hepatitis B vaccine response. Vaccine. Dec. 16, 2004;23(5):615-22.
Chace et al, Bacterial DNA-Induced NK cell IFN-gamma production is dependent on macrophage secretion of IL-12. Clin Immunol Immunopathol. Aug. 1997;84(2):185-93.
Davis et al, "Use of CpG DNA for enhancing specific immune responses", *Current Topics in Microbiology Immunology*, 247: 171-83, 2000.
Dunn et al., The three Es of cancer immunoediting, Annu Rev Immunol. 2004;22:329-60, Review.
Durham et al., Immunotherapy and allergic inflammation. Clin Exp Allergy. Jan. 1991;21 Suppl 1:206-10.
Francois et al., Examination of the inhibitory and stimulatory effects of IFN-alpha, -beta, and -gamma on human B-cell proliferation induced by various B-cell mitogens. Clin Immunol Immunopathol. Sep. 1988;48(3):297-306.
Frissora et al., IFN-gamma-mediated inhibition of antigen receptor-induced B cell proliferation and CREB-1 binding activity requires STAT-1 transcription factor. Eur J Immunol, Apr. 2003;33(4):907-12.
Hartmann et al., "CpG DNA and LPS induce distinct patterns of activation in human monocytes", *Gene Therapy*, 6: 893-903, 1999.
Hartmann et al., "Mechanism and Function of a newly identified CpG DNA motif in human primary B cells", *Journal of Immunology*, 164:944, 2000.
Hartmann et al., "Delineation of a CpG phosphorothioate oligodeoxynucleotide for activating primate immune responses in vitro and in vivo", *Journal of Immunology*, 164: 1617, 2000.
Hartmann et al., "CpG DNA: a potent signal for growth, activation, and muturation of human dendritic cells", *Proceedings of the National Academy of Science USA*, 96: 9305-9310, 1999.
Heeg et al., CpG DNA as a Th1 trigger. Int Arch Allergy Immunol, Feb. 2000;121(2):87-97. Review.
Hopkin et al., *BioMedNet*, Issue 57, Jun. 25, 1999.
Horner et al., Optimized conjugation ratios lead to allergen immunostimulatory oligodeoxynucleotide conjugates with retained immunogenicity and minimal anaphylactogenicity. J Allergy Clin Immunol. Sep. 2002;110(3):413-20.
Horner et al., Immunostimulatory sequence oligodeoxynucleotide-based vaccination and immunomodulation: two unique but complementary strategies for the treatment of allergic diseases. J Allergy Clin Immunol. Nov. 2002;110(5):706-12. Review.
Iho et al., "Oligodeoxynucleotides containing palindrome sequences with Internal 5'-CpG-3' act directly on human NK and activated T cells to induce IFN-gamma production in vitro", *Journal of Immunology*, 163: 3642, 1999.
Ikeda et al., Chapter 23: Immunostimulatory DNA for allergic asthma. *microbial dna and Host Immunity*, 2002. p. 289-299.
Jakob et al., "Activation of cutaneous dendritic cells by CpG-containing oligodeoxynucleotides: a role for dendritic cells in the augmentation of Th1 responses by immunostimulatory DNA", *Journal of Immunology*, 161(6); 3042-9, 1998.
Jakob et al., "Bacterial DNA and CpG-containing oligodeoxynucleotides activate cutaneous dendritic cells and induce IL-12 production: implications for the augmentation of Th1 responses", *International Archives of Allergy Immunology*, 118(2-4): 457-61, 1999.
Jilek et al., Antigen-independent suppression of the allergic immune response to bee venom phospholipase A(2) by DNA vaccination in CBA/J mice. J Immunol. Mar. 1, 2001;166(5):3612-21.

Kataoka et al., "Antitumor activity of synthetic oligonucleotides with sequences from cDNA encoding proteins of Mycobacterium bovis BCG", *Japan Journal of Cancer Research*, 83: 244-247, 1992.

Kataoka et al., "Immunotherapeutic potential in guinea-pig tumor model of deoxyribonucleic acid from Mycobacterium bovis BCG complexed with poly-L-lysine and carboxymethylcellulose", *Japan Journal of Medical Science and Biology*, 43(5):171-82, 1990.

Kitagaki et al., Chapter 24: CpG oligodeoxynucleotides in asthma. *Microbial DNA and Host Immunity*. 2002. p. 301-314.

[No Author Listed] National Institute of Health, Publication No. 97-4051, Jul. 1997.

Anitescu et al., Interleukin-10 functions in vitro and in vivo to inhibit bacterial DNA-induced secretion of interleukin-12. J Interferon Cytokine Res. Dec. 1997;17(12):781-8.

Askenase et al., Gee whiz: CpG DNA allergy therapy! J Allergy Clin Immunol. Jul. 2000;106(1 Pt 1):37-40.

Campbell et al., Allergen immunotherapy: novel approaches in the management of allergic diseases and asthma. Clin Immunol. Dec. 2000;97(3):193-202.

Cockcroft et al., Comparative effects of inhaled salbutamol, sodium cromoglycate, and beclomethasone dipropionate on allergen-induced early asthmatic responses, late asthmatic responses, and increased bronchial responsiveness to histamine. J Allergy Clin Immunol. May 1987;79(5):734-40.

Erb et al., Infection of mice with Mycobacterium bovis-Bacillus Calmette-Guerin (BCG) suppresses allergen-induced airway eosinophilia. J Exp Med. Feb. 16, 1998;187(4):561-9.

Fitch et al., The effect of an oral phosphodiesterase (PDE) 4 inhibitor bay 19-8004 in primate asthma models. American Thoracic Society. 2000. A52 Poster A94.

Gibson et al., Cellular requirements for cytokine production in response to the immunomodulators imiquimod and S-27609. J Interferon Cytokine Res. Jun. 1995;15(6):537-45.

Gundel et al., Antigen-induced mediator release in primates. Am Rev Respir Dis. Jul. 1991;144(1):76-82.

Gundel et al., Repeated antigen inhalation results in a prolonged airway eosinophilia and airway hyperresponsiveness in primates. J Appl Physiol. Feb. 1990;68(2):779-86.

Herz et al., BCG infection suppresses allergic sensitization and development of increased airway reactivity in an animal model. J Allergy Clin Immunol. Nov. 1998;102(5):867-74.

Howarth et al., Influence of albuterol, cromolyn sodium and ipratropium bromide on the airway and circulating mediator responses to allergen bronchial provocation in asthma. Am Rev Respir Dis. Nov. 1985;132(5):986-92.

Hussain et al., CpG oligodeoxynucleotides: a novel therapeutic approach for atopic disorders. Curr Drug Targets Inflamm Allergy. Sep. 2003;2(3):199-205.

Hussain et al., DNA, the immune system, and atopic disease. J Investig Dermatol Symp Proc. Jan. 2004;9(1):23-8.

Jain et al., Mucosal immunotherapy with CpG oligodeoxynucleotides reverses a murine model of chronic asthma induced by repeated antigen exposure. Am J Physiol Lung Cell Mol Physiol. Nov. 2003;285(5):L1137-46.

Jones et al., Pharmacology of montelukast sodium (Singulair), a potent and selective leukotriene D4 receptor antagonist. Can J Physiol Pharmacol. Feb. 1995;73(2):191-201.

Kline et al., Effects of CpG DNA on Th1/Th2 balance in asthma. Curr Top Microbiol Immunol. 2000;247:211-25.

Krieg et al., CpG motifs in bacterial DNA trigger direct B-cell activation. Nature. Apr. 6, 1995;374(6522):546-9.

Krieg et al., Infection. In McGraw Hill Book. 1996: 242-3.

Krieg et al., Lymphocyte activation by CpG dinucleotide motifs in prokaryotic DNA. Trends Microbiol. Feb. 1996;4(2):73-6.

Krown et al., Phase I trial with the interferon inducer polyI/poly-1-lysine (Poly ICL). Journal of Interferon Research. 1983; 3:281-90.

Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.

Lazarus et al., Single-nucleotide polymorphisms in the Toll-like receptor 9 gene (TLR9): frequencies, pairwise linkage disequilibrium, and haplotypes in three U.S. ethnic groups and exploratory case-control disease association studies. Genomics. Jan. 2003;81(1):85-91.

Leigh et al., Effects of montelukast and budesonide on airway responses and airway inflammation in asthma. Am J Respir Crit Care Med. Nov. 1, 2002;166(9):1212-7.

Liu et al., CpG ODN is an effective adjuvant in immunization with tumor antigen. J Invest Med. Sep. 7, 1997;45(7):333A.

Pare et al., Lung mechanics following antigen challenge of *Ascaris suum*-sensitive rhesus monkeys. J Appl Physiol. Nov. 1976;41(5 Pt. 1):668-76

Patterson et al., Inhibition of immunoglobulin E-mediated, antigen-induced monkey asthma and skin reactions by 5, 8, 11, 14-eicosatetraynoic acid. J Allergy Clin Immunol. Feb. 1981;67(2):146-52.

Pisetsky et al., The immunologic properties of DNA. J Immunol. Jan. 15, 1996;156(2):421-3.

Sjolander et al., Iscoms containing purified *Quillaja saponins* upregulate both Th1-like and Th2-like immune responses. Cell Immunol. Apr. 10, 1997;177(1):69-76.

Sonehara et al., Hexamer palindromic oligonucleotides with 5'-CG-3' motif(s) induce production of interferon. J Interferon Cytokine Res. Oct. 1996;16(10):799-803.

Sparwasser et al., Bacterial DNA causes septic shock. Nature. Mar. 27, 1997;386(6623):336-7.

Stein et al., Problems in interpretation of data derived from in vitro and in vivo use of antisense oligodeoxynucleotides. Antisense Res. Dev. 1994 Summer;4(2):67-9.

Stein et al., Non-antisense effects of oligodeoxynucleotides. Antisense Technology. 1997; ch11:241-64.

Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.

Tomai et al., Immunomodulating and antiviral activities of the imidazoquinoline S-28463. Antiviral Res. Nov. 1995;28(3):253-64.

Turner et al., In vitro and in vivo effects of leukotriene B4 antagonism in a primate model of asthma. J Clin Invest. Jan. 15, 1996;97(2):381-7.

Turner et al., Leukotriene D4 receptor antagonism reduces airway hyperresponsiveness in monkeys. Pulm Pharmacol. Feb. 1994;7(1):49-58.

Turner et al., Effects of rolipram on responses to acute and chronic antigen exposure in monkeys. Am J Respir Crit Care Med. May 1994;149(5):1153-9.

Turner et al., Characterization of a primate model of asthma using anti-allergy/anti-asthma agents. Inflamm Res. May 1996;45(5):239-45.

Verthelyi et al., Immunoregulatory activity of CpG oligonucleotides in humans and nonhuman primates. Clin Immunol. Oct. 2003;109(1):64-71.

Witt et al., Phase I trial of an oral immunomodulator and interferon inducer in cancer patients. Cancer Res. Nov. 1, 1993;53(21):5176-80.

Wong et al., Formoterol compared with beclomethasone and placebo on allergen-induced asthmatic responses. Am Rev Respir Dis. Nov. 1992;146(5 Pt 1):1156-60.

Patent Interference No. 105,171. Decision on Motion under 37 CFR §41.125. Mar. 10, 2005.

Patent Interference No. 105,171. Judgment and Order. Mar. 10, 2005.

Patent Interference No. 105,171. Regents of the University of California Notice of Filing Appeal. Mar. 17, 2005.

Patent Interference No. 105,171. Regents of the University of California. Brief of Appellant. Jul. 5, 2005.

Patent Interference No. 105,171. University of Iowa and Coley Pharmaceutical Group, Inc. Brief of Appellees. Aug. 17, 2005.

Patent Interference No. 105,171. Regents of the University of California. Reply Brief of Appellant. Sep. 6, 2005.

Patent Interference No. 105,171. Regents of the University of California. Decision of CAFC. Jul. 17, 2006.

Horner et al., Chapter 22: DNA-based immunotherapeutics for allergic disease. From: Microbial DNA and Host Immunity. 2002:279-87.

Infante-Duarte et al., Th1/Th2 balance in infection. Springer Semin Immunopathol. 1999;21(3):317-38.

Kline et al., Treatment of established asthma in a murine model using CpG oligodeoxynucleotides. Am J Physiol Lung Cell Mol Physiol. Jul. 2002;283(1):L170-9.

McCluskie et al., CpG DNA as mucosal adjuvant. *Vaccine*, 18: 231-237, 2000.

Park et al., The enhanced effect of a hexameric deoxyriboguanosine run conjugation to CpG oligodeoxynucleotides on protection against allergic asthma. J Allergy Clin Immunol. Oct. 2001;108(4):570-6.

Sur et al., Long term prevention of allergic lung inflammation in a mouse model of asthma by CpG oligodeoxynucleotides. J Immunol. May 15, 1999;162(10):6284-93.

Patent Interference No. 105,171. Regents of the Univierisity of California Preliminary Motion 1 (To Designate Additional Claims of the Iowa Patent as Corresponding to the Count). Jun. 7, 2004.

Hogg, J.C., "The pathology of asthma," Review article. *APMIS* 105: 735-745, 1997.

Krieg, A.M., "Immune effects and mechanisms of action of CpG motifs" *Vaccine* 19 (2001) 618-622.

Speigelberg, H.L. et al., "DNA-based approaches to the treatment of allergies" *Curr. Op. In Mol Therap.* (2002) 4(1):64-71.

Robinson, D.S. et al., "Predominant $T_{H2}$-Like Bronchoalveolar T-Lymphocyte Population In Atopic Asthma" *N Engl J Med* 1992; 326:298-304.

Capron et al., Immunologic aspects of schistosomiasis. Annu Rev Med. 1992;43:209-18. Review. Exhibit 2068.

Raz et al., Potential role of immunostimulatory DNA sequences (ISS) in genetic immunization and autoimmunity. ACR Poster Session C: Cytokines and Inflammatory Mediators. Oct. 20, 1996; Abstract No. 615.

Santeliz et al., Amb a 1-linked CpG oligodeoxynucleotides reverse established airway hyperresponsiveness in a murine model of asthma. J Allergy Clin Immunol. Mar. 2002;109(3):455-62. Exhibit 1041.

Tokunga, Response of the rganism to DNA—With a focus on immunostimulatory DNA. Kansen Ensho Meneki. 2001 Autumn; 31(3): 1-12. Japanese. Exhibits 1048 and 1049.

Vlassov et al., Oligonucleotides in cells and in organisms: pharmacological considerations. in Prospects for Antisense Nucleic Acid Therapy of Cancer and AIDS. 1991: 243-66.

Yamamoto, Cytokine production inducing action of oligo DNA. Rinsho Meneki. 1997; 29(9): 1178-84. Japanese. Exhibits 1050, 1047, and 1046.

[No Author Listed] DNA is the primary genetic material. in Recombinant DNA, Second Edition. Watson et al., editors. Scientific American Books, New York. p. 24-5, 147. Exhibit 1003, 1992.

[No Author Listed] Definitions. in the Dictionary of Immunology, Fourth Edition. Herbert et al., editors. Academic Press, 1995. p. 10. Exhibit 1004.

[No Author Listed] http://www.doctorfungus.com/the_fungi/Crytococcus.htm. Exhibit 1029, May 30, 2004.

[No Author Listed] http://www.doctorfungus.com/the_fungi/Blastomyces.htm. Exhibit 1030, May 30, 2004.

[No Author Listed] http://www.doctorfungus.com/the_fungi/Alternaria.htm. Exhibit 1031, May 30, 2004.

[No Author Listed] http://www.cancer.gov/newscenter/pressreleases/cancervaccines/print. Exhibit 1042, Mar. 27, 2003.

[No Author Listed] http://www.cancer.gov/clinicaltrials/learning/cancervaccines/print, Exhibit 1043, Jun. 23, 2004.

[No Author Listed] Recombinant DNA Technology. in Molecular Biology of the Cell. Alberts et al., editors. Garland Publishing, Inc. 1983. Exhibit 2027.

[No Author Listed] Definitions. in Dorland's Illustrated Medical Dictionary, Twenty-sixth Edition. W.B. Saunders Company, 1981. Exhibit 2032.

[No Author Listed] Macromolecules in Prokaryotic and Eukaryotic Cells. in Molecular Cell Biology, Darnell et al, Editors. W.H. Freeman and Company, 1986. Exhibit 2033.

[No Author Listed] Definitions. in Immunology, Roitt et al., Editors. Gower Medical Publishing Company, 1985. Exhibit 2035.

[No Author Listed] Definitions. in Webster's New Collegiate Dictionary. The G&C Merriam Company, 1981. p. 287. Exhibit 2070.

[No Author Listed] http://www.cancer.org/docroot/ETO/content/ETO_1_4X_Cancer_Vaccines_Active_Specific_Immuntherapies.asp. Exhibit 2072, Oct. 1, 2004.

[No Author Listed] http://www.plwc.org/plwc/mainconstructor. Exhibit 2073, Sep. 3, 2003.

[No Author Listed] http://www.icare.org/treatment/tcwvt4.htm. Exhibit 2074, Oct. 1, 2004.

Adya N et al., Expansion of CREB's DNA recognition specificity by Tax results from interaction with Ala-Ala-Arg at positions 282-284 near the conserved DNA-binding domain of CREB. *Proc Natl Acad Sci USA* 91(12):5642-6, Jun. 7, 1994.

Anderson, G., et al., "TH2 and 'TH2-like'cells in allergy and asthma: pharmacological perspectives", *TiPS*, 15:324-332,(1994).

Angier, N., Microbe DNA Seen as Alien by Immune System, *New York Times*, Apr. 11, 1995.

Azad RF et al., Antiviral Activity of a Phosphorothioate Oligonucleotide Complementary to RNA of the Human Cytomegalovirus Major Immediate-Early Region. *Antimicrobial Agents and Chemotherapy*, 37:1945-1954, Sep. 1993.

Azuma, Biochemical and Immunological Studies on Cellular Components of Tubercle Bacilli, Kekkaku, vol. 69, 9:45-55, 1992.

Ballas ZK et al., Induction of NK activity in murine and human cells by CpG motifs in oligodeoxynucleotides and bacterial DNA. *J Immunol* 157(5):1840-5, 1996.

Bayever, E., Systemic Administration of a Phosphorothioate Oligonucleotide with a Sequence Complementary to p53 for Acute Myelogenous leukemia and Myelodysplastic Syndrome: Initial Results of a Phase I Trial, *Antisense Res. & Dev.* (1993), 3:383-390.

Bennett RM et al., DNA binding to human leukocytes. Evidence for a receptor-mediated association, internalization, and degradation of DNA. *J Clin Invest* 76(6):2182-90, 1985.

Blaxter et al., Genes expressed in *Brugia malayi* infective third stage larvae. *Molecular and Biochemical Parasitology*, 77:77-93, Apr. 1996.

Boggs RT et al., Characterization and modulation of immune stimulation by modified oligonucleotides. *Antisense Nucleic Acid Drug Dev* 7(5):461-71, Oct. 1997.

Branda RF et al., Amplification of antibody production by phosphorothioate oligodeoxynucleotides. *J. Lab Clin Med* 128(3):329-38, Sep. 1996.

Branda et al., Immune Stimulation by an Antisense Oligomer Complementary to the rev gene of HIV-1. *Biochemical Pharmacology*, vol. 45, 10:2037-2043, 1993.

Briskin M et al., Lipopolysaccharide-unresponsive mutant pre-B-cell lines blocked in NF-kappa B activation. *Mol Cell Biol* 10(1):422-5, Jan. 1990.

Chace, J. et al., Regulation of Differentiation in CD5+ and Conventional B Cells, *Clinical Immunology and Immunopathology*, (1993), 68:3:327-332.

Chang YN et al., The palindromic series I repeats in the simian cytomegalovirus major immediate-early promoter behave as both strong basal enhancers and cyclic AMP response elements. *J Virol* 64(1):264-77, Jan. 1990.

Chu RS et al., CpG oligodeoxynucleotides act as adjuvants that switch on T helper 1 (Th1) immunity. *J Exp Med* 186(10):1623-31, Nov. 17, 1997.

Cowdery JS et al., Bacterial DNA induces NK cells to produce IFN-gamma in vivo and increases the toxicity of lipopolysaccharides. *J Immunol* 156(12):4570-5, Jun. 15, 1996.

Crosby et al., The Early Responses Gene FGFI-C Encodes a Zinc Finger Transcriptional Activator and is a Member of the GCGGGGGCG (GSG) Element-Binding Protein Family. *Mol. Cell. Biol.*, 2:3835-3841, 1991.

Crystal, Transfer of Genes to Humans: Early Lessons and Obstacles to Success. *Science*, vol. 270, pp. 404-410, 1995.

Englisch et al., Chemically Modified Oligonucleotides as Probes and Inhibitors, *Angew. Chem. Int. Ed. Engl.*, 30:613-629, 1991.

Erb KJ et al., Infection of mice with Mycobacterium bovis-Bacillus Calmette-Guerin (BCG) suppresses allergen-induced airway eosinophilia. *J Exp Med* 187(4):561-9, Feb. 16, 1998.

Etlinger, Carrier sequence selection—one key to successful vaccines, *Immunology Today*, vol. 13, 2:52-55, 1992.

Fox, RI, Mechanism of action of hydroxychloroquine as an antirheumatic drug. *Chemical Abstracts*, 120:15, Abstract No. 182630 (Apr. 29, 1994).

Gura, T., Antisense Has Growing Pains. *Science* (1995), 270:575-576.

Hadden J et al., Immunostimulants. *TIPS*, (1993), 141:169-174.

Hadden J et al., Immunopharmacology, *JAMA*, (1992) 268:20:2964-2969.

Halpern MD et al., Bacterial DNA induces murine interferon-gamma production by stimulation of interleukin-12 and tumor necrosis factor-alpha. *Cell Immunol* 167(1):72-8, 1996.

Hatzfeld J., Release of Early Human Hematopoietic Progenitors from Quiescence by Antisense Transforming Growth Factor β1 or Rb Oligonucleotides, *J. Exp. Med.*, (1991) 174:925-929.

Highfield PE, Sepsis: the More, the Murkier. *Biotechnology*, 12:828, Aug. 12, 1994.

Hoeffler JP et al., Identification of multiple nuclear factors that interact with cyclic adenosine 3',5'-monophosphate response element-binding protein and activating transcription factor-2 by protein-protein interactions. *Mol Endocrinol* 5(2):256-66, Feb. 1991.

Iguchi-Ariga SM and Shaffner W, CpG methylation of the cAMP-responsive enhancer/promoter sequence TGACGTCA abolishes specific factor binding as well as transcriptional activation. *Genes Dev* 3(5):612-9, May 1989.

Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43-52.

Ishikawa R et al., IFN induction and associated changes in splenic leukocyte distribution. *J Immunol* 150(9):3713-27, May 1, 1993.

Jakway JP et al., Growth regulation of the B lymphoma cell line WEHI-231 by anti-immunoglobulin, lipopolysaccharide, and other bacterial products. *J Immunol* 137(7);2225-31, Oct. 1, 1986.

Jaroszewski JW and Cohen JS, Cellular uptake of antisense oligonucleotides. *Adv Drug Delivery Rev* 6(3):235-50, 1991.

Kawano, K., et al., "Analysis and Regulation of interferon-gamma production by peripheral blood lymphocytes from patients with bronchial asthma", Abstract, Arerugi, 43:3:482-91, (1994).

Kimura Y et al., Binding of Oligoguanylate to Scavenger Receptors Is Required for Oligonucleotides to Augment NK Cell Activity and Induce IFN, *J. Biochem.*, vol. 116, 5:991-994, 1994.

Kline JN et al., CpG motif oligonucleotides are effective in prevention of eosinophilic inflammation in a murine model of asthma. *J Invest Med* 44(7):380A, 1996.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2-mediated inflammation in a murine model of asthma. *J Invest Med* 45(7):298A, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879-83, 1996.

Krieg AM, An innate immune defense mechanism based on the recognition of CpG motifs in microbial DNA. *J Lab Clin Med* 128(2):128-33, 1996.

Krieg AM et al., Uptake of oligodeoxyribonucleotides by lymphoid cells is heterogeneous and inducible. *Antisense Res Dev* 1(2):161-71, Summer 1991.

Krieg AM et al., Oligodeoxynucleotide modifications determine the magnitude of B cell stimulation by CpG motifs. *Antisense Nucleic Acid Drug Dev* 6(2):133-9, Summer 1996.

Krieg AM et al., "Modification of antisense phosphodiester oligodeoxynucleotides by a 5' cholesteryl moiety increases cellular association and improves efficacy", *Proc. Natl. Acad. Sci.*, (1993), 90:1048-1052.

Krieg AM et al., "CpG DNA: A Pathogenic Factor in Systemic Lupus Erythematosus?", *Journal of Clinical Immunology*, (1995) 15:6:284-292.

Krieg AM et al, Phosphorothioate Oligodeoxynucleotides: Antisense or Anti-Protein?, *Antisense Research and Development*, (1995), 5:241.

Krieg AM et al., "Leukocyte Stimulation by Oligodeoxynucleotides", *Applied Antisense Oligonucleotide Technology*, (1998), 431-448.

Krieg AM et al., CpG motifs in bacterial DNA trigger direct B-cell activation. *Nature* 374:546-9, 1995.

Krieg AM et al, "The role of CpG dinuleotides in DNA vaccines", Trends in Microbiology, vol. 6, pp. 23-27, Jan. 1998.

Krieg Am el al, A Role for Endogenous Retroviral Sequences in the Regulation of Lymphocyte Activation, the Journal of Immunology, vol. 143, 2448-2451, Oct. 1989.

Kuramoto et al., Oligonucleotide Sequences Required for Natural Killer Cell Activation, *Jpn. J. Cancer Res.*, 83:1128-1131, Nov. 1992.

Leonard et al., Conformation of Guanine 8-Oxoadenine Base Pairs in the Crystal Structure of d(CGCGAATT(08A)GCG). *Biochemistry*, 31(36):8415-8420, 1992.

Macfarlane DE and Manzel L, Antagonism of immunostimulatory CpG-oligonucleotides by quinacrine, chloroquine, and structurally related compounds. *J Immunol* 160(3):1122-31, Feb. 1, 1998.

Mastrangelo et al. *Seminars in Oncology*. vol. 23, 1:4-21, 1996.

Matson S and Krieg AM, Nonspecific suppression of [3H]thymidine incorporation by "control" oligonucleotides. *Antisense Res Dev* 2(4):325-30, Winter 1992.

McIntyre KW et al., A sense phosphorothioate oligonucleotide directed to the initiation codon of transcription factor NF-kappa B p65 causes sequence-specific immune stimulation. Antisense Res Dev 3(4):309-22, Winter 1993.

Messina et al., The Influence of DNA Structure on the in vitro Stimulation of Murine Lymphocytes by Natural and Synthetic Polynucleotide Antigens. *Cellular Immunology*, 147:148-157, 1993.

Messina et al., Stimulation of in vitro Murine Lymphocyte Proliferation by Bacterial DNA. *J. Immunol.*, vol. 147, 6:1759-1764, Sep. 15, 1991.

Mojcik, C., et al., "Administration of a Phosphorothioate Oligonucleotide Antisense Murine Endogenous Retroviral MCF env Causes Immune Effect in vivo in a Sequence-Specific Manner", *Clinical Immunology and Immunopathology*, (1993), 67:2:130-136.

Mottram et al., A novel CDC2-related protein kinase from *Leishmania mexicana* LmmCRK1 is post-translationally regulated during the life cycle. *J. Biol. Chem.* 268:28, 21044-21052 (Oct. 1993).

*New England BIOLABS* 1988-1989 Catalog, item # 1230.

Nyce JW and Metzger WJ, DNA antisense therapy for asthma in an animal model. *Nature* 385:721-725, Feb. 20, 1997.

Pisetsky, D., "Stimulation of in vitro proliferation of murine lymphocytes by synthetic oligodeoxynucleotides", *Molecular Biology Repairs*, (1993) 18:217-221.

Pisetsky et al., Stimulation of Murine Lymphocyte Proliferation by a Phosphorothioate Oligonucleotide with Antisense Activity for Herpes Simplex Virus. *Life Science*, vol. 54, pp. 101-107 (1994).

Pisetsky, The Immunological Properties of DNA, *The Journal of Immunology*, pp. 421-423 (1996).

Pisetsky, Immunological Consequences of Nucleic Acid Therapy, *Antisense Research and Development*, 5:219-225 (1995).

Raz E et al., Preferential induction of a Th1 immune response and inhibition of specific IgE antibody formation by plasmid DNA immunization. *Proc Natl Acad Sci USA* 93(10):5141-5, May 14, 1996.

Ricci, M., et al., "T cells, cytokines, IgE and allergic airways inflammation", *J invest Allergol Clin Immunol*, 4:5;214-220, (1994).

Roman M et al., Immunostimulatory DNA sequences function as T helper-1-promoting adjuvants. *Nat Med* 3(8):849-54, Aug. 1997.

Sato et al., Immunostimulatory DNA Sequences Necessary for Effective Intradermal Gene Immunization, *Science*, vol. 273, pp. 352-354, 1996.

Schnell et al., Identification and characterization of a *Saccharomyces cerevisiae* gene (PAR1) conferring resistance to iron chelators. *Eur. J. Biochem.*, 200:487-493, Sep. 1991.

Schwartz DA et al., CpG motifs in bacterial DNA cause inflammation in the lower respiratory tract. *J Clin Invest* 100(1):68-73, Jul. 1, 1997.

Shirakawa T et al., The inverse association between tuberculin responses and atopic disorder. *Science* 275(5296):77-9, Jan. 3, 1997.

Spiegelberg, H., et al., "Recognition of T Cell Epitopes and Lymphokine Secretion by Rye Grass Allergen *Lolium perenne* I-Specific Human T Cell Clones", *J of Immunology*, 4706-4711, (1994).

Sparwasser T et al., Macrophages sense pathogens via DNA motifs: induction of tumor necrosis factor-alpha-mediated shock. *Eur J Immunol* 27(7):1671-9, Jul. 1997.

Stein CA et al., Oligonucleotides as inhibitors of gene expression: a review. *Cancer Research*, 48:2659-2668, 1988.

Stull et al., Antigene, Ribozyme, and Aptamer Nucleic Acid Drugs: Progress and Prospects, *Pharmaceutical Res.*, vol. 12, 4:465-483, 1995.

Subramanian et al., Theoretical Considerations on the "Spine of Hydration" in the Minor Groove of d(CGCGAATTCGCG) d(GCGCTTAAGCGC): Monte Carlo Computer Simulation. *Proc. Nat'l. Acad. Sci. USA*, 85:1836-1840, 1988.

Tanaka T et al., An antisense Oligonucleotide complementary to a sequence in IG2b increases G2b germline transcripts stimulates B cell DNA synthesis and inhibits immunoglobulin secretion. *J. Exp. Med.*, 175:597-607, 1992.

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol. Immunol.*, vol. 36, 1:55-66, 1992.

Tokunaga et al., A Synthetic Single-Stranded DNA, Ply (dG, dC), Induces Interferon α/β and γ, Augments Natural Killer Activity and Suppresses Tumor Growth. *Jpn. J. Cancer Res.*, 79:682-686, Jun. 1988.

Uhlmann et al., Antisense Oligonucleotides: A New Therapeutic Principle. *Chemical Reviews*, 90:543-584, 1990.

Wagner RW, Gene inhibition using antisense oligodeoxynucleotides. *Nature*, 372:L333-335, 1994.

Walker, C., et al., "Activated T Cells and Cytokines in Bronchoalveolar Lavages from Patients with Various Lung Diseases Associated with Eosinophilia", *Am J Respir Crit Care Med*, 150:1038-1048, (1994).

Wallace et al., Oligonucleotide probes for the screening of recombinant DNA libraries. *Methods in Enzymology*, 152:432-442 (1987).

Weiss R., Upping the Antisense Ante: Scientists bet on profits from reverse genetics. *Science*, 139:108-109, 1991.

Whalen R, DNA Vaccines for Emerging Infection Diseases: What If?, Emerging Infectious Disease, vol. 2, 3:168-175, 1996.

Wu GY et al., Receptor-mediated gene delivery and expression in vivo. *J. Biol. Chem.*, 263:14621-14624, 1988.

Wu-Pong S., Oligonucleotides: Opportunities for Drug Therapy and Research. Pharmaceutical Technology, 18:102-114, 1994.

Yamamoto S et al., DNA from bacteria, but not from vertebrates, induces interferons, activates natural killer cells and inhibits tumor growth. *Microbiol Immunol* 36(9):983-97, 1992.

Yamamoto S et al., In vitro augmentation of natural killer cell activity and production of interferon-alpha/beta and -gamma with deoxyribonucleic acid fraction from *Mycobacterium bovis* BCG. *Jpn J Cancer Res* 79:866-73, Jul. 1988.

Yamamoto S., Mode of Action of Oligonucleotide Fraction Extracted from *Mycobacterium bovis* BCG, *Kekkaku*, vol. 69, 9:29-32, 1994.

Yamamoto S et al., Unique Palindromic Sequences in Synthetic Oligonucleotides are Required to Induce INF and Augment INF-Mediated Natural Killer Activity. *J. Immunol.*, vol. 148, 12:4072-4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.*, 4:119-123, 1994.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol.*, vol. 38, 10:831-836, 1994.

Yamamoto T et al., Synthetic Oligonucleotides with Certain Palindromes Stimulate Interferon Production of Human Peripheral Blood Lymphocytes in vitro. *Jpn. J. Cancer Res.*, 85:775-779, 1994.

Yi, Ae-Kyung et al., IFN-γ Promotes IL-6 and IgM Secretion in Response to CpG Motifs in Bacterial DNA and Oligonucleotides, *The Journal of Immunology*, pp. 558-564 (1996).

Yi, Ae-Kyung et al., Rapid Immune Activation by CpG Motifs in Bacterial DNA, *The Journal of Immunology*, pp. 5394-5402 (1996).

Zhao Q et al., Stage-specific oligonucleotide uptake in murine bone marrow B-cell precursors. *Blood* 84(11):3660-6, Dec. 1, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53-66, Spring 1993.

Hallsworth et al., Selective enhancement of GM-CSF, TNF-alpha, IL-1 beta and IL-8 production by monocytes and macrophages of asthmatic subjects. Eur Respir J. Jun. 1994;7(6):1096-102.

Nyce, Respirable antisense oligonucleotides as novel therapeutic agents for asthma and other pulmonary diseases. Expert Opin Investig Drugs. Sep. 1997;6(9):1149-56.

[No Author Listed] Press Release, Jun. 2006, "Cytos Biotechnology updates on development of allergy vaccine". 4 pages.

[No Author Listed] Press Release, Jan. 2007, "Coley Pharmaceutical Group Updates Hepatitis C Drug Development Strategy". 1 page.

[No Author Listed] Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer". 1 page.

[No Author Listed] CpG oligonucleotide adjuvants modulate allergic response in mouse model.

Allergy Medicine, NewsRx.com. Jan. 16, 2000. (Jahnschmid).

Cooper et al., Safety and immunogenicity of CPG 7909 injection as an adjuvant to Fluarix influenza vaccine. Vaccine. Aug. 13, 2004;22(23-24):3136-43.

Croft et al., "Generation of Polarized Antigen-specific CD8 Effector Populations: Reciprocal Action of Interleukin (IL)-4 and IL-12 in Promoting Type 2 versus Type 1 Cytokine Profiles", J. Exp. Med., Nov. 1994, pp. 1715-1728, vol. 180, The Rockefeller University Press.

Fornadley, Allergy immunotherapy. Otolaryngol Clin North Am. Feb. 1998;31(1):111-27. Abstract Only.

Goldberg et al., Beyond danger: unmethylated CpG dinucleotides and the immunopathogenesis of disease. Immunol Lett. Jul. 3, 2000;73(1):13-8.

Hoffjan et al., Toll-like receptors and airway disease. Drug Discov Today. 2006;3(3):317-24.

Jaroszewski et al., Cellular uptake of antisense oligodeoxynucleotides. Advanced Drug Delivery Reviews. 1991;6:235-50.

Kline et al., CpG oligodeoxynucleotides do not require TH1 cytokines to prevent eosinophilic airway inflammation in a murine model of asthma. J Allergy Clin Immunol. Dec. 1999;104(6):1258-64.

Kou et al., [Analysis and regulation of interferon-gamma production by peripheral blood lymphocytes from patients with bronchial asthma] Arerugi. Mar. 1999;43(3):482-91. Japanese.

Leung, Pathogenesis of atopic dermatitis. J Allergy Clin Immunol. Sep. 1999;104(3 Pt 2):S99-108.

Murad et al., CPG-7909 (PF-3512676, ProMune): toll-like receptor-9 agonist in cancer therapy. Expert Opin Biol Ther. Aug. 2007;7(8):1257-66.

Quddus et al., Treating activated CD4+ T cells with either of two distinct DNA methyltransferase ihibitors, 5-azacytidine or procainamide, is sufficient to cause a lupus-like disease in syngeneic mice. J Clin Invest 92(1):38-53, Jul. 1993.

Rojanasakul et al., Antisense oligonucleotide therapeutics: drug delivery and targeting. Adv Drug Deliv Rev. 1996;18:115-31.

Thorne et al., Experimental grain dust atmospheres generated by wet and dry aerosolization techniques. Am J Ind Med. Jan. 1994;25(1):109-12. Abstract only.

Weeratna et al., Reduction of antigen expression from DNA vaccines by coadministered oligodeoxynucleotides. Antisense Nucleic Acid Drug Dev. Aug. 1998;8(4):351-6.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Yamamoto et al., [Commemorative lecture of receiving Imamura Memorial Prize. II. Mode of action of oligonucleotide fraction extracted from *Mycobacterium bovis* BCG] Kekkaku. Sep. 1994;69(9):571-4. Japanese.

Zimmermann et al., CpG oligodeoxynucleotides trigger protective and curative Th1 responses in lethal murine leishmaniasis. J Immunol. Apr. 15, 1998;160(8):3627-30.

Arora et al., Immunomodulation by liposome entrapped allergen. Mol Cell Biochem. Sep. 21, 1990;97(2):173-9. Abstract Only.

Gavett et al., Interleukin 12 inhibits antigen-induced airway hyperresponsiveness, inflammation, and Th2 cytokine expression in mice. J Exp Med. Nov. 1, 1995;182(5):1527-36.

Hussain et al., Modulation of murine allergic rhinosinusitis by CpG oligodeoxynucleotides. Laryngoscope. Oct. 2002;112(10):1819-26.

Kips et al., Interleukin-12 inhibits antigen-induced airway hyperresponsiveness in mice. Am J Respir Crit Care Med. Feb. 1996;153(2):535-9.

Kline et al., T-lymphocyte dysregulation in asthma. Proc Soc Exp Biol Med. Dec. 1994;207(3):243-53.

Kline, J.N., Eat dirt: CpG DNA and immunomodulation of asthma. Proc Am Thorac Soc. Jul. 2007;4(3):283-8. Review.

Kline, Immunotherapy of asthma using CpG oligodeoxynucleotides. Immunol Res. 2007;39(1-3):279-86. Review.

Kline et al., Ch. 26: DNA Immunomodulation of asthma. In Inflammatory Mechanisms in Allergic Diseases. Ed., Zeiman et al. Marcel Dekker, Inc. 2002;551-64.

Kline et al., Toll-like receptor 9 activation with CpG oligodeoxynucleotides for asthma therapy. Drug News Perspect. Oct. 2008;21(8):434-9.

Mutwiri et al., Biological activity of immunostimulatory CpG DNA motifs in domestic animals. Vet Immunol Immunopathol. Jan. 30, 2003;91(2):89-103.

Roman et al., Gene immunization for allergic disorders. Springer Semin Immunopathol. 1997;19(2):223-32. Review.

Tayyari et al., CpG-oligodeoxynucleotides inhibit RSV-enhanced allergic sensitisation in guinea pigs. Eur Respir J. Feb. 2005;25(2):295-302.

Patent Interference No. 105,171. Regents of the University of California Opposition 11 (to Iowa Contingent Motion 11 to suppress). Oct. 15, 2004.

Patent Interference No. 105,171. Iowa Reply 11 (in support of Iowa Miscellaneous Motion to suppress). (Electronically filed, unsigned). Oct. 18, 2004.

Patent Interference No. 105,526. Krieg Substantive Motion 1 (for unpatentability based on interference estoppel). (Electronically filed, unsigned).

Patent Interference No. 105,526. Krieg Substantive Motion 2 (for judgment based on inadequate written description and/or enablement). (Electronically filed, unsigned). Jun. 18, 2007.

Patent Interference No. 105,526. Krieg Contingent Responsive Motion (to add new claims 104 and 105). (Electronically filed, unsigned). Jul. 25, 2007.

Patent Interference No. 105,526. Krieg Substantive Motion 3 (for judgment based on prior art). (Electronically filed, unsigned). Jun. 18, 2007.

Patent Interference No. 105,526. Raz Motion 1 (Unpatentability of Krieg Claims under 35 U.S.C. § 112, First Paragraph). (Electronically filed, unsigned). Jun. 18, 2007.

Patent Interference No. 105,526. Raz Motion 2 (Raising a Threshold Issue of No Interference-in-Fact). (Electronically filed, unsigned). Jun. 18, 2007.

Patent Interference No. 105,526.. Raz Motion 3 (Krieg's Claims are Unpatentable Over Prior Art Under 35 U.S.C. § 102(b)) (Electronically filed, unsigned). Jun. 18, 2007.

Patent Interference No. 105,526. Raz Motion 4 (To Designate Krieg Claims 46 and 82-84 as Corresponding to Count 1). (Electronically filed, unsigned). Jun. 18, 2007.

Patent Interference No. 105,526. Raz Responsive Miscellaneous Motion 5 (To revive the Raz Parent Application) (Electronically filed, unsigned) Jul. 25, 2007.

Patent Interference No. 105,526. Raz Contingent Responsive Motion 6 (To Add a New Claim 58) (Electronically filed, unsigned) Jul. 25, 2007.

Patent Interference No. 105,526. Krieg Opposition 1 (Opposition to Motion for Lack of Enablement and Written Description) (Electronically filed, unsigned) Sep. 10, 2007.

Patent Interference No. 105,526. Krieg Opposition 2 (to Raz Motion 2) (Electronically filed, unsigned) Sep. 10, 2007.

Patent Interference No. 105,526. Krieg Opposition 3 (To Raz Motion 3) (Electronically filed, unsigned) Sep. 10, 2007.

Patent Interference No. 105,526. Krieg Opposition 4 (Opposition to Motion for Designating Claims 46 and 82-84 as Corresponding to the Court) (Electronically filed, unsigned) Sep. 10, 2007.

Patent Interference No. 105,526. Krieg Opposition 6 (Opposition to Raz Contingent Responsive Motion 6) (Electronically filed, unsigned) Sep. 10, 2007.

Patent Interference No. 105,526. Raz Opposition 1 (Opposing Krieg Substantive Motion 1) (Electronically filed, unsigned) Sep. 10, 2007.

Patent Interference No. 105,526. Raz Opposition 2 (Opposing Krieg Substantive Motion 2) (Electronically filed, unsigned) Sep. 10, 2007.

Patent Interference No. 105,526. Raz Opposition 4 (Opposing Krieg Contingent Responsive Motion to Add New Claims 104 and 105) (Electronically filed, unsigned) Sep. 10, 2007.

Patent Interference No. 105,526. Krieg Reply 1 (Reply to Raz opposition 1) Oct. 5, 2007.

Patent Interference No. 105,526. Krieg Reply 2 (Reply to Raz opposition 2) Oct. 5, 2007.

Patent Interference No. 105,526. Krieg Reply 4 (Reply to Raz opposition 4) Oct. 5, 2007.

Patent Interference No. 105,526. Raz Reply 1 (Reply to Krieg opposition 1) Oct. 5, 2007.

Patent Interference No. 105,526. Raz Reply 2 (Reply to Krieg opposition 2) Oct. 5, 2007.

Patent Interference No. 105,526. Raz Reply 3 (Reply to Krieg opposition 3) Oct. 5, 2007.

Patent Interference No. 105,526. Raz Reply 4 (Reply to Krieg opposition 4) Oct. 5, 2007.

Patent Interference No. 105,526. Raz Reply 6 (Reply to Krieg opposition 6) Oct. 5, 2007.

Patent Interference No. 105,526. Krieg Miscellaneous Motion 5 (To exclude exhibits 2066, 2070, 2071, 2072, 2073, 2074, 2075, 2076 and 2078) Oct. 9, 2007.

Patent Interference No. 105,526. Raz Opposition 5 (Opposing Krieg Miscellaneous Motion 5) Oct. 25, 2007.

Patent Interference No. 105,526. Raz Miscellaneous Motion 7 (To exclude evidence) Oct. 19, 2007.

Patent Interference No. 105,526. Krieg Opposition 7 (To Raz Miscellaneous Motion 7) Oct. 25, 2007.

Patent Interference No. 105,526. Krieg Reply 5 (Reply to Raz opposition 5) Oct. 30, 2007.

Patent Interference No. 105,526. Raz Reply 7 (Reply to Krieg opposition 7) Oct. 30, 2007.

Patent Interference No. 105,526. Order-Bd.R. 104. Conference Call. Paper 211. Sep. 30, 2008.

Patent Interference No. 105,526. Memorandum Opinion and Order (Decision on Motions) Dec. 1, 2008.

Patent Interference No. 105,526. Judgement on Preliminary Motions under 37 C.F.R §41.127 Dec. 1, 2008.

Patent Interference No. 105,526. Paper 217. Raz Notice of Filing of a Notice of Appeal (Appeal to the Court of Appeals for the Federal Circuit). Jan. 27, 2009.

Patent Interference No. 105,526. Paper 219. Raz Notice of Withdrawal of Appeal. May 15, 2009.

Patent Interference No. 105,674. Paper No. 1. Declaration under 37 C.F.R. §41.203(b) Dec. 1, 2008.

Patent Interference No. 105,674. Paper No. 6 Raz Notice of Real Party in Interest. Dec. 12, 2008.

Patent Interference No. 105,674. Paper No. 11 Krieg Designation of Real Party in Interest. Dec. 15, 2008.

Patent Interference No. 105,674. Paper No. 15. Order-Bd.R. 104(c) Summary of Dec. 23, 2008 Conference Call.

Patent Interference No. 105,674. Paper No. 19. Order-Bd.R. 104(c). Conference Call. Jan. 16, 2009.

Patent Interference No. 105,674. Paper No. 21. Raz Observations (regarding evidence to support certain proposed motions. Jan. 27, 2009.

Patent Interference No. 105,674. Paper No. 23. Raz Miscellaneous Motion 1 (to revive the Raz parent application). Jan. 27, 2009.

Patent Interference No. 105,674. Paper No. 25. Order-Bd.R. 104(c) (*Raz* v. *Krieg*) Summary of Conference Call on Feb. 4, 2009.
Patent Interference No. 105,674. Paper No. 29. Joint Submission Pursuant to Order Dated Jan. 16, 2009. Mar. 11, 2009.
Patent Interference No. 105,674. Paper No. 32. Raz Abandonment of Contest. May 15, 2009.
Patent Interference No. 105,674. Paper No. 33. Judgment-Bd.R.127. May 20, 2009.

Fanucchi et al., Immunostimulatory oligonucleotides attenuate airways remodeling in allergic monkeys. Am J Respir Crit Care Med. Dec. 1, 2004;170(11):1153-7. Epub Aug. 11, 2004.
Gauvreau et al., Immunostimulatory sequences regulate interferon-inducible genes but not allergic airway responses. Am J Respir Crit Care Med. Jul. 1, 2006;174(1):15-20. Epub Mar. 30, 2006.

* cited by examiner

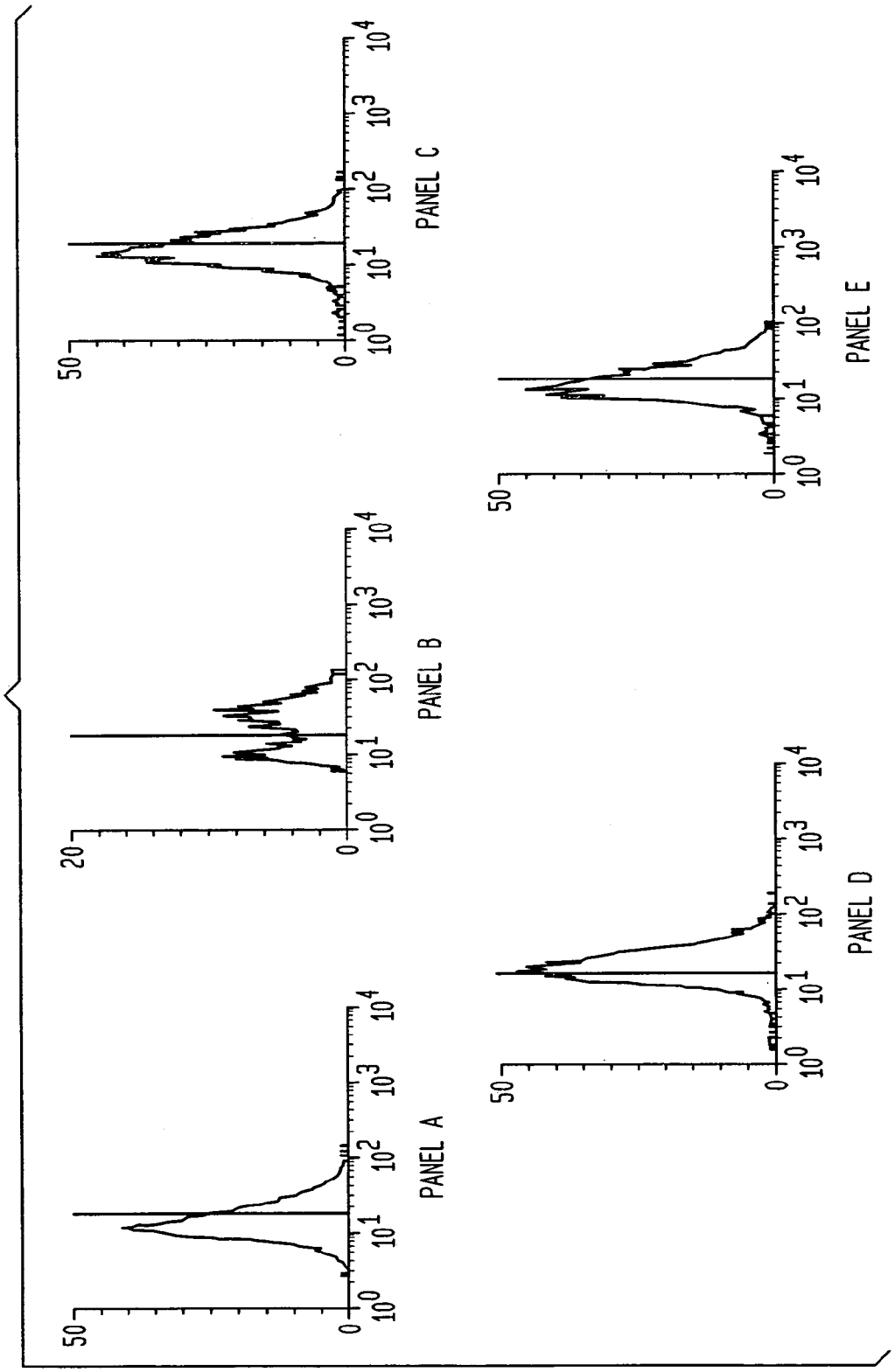

IMMUNOSTIMULATORY NUCLEIC ACID MOLECULES

RELATED APPLICATION

This application is a divisional of U.S. Ser. No. 08/960,774, filed Oct. 30, 1997 now U.S. Pat. No. 6,239,116, which is a continuation-in-part of U.S. Ser. No. 08/738,652, filed Oct. 30, 1996, now U.S. Pat. No. 6,307,646, which is a continuation-in-part of U.S. patent application Ser. No. 08/386,063, filed Feb. 7, 1995, now U.S. Pat. No. 6,194,388, which is a continuation-in-part of U.S. patent application Ser. No. 08/276,358, filed Jul. 15, 1994 now abandoned which is now abandoned, each of which are incorporated herein by reference in their entirety.

GOVERNMENT

The work resulting in this invention was supported in part by National Institute of Health Grant No. R29-AR42556-01. The U.S. Government has rights in the invention.

FIELD OF THE INVENTION

The present invention relates generally to oligonucleotides and more specifically to oligonucleotides which have a sequence including at least one unmethylated CpG dinucleotide which are immunostimulatory.

BACKGROUND OF THE INVENTION

In the 1970s, several investigators reported the binding of high molecular weight DNA to cell membranes (Lerner, R. A., et al. 1971. "Membrane-associated DNA in the cytoplasm of diploid human lymphocytes." *Proc. Natl. Acad. Sci. USA* 68:1212; Agrawal, S. K., R. W. Wagner, P. K. McAllister, and B. Rosenberg. 1975. "Cell-surface-associated nucleic acid in tumorigenic cells made visible with platinum-pyrimidine complexes by electron microscopy." *Proc. Natl. Acad. Sci. USA* 72:928). In 1985, Bennett et al. presented the first evidence that DNA binding to lymphocytes is similar to a ligand receptor interaction: binding is saturable, competitive, and leads to DNA endocytosis and degradation into oligonucleotides (Bennett, R. M., G. T. Gabor, and M. M. Merritt, 1985. "*J. Clin. Invest.* 76:2182). Like DNA, oligodeoxyribonucleotides (ODNs) are able to enter cells in a saturable, sequence independent, and temperature and energy dependent fashion (reviewed in Jaroszewski, J. W., and J. S. Cohen. 1991. "Cellular uptake of antisense oligodeoxynucleotides." *Advanced Drug Deliver Reviews* 6:235; Akhtar, S., Y. Shoji, and R. L. Juliano. 1992. "Pharmaceutical aspects of the biological stability and membrane transport characteristics of antisense oligonucleotides." In: *Gene Regulation: Biology of Antisense RNA and DNA*. R. P. Erickson, and J. G. Izant, eds. Raven Press, Ltd. New York, pp. 133; and Zhao, Q., T. Waldsclunidt, E. Fisher, C. J. Herrera, and A. M. Krieg. 1994. "Stage specific oligonucleotide uptake in murine bone marrow B cell precursors." *Blood* 84:3660). No receptor for DNA or ODN uptake has yet been cloned, and it is not yet clear whether ODN binding and cell uptake occurs through the same or a different mechanism from that of high molecular weight DNA.

Lymphocyte ODN uptake has been shown to be regulated by cell activation. Spleen cells stimulated with the B cell mitogen LPS had dramatically enhanced ODN uptake in the B cell population, while spleen cells treated with the T cell mitogen Con A showed enhanced ODN uptake by T but not B cells (Krieg, A. M., F. Gmelig-Meyling, M. F. Gourley, W. J. Kisch, L. A. Chrisey, and A. D. Steinberg. 1991. "Uptake of oligodeoxyribonucleotides by lymphoid cells is heterogeneous and inducible." Antisense Research and Development 1:161).

Several polynucleotides have been extensively evaluated as biological response modifiers. Perhaps the best example is poly (I,C) which is a potent inducer of IFN production as well as macrophage activator and inducer of NK activity (Talmadge, J. E., J. Adams, H. Phillips, M. Collins, B. Lenz, M. Schneider, E. Schlick, R. Ruffmann, R. H. Wiltrout, and M. A. Chirigos. 1985. "Immunomodulatory effects in mice of polyinosinic-polycytidylic acid complexed with poly-L-lysine and carboxymethylcellulose." *Cancer Res.* 45:1058; Wiltrout, R. H., R. R. Salup, T. A. Twilley, and J. E. Talmadge. 1985. "Immunomodulation of natural killer activity by polyribonucleotides." *J. Biol. Respn. Mod.* 4:512; Krown, S. E. 1986. "Interferons and interferon inducers in cancer treatment." *Sem. Oncol.* 13:207; and Ewel, C. H., S. J. Urba, W. C. Kopp, J. W. Smith II, R. G. Steis, J. L. Rossio, D. L. Longo, M. J. Jones, W. G. Alvord, C. M. Pinsky, J. M. Beveridge, K. L. McNitt, and S. P. Creekmore. 1992. "Polyinosinic-polycytidylic acid complexed with poly-L-lysine and carboxymethylcellulose in combination with interleukin-2 in patients with cancer: clinical and immunological effects."*Canc. Res.* 52:3005). It appears that this murine NK activation may be due solely to induction of IFN-β secretion (Ishikawa, R., and C. A. Biron. 1993. "IFN induction and associated changes in splenic leukocyte distribution". *J. Immunol.* 50:3713). This activation was specific for the robose sugar since deoxyribose was ineffective. Its potent in vitro antitumor activity led to several clinical trials using poly (I,C) complexed with poly-L-lysine and carboxymethylcellulose (to reduce degradation by RNAse) Talmadge, J. E., et al., 1985. cited supra; Wiltrout, R. H., et al., 1985. cited supra); Krown, S. E., 1986. cited supra); and Ewel, C. H., et al., 1992. cited supra). Unfortunately, toxic side effects have thus far prevented poly (I,C) from becoming a useful therapeutic agent.

Guanine ribonucleotides substituted at the C8 position with either a bromine or a thiol group are B cell mitogens and may replace "B cell differentiation factors" (Feldbush, T. L., and Z. K., Ballas. 1985. "Lymphokine-like activity of 8-mercaptoguanosine: induction of T and B cell differentiation." *J. Immunol.* 134:3204; and Goodman, M. G. 1986. "Mechanism of synergy between T cell signals and C8-substituted guanine nucleosides in humoral immunity: B lymphotrophic cytokines induce responsiveness to 8-mercaptoguanosine." *J. Immunol.* 136:3335). 8-mercaptoguanosine and 8-bromo-guanosine also can substitute for the cytokine requirement for the generation of MHC restricted CTL (Feldbush, T. L., 1985. cited supra), augment murine NK activity (Koo, G. C., M. E. Jewell, C. L. Manyak, N. H. Sigal, and L. S. Wicker. 1988. "Activation of murine natural killer cells and macrophages by 8-bromoguanosine." *J. Immunol.* 140:3249), and synergize with IL-2 in inducing murine LAK generation (Thompson, R. A., and Z. K. Ballas. 1990. "Lymphokine-activated killer (LAK) cells. V. 8-Mercaptoguanosine as an IL-2-sparing agent in LAK generation." *J. Immunol.* 145:3524). The NK and LAK augmenting activities of these C8-substituted guanosines appear to be due to their induction of IFN (Thompson, R. A., et al. 1990. cited supra0. Recently, a 5' triphosphorylated thymidine produced by a mycobacterium was found to be mitogenic for a subset of human γδ T cells (Constant, P., F. Davodeau, M.-A. Peyrat, Y. Poquet, G. Puzo, M. Bonneville, and J.-J. Fournie. 1994. "Stimulation of human γδ T cells by nonpeptidic mycobacterial ligands." *Science* 264:267). This report indicated the possibility that the immune system may have evolved ways to preferentially respond to microbial nucleic acids.

Several observations suggest that certain DNA structures may also have the potential to activate lymphocytes. For example, Bell et al. reported that nucleosomal protein-DNA complexes (but not naked DNA) in spleen cell supernatants caused B cell proliferation and immunoglobulin secretion (Bell, D. A., B. Morrison, and P. VandenBygaart. 1990. "Immunogenic DNA-related factors." *J. Clin. Invest.* 85:1487). In other cases, naked DNA has been reported to have immune effects. For example, Messina et al. have recently reported that 260 to 800 by fragments of poly (dG)•(dC) and poly (dG•dC) were mitogenic for 13 cells (Messina, J. P., G. S. Gilkeson, and D. S. Piesetsky. 1993. "The influence of DNA structure on the in vitro stimulation of murine lymphocytes by natural and synthetic polynucleotide antigens." *Cell. Immunol.* 147:148). Tokunaga, et al. have reported that dG•dC induces γ-IFN and NK activity (Tokunaga, S. Yamamoto, and K. Nama. 1988. "A synthetic single-stranded DNA, poly(dG, dC), induces interferon-α/b and -g, augments natural killer activity, and suppresses tumor growth." *Jpn. J. Cancer Res.* 79:682). Aside from such artificial homopolymer sequences, Pisetsky et al. reported that pure mammalian DNA has no detectable immune effects, but that DNA from certain bacteria induces B cell activation and immunoglobulin secretion (Messina, J. P., G. S. Gilkeson, and D. S. Pisetsky. 1991. "Stimulation of in vitro murine lymphocyte proliferation by bacterial DNA." *J. Immunol.* 147:1759). Assuming that these data did not result from some unusual contaminant, these studies suggested that a particular structure or other characteristic of bacterial DNA renders it capable of triggering B cell activation. Investigations of mycobacterial DNA sequences have demonstrated that ODN which contain certain palindrome sequences can activate NK cells (Yamamoto, S., T. Yamamoto, T. Kataoka, E. Kuramoto, O. Yano, and T. Tokunaga. 1992. "Unique palindromic sequences in synthetic oligonucleotides are required to induce INF and augment INF-mediated natural killer activity." *J. Immunol.* 148:4072; Kuramoto, E., O. Yano, Y. Kimura, M. Baba, T. Makino, S. Yamamoto, T. Yamamoto, T. Kataoka, and T. Tokunaga. 1992. "Oligonucleotide sequences required for natural killer cell activation." *Jpn. J. Cancer Res.* 83:1128).

Several phosphorothioate modified ODN have been reported to induce in vitro or in vivo B cell stimulation (Tanaka, T., C. C. Chu, and W. E. Paul. 1992. "An antisense oligonucleotide complementary to a sequence in Ig2b increases g2b germline transcripts, stimulates B cell DNA synthesis, and inhibits immunoglobulin secretion." *J. Exp. Med.* 175:597; McIntyre, K. W., K. Lombard-Gillooly, J. R. Perez, C. Kunsch, U. M. Sarmiento, J. D. Larigan, K. T. Landreth, and R. Narayanan. 1993. "A sense phosphorothioate oligonucleotide directed to the initiation codon of transcription factor NF-κB T65 causes sequence-specific immune stimulation." *Antisense Res. Develop.* 3:309; and Pisetsky, D. S., and C. F. Reich. 1993. "Stimulation of murine lymphocyte proliferation by a phosphorothioate oligonucleotide with antisense activity for herpes simplex virus." *Life Sciences* 59:101). These reports do not suggest a common structural motif or sequence element in these ODN that might explain their effects.

The cAMP response element binding protein (CREB) and activating transcription factor (ATF) or CREB/ATF family of transcription factors is a ubiquitously expressed class of transcription factors of which 11 members have so far been cloned (reviewed on de Groot, R. P., and P. Sassone-Corsi "Hormonal control of gene expression: Multiplicity and versatility of cyclic adenosine 3',5'-monophosphate-responsive nuclear regulators." *Mol. Endocrin.* 7:145, 1993; Lee, K. A. W., and N. Masson: "Transcriptional regulation by CREB and its relatives." *Biochim. Biophys. Acta* 1174:221, 1993). They all belong to the basic region/leucine zipper (bZip) class of proteins. All cells appear to express one or more CREB/ATF proteins, but the members expressed and the regulation of mRNA splicing appear to be tissue-specific. Differential splicing of activation domains can determine whether a particular CREB/ATF protein will be a transcriptional inhibitor or activator. Many CREB/ATF proteins activate viral transcription, but some splicing variants which lack the activation domain are inhibitory. CREB/ATF proteins can bind DNA as homo- or hetero-dimers through the cAMP response element, the CRE, the consensus form of which is the unmethylated sequence TGACGTC (SEQ. ID. No. 103) (binding is abolished if the CpG is methylated) (Iguchi-Ariga, S. M. M., and W. Schaffner: "CpG methylation of the cAMP-responsive enhancer/promoter sequence TGACGTCA (SEQ. ID. No. 104) abolishes specific factor binding as well as transcriptional activation." *Genese & Develop.* 3:612, 1989.

The transcriptional activity of the CRE is increased during B cell activation (Xie. H., T. C. Chiles, and T. L. Rothstein: "Induction of CREB activity via the surface Ig receptor of B cells." *J. Immunol.* 151:880, 1993). CREB/ATF proteins appear to regulate the expression of multiple genes through the CRE including immunologically important genes such as fos, jun B, Rb-1, IL-6, IL-1 (Tsukada, J., K. Saito, W. R. Waterman, A. C. Webb, and P. E. Auron: "Transcription factors NF-IL6 and CREB recognize a common essential site in the human prointerleukin 1 gene." *Mol. Cell. Biol.* 14:7285, 1994; Gray, G. D., O. M. Hernandez, D. Hebel, M. Root, J. M. Pow-Sang, and E. Wickstrom: "Antisense DNA inhibition of tumor growth induced by c-Ha-ras oncogene in nude mice." *Cancer Res.* 53:577, 1993), IFN- (Du, W., and T. Maniatis: "An ATF/CREB binding site protein is required for virus induction of the human interferon B gene." *Proc. Natl. Acad. Sci. USA* 89:2150, 1992), TGF-1 (Asiedu, C. K., L. Scott, R. K. Assoian, M. Ehrlich: "Binding of AP-1/CREB proteins and of MDBP to contiguous sites downstream of the human TGF-B1 gene." *Biochim. Biophys. Acta* 1219:55, 1994), TGF-2, class II MHC (Cox, P. M., and C. R. Goding: "An ATF/CREB binding motif is required for aberrant constitutive expression of the MHC class II Dra promoter and activation by SV40 T-antigen." *Nucl. Acids Res.* 20:4881, 1992), E-selectin, GM-CSF, CD-8, the germline Ig constant region gene, the TCR V gene, and the proliferating cell nuclear antigen (Huang, D., P. M. Shipman-Appasamy, D. J. Orten, S. H. Hinrichs, and M. B. Prystowsky: "Promoter activity of the proliferating-cell nuclear antigen gene is associated with inducible CRE-binding proteins in interleukin 2-stimulated T lymphocytes." *Mol. Cell. Biol.* 14:4233, 1994). In addition to activation through the cAMP pathway, CREB can also mediate transcriptional responses to changes in intracellular $Ca^{++}$ concentration (Sheng, M., G. McFadden, and M. E. Greenberg: "Membrane depolarization and calcium induce c-fos transcription via phosphorylation of transcription factor CREB." *Neuron* 4:571, 1990).

The role of protein-protein interactions in transcriptional activation by CREB/ATF proteins appears to be extremely important. There are several published studies reporting direct or indirect interactions between NFKB proteins and CREB/ATF proteins (Whitley, et al., (1994) *Mol. & Cell. Biol.* 14:6464; Cogswell, et al., (1994) *J. Immun.* 153:712; Hines, et al., (1993) *Oncogene* 8:3189; and Du, et al., (1993) *Cell* 74:887. Activation of CREB through the cyclic AMP pathway requires protein kinase A (PKA), which phosphorylates $CREW^{341}$ on $ser^{133}$ and allows it to bind to a recently cloned protein, CBP (Kwok, R. P. S., J. R. Lundblad, J. C. Chrivia, J. P. Richards, H. P. Bachinger, R. G. Brennan, S. G. E. Roberts, M. R. Green, and R. H. Goodman: "Nuclear protein CBP is a coactivator for the transcription factor CREB." *Nature* 370:223, 1994; Arias, J., A. S. Alberts, P. Brindle, F. X. Claret, T. Smea, M. Karin, J. Feramisco, and M. Montminy: "Activation of cAMP and mitogen responsive genes relies on a common nuclear factor." *Nature* 370:226, 1994). CBP in turn interacts with the basal transcription factor TFIIB causing increased transcription. CREB also has been reported to interact with dTAFII 110, a TATA binding protein-associated factor whose binding may regulate transcription (Ferreri, K., G. Gill, and M. Montminy: "The cAMP-regulated transcription factor CREB interacts with a component of the TFHD complex." *Proc. Natl. Acad. Sci. USA* 91:1210, 1994). In addition to these interactions, CREB/ATF proteins can specifically bind multiple other nuclear factors (Hoeffler, J. P., J. W. Lustbadfer, and C.-Y. Chen: "Identification of multiple nuclear factors that interact with cyclic adenosine 3',5'-monophosphate response element-binding protein and activating transcription factor-2 by protein-protein interactions." *Mol. Endocrinol.* 5:256, 1991) but the biologic significance of most of these interactions is unknown. CREB is normally thought to bind DNA either as a homodimer or as a heterodimer with several other proteins. Surprisingly, CREB monomers constitutively activate transcription (Krajewski, W., and K. A. W. Lee: "A monomeric derivative of the cellular transcription factor CREB functions as a constitutive activator." *Mol. Cell. Biol.* 14:7204, 1994).

Aside from their critical role in regulating cellular transcription, it has recently been shown that CREB/ATF proteins are subverted by some infectious viruses and retroviruses, which require them for viral replication. For example, the cytomegalovirus immediate early promoter, one of the strongest known mammalian promoters, contains eleven copies of the CRE which are essential for promoter function (Chang, Y.-N., S. Crawford, J. Stall, D. R. Rawlins, K.-T. Jeang, and G. S. Hayward: "The palindromic series I repeats in the simian cytomegalovirus major immediate-early promoter behave as both strong basal enhancers and cyclic AMP response elements." *J. Virol.* 64:264, 1990). At least some of the transcriptional activating effects of the adenovirus E1A protein, which induces many promoters, are due to its binding to the DNA binding domain of the CREB/ATF protein, ATF-2, which mediates E1A inducible transcription activation (Liu, F., and M. R. Green: "Promoter targeting by adenovirus E1A through interaction with different cellular DNA-binding domains." *Nature* 368:520, 1994). It has also been suggested that E1A binds to the CREB-binding protein, CBP (Arany, Z., W. R. Sellers, D. M. Livingston, and R. Eckner: "E1A-associated p300 and CREB-associated CBP belong to a conserved family of coactivators." *Cell* 77:799, 1994). Human T lymphotropic virus-I (HTLV-1), the retrovirus which causes human T cell leukemia and tropical spastic paresis, also requires CREB/ATF proteins for replication. In this case, the retrovirus produces a protein, Tax, which binds to CREB/ATF proteins and redirects them from their normal cellular binding sites to different DNA sequences (flanked by G- and G-rich sequences) present within the HTLV transcriptional enhancer (Paca-Uccaralertkun, S., L.-J. Zhao, N. Adya, J. V. Cross, B. R. Cullen, I. M. Boros, and C.-Z. Giam: "In vitro selection of DNA elements highly responsive to the human T-cell lymphotropic virus type I transcriptional activator, Tax." *Mol. Cell. Biol.* 4:456, 1994; Adya, N., L.-J. Zhao, W. Huang, I. Boros, and C.-Z. Giam: "Expansion of CREB's DNA recognition specificity by Tax results from interaction with Ala-Arg at positions 282-284 near the conserved DNA-binding domain of CREB." *Proc. Natl. Acad. Sci. USA* 91:5642, 1994).

SUMMARY OF THE INVENTION

The present invention is based on the finding that certain nucleic acids containing unmethylated cytosine-guanine (CpG) dinucleotides activate lymphocytes in a subject and redirect a subject's immune response from a Th2 to a Th1 (e.g., by inducing monocytic cells and other cells to produce Th1 cytokines, including IL-12, IFN-γ and GM-CSF). Based on this finding, the invention features, in one aspect, novel immunostimulatory nucleic acid compositions.

In one embodiment, the invention provides an isolated immunostimulatory nucleic acid sequence containing a CpG motif represented by the formula:

wherein at least one nucleotide separates consecutive CpGs; $X_1$ is adenine, guanine, or thymine; $X_2$ is cytosine or thymine; N is any nucleotide and $N_1+N_2$ is from about 0-26 bases with the proviso that $N_1$ and $N_2$ do not contain a CCGG quadmer or more than one CCG or CGG trimer; and the nucleic acid sequence is from about 8-30 bases in length.

In another embodiment, the invention provides an isolated immunostimulatory nucleic acid sequence contains a CpG motif represented by the formula:

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0-26 bases with the proviso that $N_1$ and $N_2$ do not contain a CCGG quadmer or more than one CCG or CGG trifler; and the nucleic acid sequence is from about 8-30 bases in length.

In another embodiment, the invention provides a method of stimulating immune activation by administering the nucleic acid sequences of the invention to a subject, preferably a human. In a preferred embodiment, the immune activation effects predominantly a Th1 pattern of immune activation.

In another embodiment, the nucleic acid sequences of the invention stimulate cytokine production. In particular, cytokines such as IL-6, IL-12, IFN-γ, TNF-α and GM-CSF are produced via stimulation of the immune system using the nucleic acid sequences described herein. In another aspect, the nucleic acid sequences of the invention stimulate the lytic activity of natural killer cells (NK) and the proliferation of B cells.

In another embodiment, the nucleic acid sequences of the invention are useful as an artificial adjuvant for use during antibody generation in a mammal such as a mouse or a human.

In another embodiment, autoimmune disorders are treated by inhibiting a subject's response to CpG mediated leukocyte activation. The invention provides administration of inhibitors of endosomal acidification such as bafilomycin a, chloroquine, and monensin to ameliorate autoimmune disorders. In particular, systemic lupus erythematosus is treated in this manner.

The nucleic acid sequences of the invention can also be used to treat, prevent or ameliorate other disorders (e.g., a tumor or cancer or a viral, fungal, bacterial or parasitic infection). In addition, the nucleic acid sequences can be administered to stimulate a subject's response to a vaccine. Furthermore, by redirecting a subject's immune response from Th2 to Th1, the claimed nucleic acid sequences can be used to treat or prevent an asthmatic disorder. In addition, the claimed nucleic acid molecules can be administered to a subject in conjunction with a particular allergen as a type of desensitization therapy to treat or prevent the occurrence of an allergic reaction associated with an asthmatic disorder.

Further, the ability of the nucleic acid sequences of the invention described herein to induce leukemic cells to enter the cell cycle supports their use in treating leukemia by increasing the sensitivity of chronic leukemia cells followed by conventional ablative chemotherapy, or by combining the nucleic acid sequences with other immunotherapies.

Other features and advantages of the invention will become more apparent from the following detailed description and claims.

BRIEF DESCRIPTION OF THE FIGURES

FIGS. 1A-C are graphs plotting dose-dependent IL-6 production in response to various DNA sequences in T cell depleted spleen cell cultures.

FIG. 1A. *E. coli* DNA (1) and calf thymus DNA (n) sequences and LPS (at 10× the concentration of *E. coli* and calf thymus DNA) (u).

FIG. 1B. Control phosphodiester oligodeoxynucleotide (ODN) 5' ATGGAAGGTCCAGTGTTCTC 3' (SEQ ID NO: 114) (n) and two phosphodiester CpG ODN 5' ATCGACCTACGTGCGTTCTC 3' (SEQ ID NO: 2) (u) and 5' TCCATAACGTTCCTGATGCT 3' (SEQ ID NO: 3) (1).

FIG. 1C. Control phosphorothioate ODN 5' GCTAGATGTTAGCGT 3' (SEQ ID NO: 4) (n) and two phosphorothioate CpG ODN 5' GAGAACGTCGACCTTCGAT 3' (SEQ ID NO: 5) (u) and 5' GCATGACGTTGAGCT 3' (SEQ ID NO: 6) (1). Data present the mean±standard deviation of triplicates.

FIG. 2 is a graph plotting IL-6 production induced by CpG DNA in vivo as determined 1-8 hrs after injection. Data represent the mean from duplicate analyses of sera from two mice. BALB/c mice (two mice/group) were injected iv. with 100 μl of PBS (o) of 200 μg of CpG phosphorothioate ODN 5'CCATGACGTTCCTGATGCT 3' (SEQ ID NO: 7) (n) or non-CpG phosphorothioate ODN 5' TCCATGAGCTTCCTGAGTCT 3' (SEQ ID NO: 8 (u).

FIG. 3 is an autoradiograph showing IL-6 mRNA expression as determined by reverse transcription polymerase chain reaction in liver, spleen, and thymus at various time periods after in vivo stimulation of BALB/c mice (two mice/group) injected iv with 100 μl of PBS, 200 μg of CpG phosphorothioate ODN 5' TCCATGACGTTCCTGATGCT 3' (SEQ ID NO: 7) or non-CpG phosphorothioate ODN 5' TCCATGAGCTTCCTGAGTCT 3' (SEQ ID NO: 8).

FIG. 4A is a graph plotting dose-dependent inhibition of CpG-induced IgM production by anti-IL-6. Splenic B-cells from DBA/2 mice were stimulated with CpG ODN 5' TCCAAGACGTTCCTGATGCT 3' (SEQ ID NO: 9) in the presence of the indicated concentrations of neutralizing anti-IL-6 (u) or isotype control Ab (1) and IgM levels in culture supernatants determined by ELISA. In the absence of CpG ODN, the anti-IL-6 Ab had no effect on IgM secretion (n).

FIG. 4B is a graph plotting the stimulation index of CpG-induced splenic B cells cultured with anti-L-6 and CpG S-ODN 5' TCCATGACGTTCCTGATGCT 3' (SEQ ID NO: 7) (u) or anti-IL-6 antibody only (n). Data present the mean±standard deviation of triplicates.

FIG. 5 is a bar graph plotting chloramphenicol acetyltransferase (CAT) activity in WEHI-231 cells transfected with a promoter-less CAT construct (pCAT), positive control plasmid (RSV), or IL-6 promoter-CAT construct alone or cultured with CpG 5' TCCATGACGTTCCTGATGCT 3' (SEQ ID NO: 7) or non-CpG 5' TCCATGAGCTTCCTGAGTCT 3' (SEQ ED NO: 8) phosphorothioate ODN at the indicated concentrations. Data present the mean of triplicates.

FIG. 6 is a schematic overview of the immune effects of the immunostimulatory unmethylated CpG containing nucleic acids, which can directly activate both B cells and monocytic cells (including macrophages and dendritic cells) as shown. The immunostimulatory oligonucleotides do not directly activate purified NK cells, but render them competent to respond to IL-12 with a marked increase in their IFN-γ secretion by NK cells, the immunostimulatory nucleic acids promote a Th1 type immune response. No direct activation of proliferation of cytokine secretion by highly purified T cells has been found. However, the induction of Th1 cytokine secretion by the immunostimulatory oligonucleotides promotes the development of a cytotoxic lymphocyte response.

FIG. 7 is an autoradiograph showing NFκB mRNA induction in monocytes treated with *E. coli* (EC) DNA (containing unmethylated CpG motifs), control (CT) DNA (containing no unmethylated CpG motifs) and lipopolysaccharide (LPS) at various measured times, 15 and 30 minutes after contact.

FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. This level of reactive oxygen species was greatly increased to 80% in the cells treated for 20 minutes with PMA and ionomycin, a positive control (Panel B). The cells treated with the CpG oligo (TCCATGACGTTCCTGACGTT SEQ ID NO: 10) also showed an increase in the level of reactive oxygen species such that more than 50% of the cells became positive (Panel D). However, cells treated with an oligonucleotide with the identical sequence except that the CpGs were switched (TCCATGAGCTTCCTGAGTCT SEQ ID NO: 8) did not show this significant increase in the level of reactive oxygen species (Panel E).

FIG. 8B shows the results from a flow cytometry study using mouse B cells in the presence of chloroquine with the dihydrorhodamine 123 dye to determine levels of reactive oxygen species. Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in the cells treated with PMA and ionomycin (Panel E).

FIG. 9 is a graph plotting lung lavage cell count over time. The graph shows that when the mice are initially injected with *Schistosoma mansoni* eggs "egg", which induces a Th2 immune response, and subsequently inhale *Schistosoma mansoni* egg antigen "SEA" (open circle), many inflammatory cells are present in the lungs. However, when the mice are initially given CpG oligo (SEQ ID NO: 10) along with egg, the inflammatory cells in the lung are not increased by subsequent inhalation of SEA (open triangles).

FIG. 10 is a graph plotting lung lavage eosinophil count over time. Again, the graph shows that when the mice are initially injected with egg and subsequently inhale SEA (open circle), many eosinophils are present in the lungs. However, when the mice are initially given CpG oligo (SEQ ID NO: 10) along with egg, the inflammatory cells in the lung are not increased by subsequent inhalation of the SEA (open triangles).

FIG. 11 is a bar graph plotting the effect on the percentage of macrophage, lymphocyte, neutrophil and eosinophil cells induced by exposure to saline alone; egg, then SEA; egg and SEQ ID NO: 11, then SEA; and egg and control oligo (SEQ ID NO: 11), then SEA. When the mice are treated with the control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

DETAILED DESCRIPTION OF THE INVENTION

Definitions

Figure 1A:
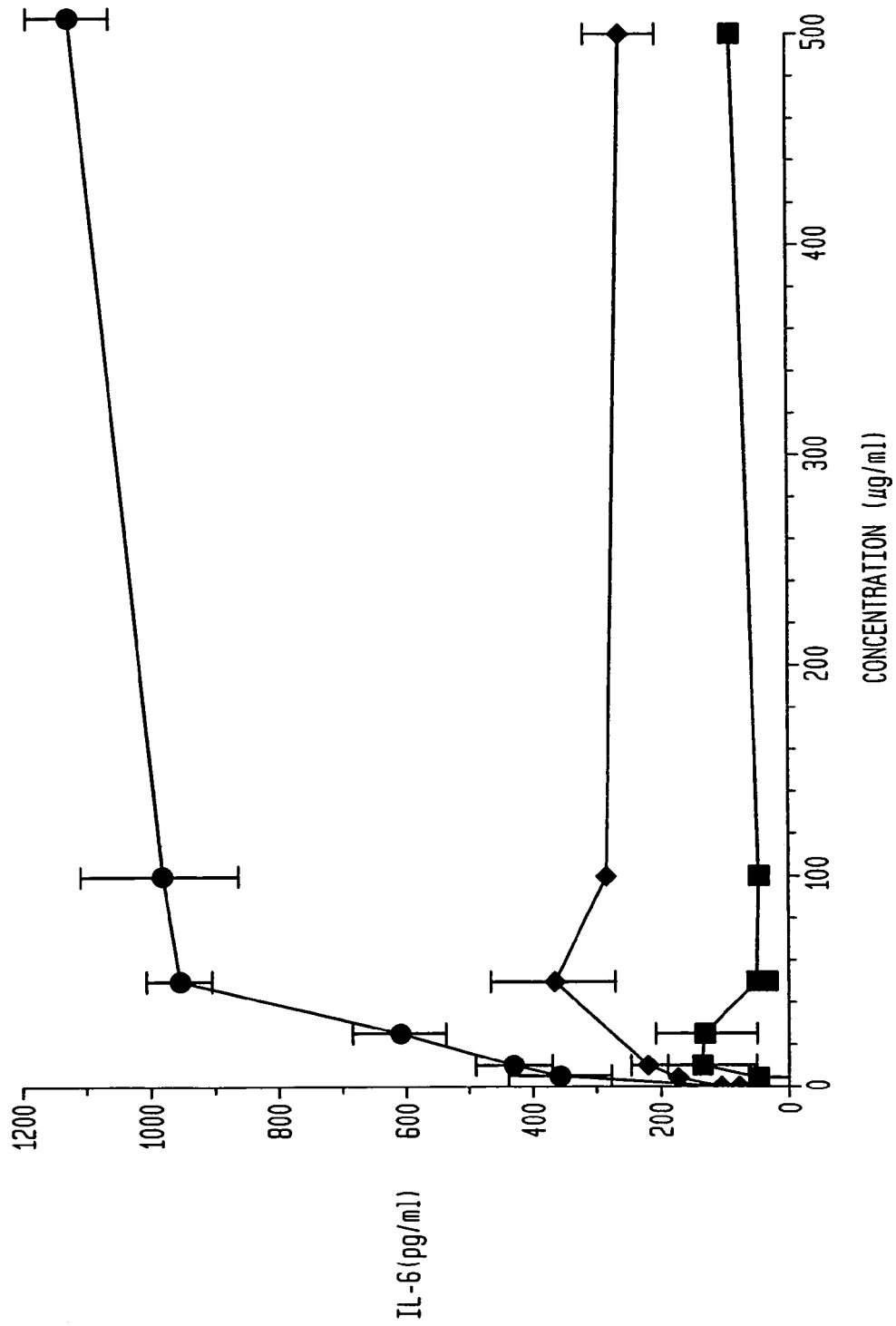

As used herein, the following terms and phrases shall have the meanings set forth below:

An "allergen" refers to a substance that can induce an allergic asthmatic response in a susceptible subject. The list of allergens is enormous and can include pollens, insect venoms, animal dander dust, fungal spores and drugs (e.g., penicillin). Examples of natural, animal and plant allergens include proteins specific to the following genuses: Canine (*Canis familiaris*), *Dermatophagoides* (e.g., *Dermatophagoides farinae*); *Felis* (*Felis domesticus*); *Ambrosia* (*Ambrosia artemiisfolia; Lolium* (e.g., *Lolium perenne* or *Lolium multiflorum*); *Cryptomeria* (*Cryptomeria japonica*); *Alternaria* (*Alternaria alternata*); Alder; *Alnus* (*Alnus gultinosa*); *Betula* (*Betula verrucosa*); *Quercus* (*quercus alba*); *Olea* (*Olea europa*); *Artemisia* (*Artemisia vulgaris*); *Plantago* (e.g., *Plantago lanceolata*); *Parietaria* (e.g., *Parietaria officinalis* or *Parietaria judaica*); *Blattella* (e.g., *Blattella germanica*); *Apis* (e.g., *Apis multiflorum*); *Cupressus* (e.g., *Cupressus sempervirens, Cupressus arizonica* and *Cupressus macrocarpa*); *Juniperus* (e.g., *Juniperus sabinoides, Juniperus virginiana, Juniperus communis* and *Juniperus ashei*); *Thuya* (e.g., *Thuya orientalis*), *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* or *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*) and *Bromus* (e.g., *Bromus inermis*).

An "allergy" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

An "immune system deficiency" shall mean a disease or disorder in which the iii subject's immune system is not functioning in normal capacity or in which it would be useful to boost a subject's immune response for example to eliminate a tumor or cancer (e.g., tumors of the brain, lung (e.g., small cell and non-small cells), ovary, breast, prostate, colon, as well as other carcinomas and sarcomas) or an infection in a subject.

Examples of infectious virus include: Retroviridae (e.g., human immunodeficiency viruses, such as HIV-1, also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); to Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1—internally transmitted; class 2—parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (e.g., *M. tuberculosis, M. avium, M. Intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Ery-* sipelothrix rhusiopathiae, Clostridium perfringers, Clostridium tetani, Enterobacter erogenes, Klebsiella pneuomiae, Pasturella multicoda, Bacteroides sp., Fusobacterium nucleatum, Sreptobacillus moniliformis, Treponema pallidium, Treponema pertenue, Leptospira, and Actinomeyces israelli.

Examples of infectious fungi include: *Cryptococcus neoformans*, *Histoplasma capsulatum*, *Coccidioides immitis*, *Blastomyces dermatitidis*, *Chlamydia trachomatis*, *Candida albicans*. Other infectious organisms (i.e., protists) include: *Plasmodium falciparum* and *Toxoplasma gondii*.

An "immunostimulatory nucleic acid molecule" refers to a nucleic acid molecule, which contains an unmethylated cytosine, guanine dinucleotide sequence (i.e., "CpG DNA" or DNA containing a cytosine followed by guanosine and linked by a phosphate bond) and stimulates (e.g., has a motogenic effect on, or induces or increases cytokine expression by) a vertebrate lymphocyte. An immunostimulatory nucleic acid molecule can be double-stranded or single-stranded. Generally, double-stranded molecules are more stable in vivo, while single-stranded molecules have increased immune activity.

In one preferred embodiment, the invention provides an isolated immunostimulatory nucleic acid sequence containing a CpG motif represented by the formula:

$$5'N_1X_1CGX_2N_23'$$

wherein at least one nucleotide separates consecutive CpGs; $X_1$ is adenine, guanine, or thymine; $X_2$ is cytosine or thymine; N is any nucleotide and $N_1+N_2$ is from about 0-26 bases with the proviso that $N_1$ and $N_2$ do not contain a CCGG quadmer or more than one CCG or CGG trimer; and the nucleic acid sequence is from about 8-30 bases in length.

In another embodiment the invention provides an isolated immunostimulatory nucleic acid sequence contains a CpG motif represented by the formula:

$$5'N_1X_1X_2CGX_3X_4N_23'$$

wherein at least one nucleotide separates consecutive CpGs; $X_1X_2$ is selected from the group consisting of GpT, GpG, GpA, ApT and ApA; $X_3X_4$ is selected from the group consisting of TpT or CpT; N is any nucleotide and $N_1+N_2$ is from about 0-26 bases with the proviso that $N_1$ and $N_2$ do not contain a CCGG quadmer or more than one CCG or CGG trimer; and the nucleic acid sequence is from about 8-30 bases in length.

Preferably, the immunostimulatory nucleic acid sequences of the invention include $X_1X_2$ selected from the group consisting of GpT, GpG, GpA and ApA and $X_3X_4$ is selected from the group consisting of TpT, CpT and GpT (see for example, Table 5). For facilitating uptake into cells, CpG containing immunostimulatory nucleic acid molecules are preferably in the range of 8 to 30 bases in length. However, nucleic acids of any size (even many kb long) are immunostimulatory if sufficient immunostimulatory motifs are present, since such larger nucleic acids are degraded into oligonucleotides inside of cells. Preferred synthetic oligonucleotides do not include a CGG quadmer or more than one CCG or CGG trimer at or near the 5' and/or 3' terminals and/or the consensus mitogenic CpG motif is not a palindrome. Prolonged immunostimulation can be obtained using stabilized oligonucleotides, where the oligonucleotide incorporates a phosphate backbone modification. For example, the modification is a phosphorothioate or phosphorodithioate modification. More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid.

Preferably the immunostimulatory CpG DNA is in the range of between 8 to 30 bases in size when it is an oligonucleotide. Alternatively, CpG dinucleotides can be produced on a large scale in plasmids, which after being administered to a subject are degraded into oligonucleotides. Preferred immunostimulatory nucleic acid molecules (e.g., for use in increasing the effectiveness of a vaccine or to treat an immune system deficiency by stimulating an antibody (i.e., humoral) response in a subject) have a relatively high stimulation index with regard to B cell, monocyte and/or natural killer cell responses (e.g., cytokine, proliferative, lytic or other responses).

The nucleic acid sequences of the invention stimulate cytokine production in a subject for example. Cytokines include but are not limited to IL-6, IL-12, IFN-γ, TNF-α and GM-CSF. Exemplary sequences include: TCCATGTCGCTCCTGATGCT (SEQ ID NO: 37), TCCATGTCGTTCCTGATGCT (SEQ ID NO: 38), and TCGTCGTTTTGTCGTTTTGTCGTT (SEQ ID NO: 46).

The nucleic acid sequences of the invention are also useful for stimulating natural killer cell (NK) lytic activity in a subject such as a human. Specific, but non-limiting examples of such sequences include: TCGTCGTTGTCGTTGTCGTT (SEQ ID NO: 47), TCGTCGTTTTGTCGTTTTTTGTCGTT (SEQ ID NO: 46), TCGTCGTTGTCGTTTTGTCGTT (SEQ ID NO: 49), GCGTGCGTTGTCGTTGTCGTT (SEQ ID NO: 56), TGTCGTTTGTCGTTTGTCGTT (SEQ ID NO: 48), TGTCGTTGTCGTTGTCGTT (SEQ ID NO: 50) and TCGTCGTCGTCGTT (SEQ ID NO: 51).

The nucleic acid sequences of the invention are useful for stimulating B cell proliferation in a subject such as a human. Specific, but non-limiting examples of such sequences include: TCCTGTCGTTCCTTGTCGTT (SEQ ID NO: 52), TCCTGTCGTTTTTTGTCGTT (SEQ ID NO: 53), TCGTCGCTGTCTGCCCTTCTT (SEQ ID NO: 54), TCGTCGCTGTGTCGTTTCTT (SEQ ID NO: 55), TCGTCGTTTTGTCGTTTTGTCGTT (SEQ ID NO: 46), TCGTCGTTGTCGTTTTGTCGTT (SEQ ID NO: 49) and TGTCGTTGTCGTTGTCGTT (SEQ ID NO: 50).

In another aspect, the nucleic acid sequences of the invention are useful as an adjuvant for use during antibody production in a mammal. Specific, but non-limiting examples of such sequences include: TCCATGACGTTCCTGACGTT (SEQ ID NO: 10), GTCGTT (SEQ. ID. NO: 57), GTCGCT (SEQ. ID. NO. 58), TGTCGCT (SEQ. ID. NO: 101) and TGTCGTT (SEQ. ID. NO: 102). Furthermore, the claimed nucleic acid sequences can be administered to treat or prevent the symptoms of an asthmatic disorder by redirecting a subject's immune response from Th2 to Th1. An exemplary sequence includes TCCATGACGTTCCTGACGTT (SEQ ID NO: 10).

The stimulation index of a particular immunostimulatory CpG DNA can be tested in various immune cell assays. Preferably, the stimulation index of the immunostimulatory CpG DNA with regard to B-cell proliferation is at least about 5, preferably at least about 10, more preferably at least about 15 and most preferably at least about 20 as determined by incorporation of $^3$H uridine in a murine B cell culture, which has been contacted with a 20 μM of ODN for 20 h at 37° C. and has peen pulsed with 1 μCi of $^3$H uridine; and harvested and counted 4 h later as described in detail in Example 1. For use in vivo, for example to treat an immune system deficiency by stimulating a cell-mediated (local) immune response in a subject, it is important that the immunostimulatory CpG DNA be capable of effectively inducing cytokine secretion by monocytic cells and/or Natural Killer (NK) cell lytic activity.

Preferred immunostimulatory CpG nucleic acids should effect at least about 500 pg/ml of TNF-α, 15 pg/ml IFN-γ, 70 pg/ml of GM-CSF 275 pg/ml of IL-6, 200 pg/ml IL-12, depending on the therapeutic indication, as determined by the assays described in Example 12. Other preferred immunostimulatory CpG DNAs should effect at least about 10%, more preferably at least about 15% and most preferably at least about 20% YAC-1 cell specific lysis or at least about 30, more preferably at least about 35 and most preferably at least about 40% 2C11 cell specific lysis as determined by the assay described in detail in Example 4.

A "nucleic acid" or "DNA" means multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the term refers to ribonucleotides as well as oligodeoxyribonucleotides. The term shall also include polynucleotides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by oligonucleotide synthesis).

A "nucleic acid delivery complex" shall mean a nucleic acid molecule associated with (e.g., ionically or covalently bound to; or encapsulated within) a targeting means (e.g., a molecule that results in higher affinity binding to target cell (e.g., B-cell and natural killer (NK) cell) surfaces and/or increased cellular uptake by target cells). Examples of nucleic acid delivery complexes include nucleic acids associated with: a sterol (e.g., a ligand recognized by target cell specific receptor). Preferred complexes must be sufficiently stable in vivo to prevent significant uncoupling prior to internalization by the target cell. However, the complex should be cleavable under appropriate conditions within the cell so that the nucleic acid is released in a functional form.

"Palindromic sequences" shall mean an inverted repeat (i.e., a sequence such as ABCDEE'D'C'B'A' in which A and A' are bases capable of forming the usual Watson-Crick base pairs. In vivo, such sequences may form double stranded structures.

A "stabilized nucleic acid molecule" shall mean a nucleic acid molecule that is relatively resistant to in vivo degradation (e.g., via an exo- or endo-nuclease). Stabilization can be a function of length or secondary structure. Unmethylated CpG containing nucleic acid molecules that are tens to hundreds of kbs long are relatively resistant to in vivo degradation. For shorter immunostimulatory nucleic acid molecules, secondary structure can stabilize and increase their effect. For example, if the 3' end of a nucleic acid molecule has self-complementarily to an upstream region, so that it can fold back and form a sort of stem loop structure, then the nucleic acid molecule becomes stabilized and therefore exhibits more activity.

Preferred stabilized nucleic acid molecules of the instant invention have a modified backbone. For use in immune stimulation, especially preferred stabilized nucleic acid molecules are phosphorothioate (i.e., at least one of the phosphate oxygens of the nucleic acid molecules is replaced by sulfur) or phosphorodithioate modified nucleic acid molecules. More particularly, the phosphate backbone modification occurs at the 5' end of the nucleic acid for example, at the first two nucleotides of the 5' end of the nucleic acid. Further, the phosphate backbone modification may occur at the 3' end of the nucleic acid for example, at the last five nucleotides of the 3' end of the nucleic acid. In addition to stabilizing nucleic acid molecules, as reported further herein, phosphorothioate-modified nucleic acid molecules (including phosphorodithioate-modified) can increase the extent of immune stimulation of the nucleic acid molecule, which contains an unmethylated CpG dinucleotide as shown herein. International Patent Application Publication Number WO 95/26204 entitled "Immune Stimulation By Phosphorothioate Oligonucleotide Analogs" also reports on the non-sequence specific immunostimulatory effect of phosphorothioate modified oligonucleotides. As reported herein, unmethylated CpG containing nucleic acid molecules having a phosphorothioate backbone have been found to preferentially activate B-cell activity, while unmethylated CpG containing nucleic acid molecules having a phosphodiester backbone have been found to preferentially activate monocytic (macrophages, dendritic cells and monocytes) and NK cells. Phosphorothioate CpG oligonucleotides with preferred human motifs are also strong activators of monocytic and NK cells.

Other stabilized nucleic acid molecules include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Nucleic acid molecules which contain a diol, such as tetraethylenglycol or hexaethyleneglycol, at either or both termini have also been shown to be substantially resistant to nuclease degradation.

A "subject" shall mean a human or vertebrate animal including a dog, cat, horse, cow, pig, sheep, goat, chicken, monkey, rat, and mouse.

As used herein, the term "vector" refers to a nucleic acid molecule capable of transporting another nucleic acid to which it has been linked. Preferred vectors are those capable of autonomous replication and expression of nucleic acids to which they are linked (e.g., an episome). Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Certain Unmethylated CpG Containing Nucleic Acids have B Cell Stimulatory Activity as Shown In Vitro and In Vivo In the course of investigating the lymphocyte stimulatory effects of two antisense oligonucleotides specific for endogenous retroviral sequences, using protocols described in the attached Examples 1 and 2, it was surprisingly found that two out of twenty-four "controls" (including various scrambled, sense, and mismatch controls for a panel of "antisense" ODN) also mediated B cell activation and IgM secretion, while the other "controls" had no effect.

Two observations suggested that the mechanism of this B cell activation by the "control" ODN may not involve antisense effects 1) comparison of vertebrate DNA sequences listed in GenBank showed no greater homology than that seen with non-stimulatory ODN and 2) the two controls showed no hybridization to Northern blots with 10 μg of spleen poly A+RNA. Resynthesis of these ODN on a different synthesizer or extensive purification by polyacrylamide gel electrophoresis or high pressure liquid chromatography gave identical stimulation, eliminating the possibility of an impurity. Similar stimulation was seen using B cells from C3H/HeJ mice, eliminating the possibility that lipopolysaccharide (LPS) contamination could account for the results.

The fact that two "control" ODN caused B cell activation similar to that of the two "antisense" ODN raised the possibility that all four ODN were stimulating B cells through some non-antisense mechanism involving a sequence motif that was absent in all of the other nonstimulatory control ODN. In comparing these sequences, it was discovered that all of the four stimulatory ODN contained CpG dinucleotides that were in a different sequence context from the nonstimulatory control.

To determine whether the CpG motif present in the stimulatory ODN was responsible for the observed stimulation, over 300 ODN ranging in length from 5 to 42 bases that contained methylated, unmethylated, or no CpG dinucleotides in various sequence contexts were synthesized. These ODNs, including the two original "controls" (ODN 1 and 2) and two originally synthesized as "antisense" (ODN 3D and 3M; Krieg, A. M. J. Immunol. 143:2448 (1989)), were then examined for in vitro effects on spleen cells (representative sequences are listed in Table 1). Several ODN that contained CpG dinucleotides induced B cell activation and IgM secretion; the magnitude of this stimulation typically could be increased by adding more CpG dinucleotides (Table 1; compare ODN 2 to 2a or 3D to 3Da and 3 Db). Stimulation did not appear to result from an antisense mechanism or impurity. ODN caused no detectable to proliferation of 8 or other T cell populations.

Mitogenic ODN sequences uniformly became nonstimulatory if the CpG dinucleotide was mutated (Table 1; compare ODN 1 to 1a; 3D to 3Dc; 3M to 3Ma; and 4 to 4a) or if the cytosine of the CpG dinucleotide was replaced by 5-methylcytosine (Table 1; ODN 1b, 2b, 3Dd, and 3 Mb). Partial methylation of CpG motifs caused a partial loss of stimulatory effect (compare 2a to 2c, Table 1). In contrast, methylation of other cytosines did not reduce ODN activity (ODN 1c, 2d, 3De and 3Mc). These data confirmed that CpG motif is the essential element present in ODN that activate B cells.

In the course of these studies, it became clear that the bases flanking the CpG dinucleotide played an important role in determining the murine B cell activation induced by an ODN. The optimal stimulatory motif was determined to consist of a CpG flanked by two 5' purines (preferably a GpA dinucleotide) and two 3' pyrimidines (preferably a TpT or TpC dinucleotide). Mutations of ODN to bring the CpG motif closer to this ideal improved stimulation (e.g., Table 1, compare ODN 2 to 2e; 3M to 3Md) while mutations that disturbed the motif reduced stimulation (e.g., Table 1, compare ODN 3D to 3Df; 4 to 4b, 4c and 4d). On the other hand, mutations outside the CpG motif did not reduce stimulation (e.g., Table 1, compare ODN to 1d; 3D to 3Dg; 3M to 3Me). For activation of human cells, the best flanking bases are slightly different (See Table 5)).

Of those tested, ODNs shorter than 8 bases were nonstimulatory (e.g., Table 1, ODN 4c). Among the forty-eight 8 base ODN tested, a highly stimulatory sequence was identified as TCAACGTT (SEQ. ID. NO: 90) (ODN4) which contains the self complementary "palindrome" AACGTT (SEQ. ID. NO: 105). In further optimizing this motif, it was found that ODN containing Gs at both ends showed increased stimulation, particularly if the ODN were rendered nuclease resistant by phosphorothioate modification of the terminal internucleotide linkages. ODN 1585 (GGGGTCAACGTTGAGGGGG (SEQ ID NO: 12)), in which the first two and last five internucleotide linkages are phosphorothioate modified caused an average 25.4 fold increase in mouse spleen cell proliferation compared to an average 3.2 fold increase in proliferation included by ODN 1638, which has the same sequence as ODN 1585 except that the 10 Gs at the two ends are replaced by 10 As. The effect of the G-rich ends is cis; addition of an ODN with poly G ends but no CpG motif to cells along with 1638 gave no increased proliferation. For nucleic acid molecules longer than 8 base pairs, non-palindromic motifs containing an unmethylated CpG were found to be more immunostimulatory.

TABLE 1

| ODN | | Sequence (5' to 3')† | Stimulation Index' | |
|---|---|---|---|---|
| | | | $^3$H Uridine | IgM Production |
| 1 | (SEQ ID NO: 89) | GCTAGACGTTAGCGT | 6.1 ± 0.8 | 17.9 ± 3.6 |
| 1a | (SEQ. ID NO: 4) | ......T........ | 1.2 ± 0.2 | 1.7 ± 0.5 |
| 1b | (SEQ ID NO: 13) | ......Z........ | 1.2 ± 0.1 | 1.8 ± 0.0 |
| 1c | (SEQ ID NO: 14) | ............Z.. | 10.3 ± 4.4 | 9.5 ± 1.8 |
| 1d | (SEQ ID NO: 6) | ..AT......GAGC. | 13.0 ± 2.3 | 18.3 ± 7.5 |
| 2 | (SEQ ID NO: 1) | ATGGAAGGTCCAGCGTTCTC | 2.9 ± 0.2 | 13.6 ± 2.0 |
| 2a | (SEQ ID NO: 15) | ..C..CTC..G......... | 7.7 ± 0.8 | 24.2 ± 3.2 |
| 2b | (SEQ ID NO: 16) | ..Z..CTC.ZG..Z...... | 1.6 ± 0.5 | 2.8 ± 2.2 |
| 2c | (SEQ ID NO: 17) | ..Z..CTC..G......... | 3.1 ± 0.6 | 7.3 ± 1.4 |
| 2d | (SEQ ID NO: 18) | ..C..CTC..G......Z.. | 7.4 ± 1.4 | 27.7 ± 5.4 |
| 2e | (SEQ ID NO: 19) | ............A....... | 5.6 ± 2.0 | ND |
| 3D | (SEQ ID NO: 20) | GAGAACGCTGGACCTTCCAT | 4.9 ± 0.5 | 19.9 ± 3.6 |
| 3Da | (SEQ ID NO: 21) | ........C........... | 6.6 ± 1.5 | 33.9 ± 6.8 |
| 3Db | (SEQ ID NO: 22) | ........C......G.... | 10.1 ± 2.8 | 25.4 ± 0.8 |

TABLE 1-continued

| ODN | | Sequence (5' to 3')† | Stimulation Index' | |
|---|---|---|---|---|
| | | | ³H Uridine | IgM Production |
| 3Dc | (SEQ ID NO: 23) | ...C.A........... | 1.0 ± 0.1 | 1.2 ± 0.5 |
| 3Dd | (SEQ ID NO: 24) | .....Z........... | 1.2 ± 0.2 | 1.0 ± 0.4 |
| 3De | (SEQ ID NO: 25) | .........Z....... | 4.4 ± 1.2 | 18.8 ± 4.4 |
| 3Df | (SEQ ID NO: 26) | ......A.......... | 1.6 ± 0.1 | 7.7 ± 0.4 |
| 3Dg | (SEQ ID NO: 27) | ........CC.G.ACTG.. | 6.1 ± 1.5 | 18.6 ± 1.5 |
| 3M | (SEQ ID NO: 28) | TCCATGTCGGTCCTGATGCT | 4.1 ± 0.2 | 23.2 ± 4.9 |
| 3Ma | (SEQ ID NO: 29) | ......CT.......... | 0.9 ± 0.1 | 1.8 ± 0.5 |
| 3Mb | (SEQ ID NO: 30) | .......Z.......... | 1.3 ± 0.3 | 1.5 ± 0.6 |
| 3Mc | (SEQ ID NO: 31) | ..........Z....... | 5.4 ± 1.5 | 8.5 ± 2.6 |
| 3Md | (SEQ ID NO: 7) | ......A..T........ | 17.2 ± 9.4 | ND |
| 3Me | (SEQ ID NO: 32) | ...............C..A. | 3.6 ± 0.2 | 14.2 ± 5.2 |
| 4 | (SEQ ID NO: 90) | TCAACGTT | 6.1 ± 1.4 | 19.2 ± 5.2 |
| 4a | (SEQ ID NO: 91) | ....GC.. | 1.1 ± 0.2 | 1.5 ± 1.1 |
| 4b | (SEQ ID NO: 92) | ...GCGC. | 4.5 ± 0.2 | 9.6 ± 3.4 |
| 4c | (SEQ ID NO: 93) | ...TCGA. | 2.7 ± 1.0 | ND |
| 4d | (SEQ ID NO: 94) | ..TT..AA | 1.3 ± 0.2 | ND |
| 4e | (Residue 2-8 of SEQ ID NO: 90, SEQ ID 106) | -....... | 1.3 ± 0.2 | 1.1 ± 0.5 |
| 4f | (SEQ ID NO: 95) | C....... | 3.9 ± 1.4 | ND |
| 4g | (Residue 11-18 of SEQ ID NO: 19, Seq ID 117) | --......CT | 1.4 ± 0.3 | ND |
| 4h | (SEQ ID NO: 96) | ......C | 1.2 ± 0.2 | ND |

Stimulation indexes are the means and std. dev. derived from at least 3 separate experiments, and are compared to wells cultured with no added ODN.
ND = not done.
CpG dinucleotides are underlined.
Dots indicate identity; dashes indicate deletions.
Z = 5 methyl cytosine.

TABLE 2

Identification of the optimal CpG motif for Murine IL-6 production and B cell activation.

| ODN | | SEQUENCE (5'-3') | IL-6 (pg/ml)[a] | | SI[b] | IgM (ng/ml)[c] |
|---|---|---|---|---|---|---|
| | | | CH12.LX | SPLENIC B CELL | | |
| 512 | (SEQ ID No: 28) | TCCATGTCGGTCCTGATGCT | 1300 ± 106 | 627 ± 43 | 5.8 ± 0.3 | 7315 ± 1324 |
| 1637 | (SEQ ID No: 33) | ......C............. | 136 ± 27 | 46 ± 6 | 1.7 ± 0.2 | 770 ± 72 |
| 1615 | (SEQ ID No: 34) | ......G............. | 1201 ± 155 | 850 ± 202 | 3.7 ± 0.3 | 3212 ± 617 |
| 1614 | (SEQ ID No: 35) | ......A............. | 1533 ± 321 | 1812 ± 103 | 10.8 ± 0.6 | 7558 ± 414 |
| 1636 | (SEQ ID No: 36) | ........A........... | 1181 ± 76 | 947 ± 132 | 5.4 ± 0.4 | 3983 ± 485 |
| 1634 | (SEQ ID No: 37) | .........C.......... | 1049 ± 223 | 1671 ± 175 | 9.2 ± 0.9 | 6256 ± 261 |
| 1619 | (SEQ ID No: 38) | .........T.......... | 1555 ± 304 | 2908 ± 129 | 12.5 ± 1.0 | 8243 ± 698 |

TABLE 2-continued

Identification of the optimal CpG motif for Murine IL-6 production and B cell activation.

| ODN | SEQUENCE (5'-3') | IL-6 (pg/ml)[a] CH12.LX | SPLENIC B CELL | SI[b] | IgM (ng/ml)[c] |
|---|---|---|---|---|---|
| 1618 (SEQ ID No: 7) | ......A...T.......... | 2109 ± 291 | 2596 ± 166 | 12.9 ± 0.7 | 10425 ± 674 |
| 1639 (SEQ ID No: 3) | .....AA...T.......... | 1827 ± 83 | 2012 ± 132 | 11.5 ± 0.4 | 9489 ± 103 |
| 1707 (SEQ ID No: 39) | ......A...TC......... | ND | 1147 ± 175 | 4.0 ± 0.2 | 3534 ± 217 |
| 1708 (SEQ ID No: 40) | .....CA...TG......... | ND | 59 ± 3 | 1.5 ± 0.1 | 466 ± 109 |

Dots indicate identity; CpG dinucleotides are underlined; ND = not done
[a]The experiment was done at least three times with similar results. The level of IL-6 of unstimulated control culture of both CH12.LX and splenic B cells was ≦ 10 pg/ml. The IgM level of unstimulated culture was 547 ± 82 ng/mL. CpG dinucleotides are underlined and dots indicate identity.
[b][$^3$H] Uridine uptake was indicated as a fold increase (SI: stimulation index) from unstimulated control (2322.67 ± 213.68 cpm). Cells were stimulated with 20 µM of various CpG O-ODN. Data present the mean ± SD of triplicates
[c]Measured by ELISA.

Other octamer ODN containing a 6 base palindrome with a TpC dinucleotide at the 5' end were also active (e.g., Table 1, ODN 4b, 4c). Other dinucleotides at the 5' end gave reduced stimulation (e.g., ODN 4f; all sixteen possible dinucleotides were tested). The presence of a 3' dinucleotide was insufficient to compensate for the lack of a 5' dinucleotide (e.g., Table 1, ODN 4g). Disruption of the palindrome eliminated stimulation in octamer ODN (e.g., Table 1, ODN 4h), but palindromes were not required in longer ODN.

The kinetics of lymphocyte activation were investigated using mouse spleen cells. When the cells were pulsed at the same time as ODN addition and harvested just four hours later, there was already a two-fold increase in $^3$H uridine incorporation. Stimulation peaked at 12-48 hours and then decreased. After 24 hours, no intact ODN were detected, perhaps accounting for the subsequent fall in stimulation when purified B cells with or without anti-IgM (at a submitogenic dose) were cultured with CpG ODN, proliferation was found to synergistically increase about 10-fold by the two mitogens in combination after 48 hours. The magnitude of stimulation was concentration dependent and consistently exceeded that of LPS under optimal conditions for both. Oligonucleotides containing a nuclease resistant phosphorothioate backbone were approximately two hundred times more potent than unmodified oligonucleotides.

Cell cycle analysis was used to determine the proportion of B cells activated by CpG-ODN. CpG-ODN induced cycling in more than 95% of B cells. Splenic B lymphocytes sorted by flow cytometry into CD23- (marginal zone) and CD23+ (follicular) subpopulations were equally responsive to ODN-induced stimulation, as were both resting and activated populations of B cells isolated by fractionation over Percoll gradients. These studies demonstrated that CpG-ODN induced essentially all B cells to enter the cell cycle.

Immunostimulatory Nucleic Acid Molecules Block Murine B Cell Apoptosis

Certain B cell lines, such as WEHI-231, are induced to undergo growth arrest and/or apoptosis in response to crosslinking of their antigen receptor by anti-IgM (Jakway, J. P. et al., "Growth regulation of the B lymphoma cell line WEHI-231 by anti-immunoglobulin, lipopolysaccharide and other bacterial products" J. Immunol. 137: 2225 (1986); Tsubata, T., J. Wu and T. Flonjo: B-cell apoptosis induced yb antigen receptor crosslinking is blocked by a T-cell signal through CD40." Nature 365: 645 (1993)). WEHI-231 cells are rescued from this growth arrest by certain stimuli such as LPS and by the CD40 ligand. ODN containing the CpG motif were also found to protect WEHI-231 from anti-IgM induced growth arrest, indicating that accessory cell populations are not required for the effect. Subsequent work indicates that CpG ODN induce Bcl-x and myc expression, which may account for the protection from apoptosis. Also, CpG nucleic acids have been found to block apoptosis in human cells. This inhibition of apoptosis is important, since it should enhance and prolong immune activation by CpG DNA.

Identification of the Optimal CpG Motif for Induction of Murine IL-6 and IgM Secretion and B Cell Proliferation To evaluate whether the optimal B cell stimulatory CpG motif was identical with the optimal CpG motif for IL-6 secretion, a panel of ODN in which the bases flanking the CpG dinucleotide were progressively substituted was studied. This ODN panel was analyzed for effects on B cell proliferation, Ig production, and IL-6 secretion, using both splenic B cells and CH12.LX cells. As shown in Table 2, the optimal stimulatory motif contains an unmethylated CpG flanked by two 5' purines and two 3' pyrimidines. Generally a mutation of either 5' purines to C were especially deleterious, but changes in 5' purines to T or 3' pyrimidines to purines had less marked effects. Based on analyses of these and scores of other ODN, it was determined that the optimal CpG motif for induction of IL-6 secretion is TGACGTT (SEQ. ID. NO: 108), which is identical with the optimal mitogenic and IgM-inducing CpG motif (Table 2). This motif was more stimulatory than any of the palindrome containing sequences studied (1639, 1707 and 1708).

Induction of Murine Cytokine Secretion by CpG motifs in Bacterial DNA or Oligonucleotides.

As described in Example 9, the amount of IL-6 secreted by spleen cells after CpG DNA stimulation was measured by ELISA. T cell depleted spleen cell cultures rather than whole spleen cells were used for in vitro studies following preliminary studies showing that T cells contribute little or nothing to the IL-6 produced by CpG DNA-stimulated spleen cells. As shown in Table 3, IL-6 production was markedly increased in cells cultured with E. coli DNA but not in cells cultured with calf thymus DNA. To confirm that the increased IL-6 production observed with E. coli DNA was not de to contamination by other bacterial products, the DNA was digested with DNAse prior to analysis. DNAse pretreatment abolished IL-6 production induced by E. coli DNA (Table 3). In addition, spleen cells from LPS-nonresponsive C2H/HeJ mouse produced similar levels of IL-6 in response to bacterial DNA. To analyze whether the IL-6 secretion induced by E. coli DNA was mediated by the unmethylated CpG dinucleotides in bacterial DNA, methylated E. coli DNA and a panel of synthetic ODN were examined. As shown in Table 3, CpG ODN significantly induced IL-6 secretion (ODN 5a, 5b, 5c) while CpG methylated *E. coli* DNA, or ODN containing methylated CpG (ODN 5f) or no CpG (ODN 5d) did not. Changes at sites other than CpG dinucleotides (ODN 5b) or methylation of other cytosines (ODN 5g) did not reduce the effect of CpG ODN. Methylation of a single CpG in an ODN with three CpGs resulted in a partial reduction in the stimulation (compare ODN 5c to 5e; Table 3).

TABLE 3

Induction of Murine IL-6 secretion by CpG motifs in bacterial DNA or oligonucleotides.

| Treatment | IL-6 (pg/ml) |
|---|---|
| calf thymus DNA | ≤10 |
| calf thymus DNA + DNase | ≤10 |
| *E. coli* DNA | 1169.5 ± 94.1 |
| *E. coli* DNA + DNase | ≤10 |
| CpG methylated *E. coli* DNA | ≤10 |
| LPS | 280.1 ± 17.1 |
| Media (no DNA) | ≤10 |

| ODN | | | | |
|---|---|---|---|---|
| 5a | SEQ. ID. No: 115 | ATGGACTCTCCAGCGTTCTC | 1096.4 ± 372.0 |
| 5b | SEQ. ID. No: 19 | .....AGG....A........ | 1124.5 ± 126.2 |
| 5c | SEQ. ID. No: 15 | ..C.......G.......... | 1783.0 ± 189.5 |
| 5d | SEQ. ID. No: 114 | .....AGG..C...T...... | ≤10 |
| 5e | SEQ. ID. No: 116 | ..C.......G...Z...... | 851.1 ± 114.4 |
| 5f | SEQ. ID. No: 16 | ..Z.......ZG..Z...... | ≤10 |
| 5g | SEQ. ID. No: 18 | ..C.......G......Z... | 1862.3 ± 87.26 |

T cell depleted spleen cells from DBA/2 mice were stimulated with phosphodiester modified oligonucleotides (O-ODN) (20 µM), calf thymus DNA (50 µg/ml) or *E. coli* DNA (50 µg/ml) with or without enzyme treatment, or LPS (10 µg/ml) for 24 hr. Data represent the mean (pg/ml) ± SD of triplicates. CpG dinucleotides are underlined and dots indicate identity. Z indicates 5-methylcytosine.

CpG Motifs can be Used as an Artificial Adjuvant.

Nonspecific simulators of the immune response are known as adjuvants. The use of adjuvants is essential to induce a strong antibody response to soluble antigens (Harlow and Lan, *Antibodies: A Laboratory manual*, Cold Spring harbor, N.Y. Current Edition; hereby incorporated by reference). The overall effect of adjuvants is dramatic and their importance cannot be overemphasized. The action of an adjuvant allows much smaller doses of antigen to be used and generates antibody responses that are more persistent. The nonspecific activation of the immune response often can spell the difference between success and failure in obtaining an immune response. Adjuvants should be used for first injections unless there is some very specific reason to avoid this. Most adjuvants incorporate two components. One component is designed to protect the antigen from rapid catabolism (e.g., liposomes or synthetic surfactants (Hunter et al. 1981)). Liposomes are only effective when the immunogen is incorporated into the outer lipid layer; entrapped molecules are not seen by the immune system. The other component is a substance that will stimulate the immune response nonspecifically. These substances act by raising the level of lymphokines. Lymphokines stimulate the activity of antigen-processing cells directly and cause a local inflammatory reaction at the site of injection. Early work relied entirely on heat-killed bacteria (Dienes 1936) or lipopolysaccharide (LPS) (Johnson et al. 1956). LPS is reasonably toxic, and, through analysis of its structural components, most of its properties as an adjuvant have been shown to be in a portion known as lipid A. Lipid A is available in a number of synthetic and natural forms that are much less toxic than LPS, but still retains most of the better adjuvant properties of parental LPS molecule. Lipid A compounds are often delivered using liposomes.

Recently an intense drive to find potent adjuvants with more acceptable side effects has led to the production of new synthetic adjuvants. The present invention provides the sequence 1826 TCCATGACGTTCCTGACGTT (SEQ ID NO: 10), which is an adjuvant including CpG containing nucleic acids. The sequence is a strong immune activating sequence and is a superb adjuvant, with efficacy comparable or superior to complete Freund's but without apparent toxicity.

Titration of Induction of Murine IL-6 Secretion by CpG Motifs

Figure 1B:
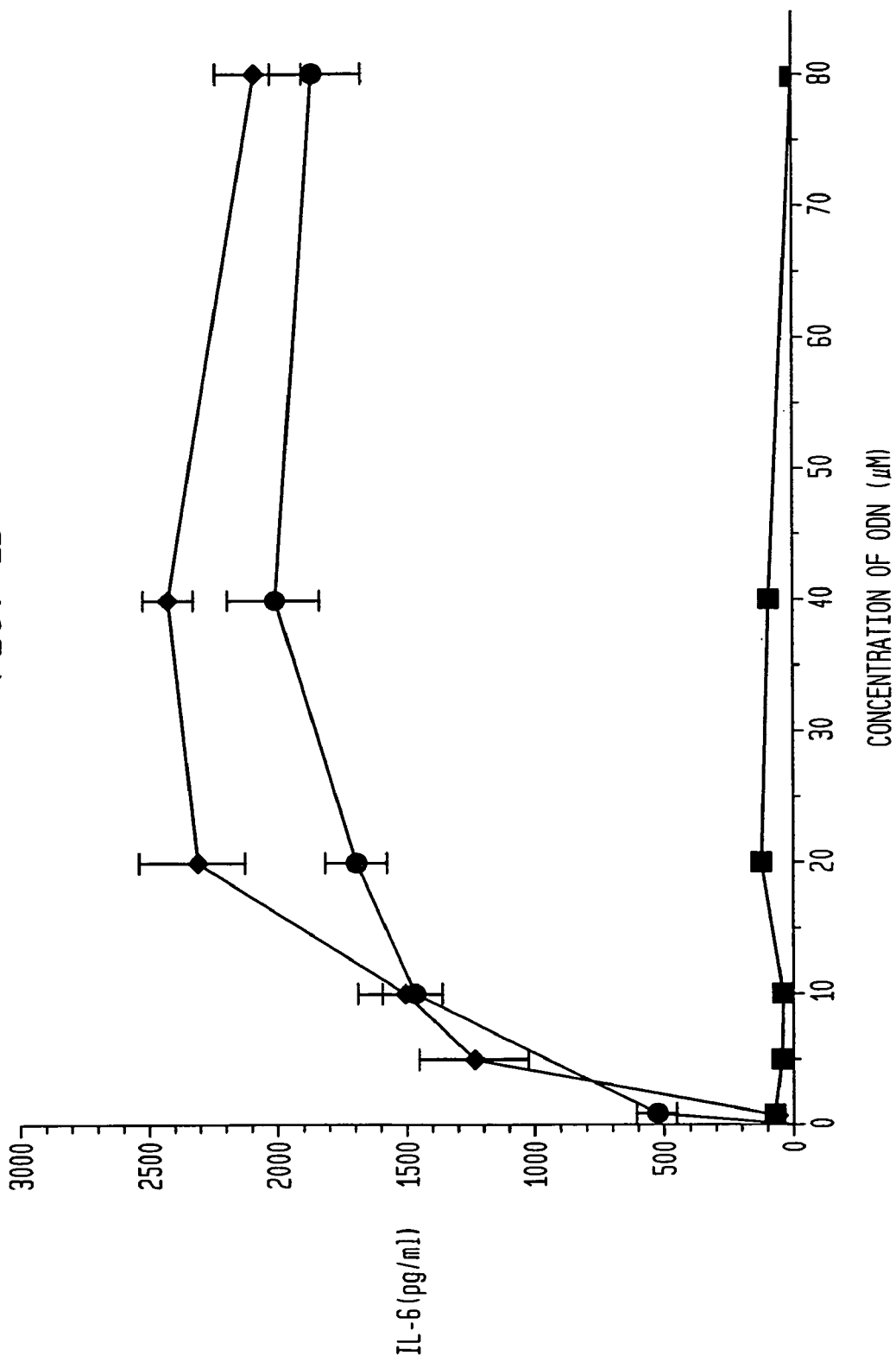
Figure 1C:
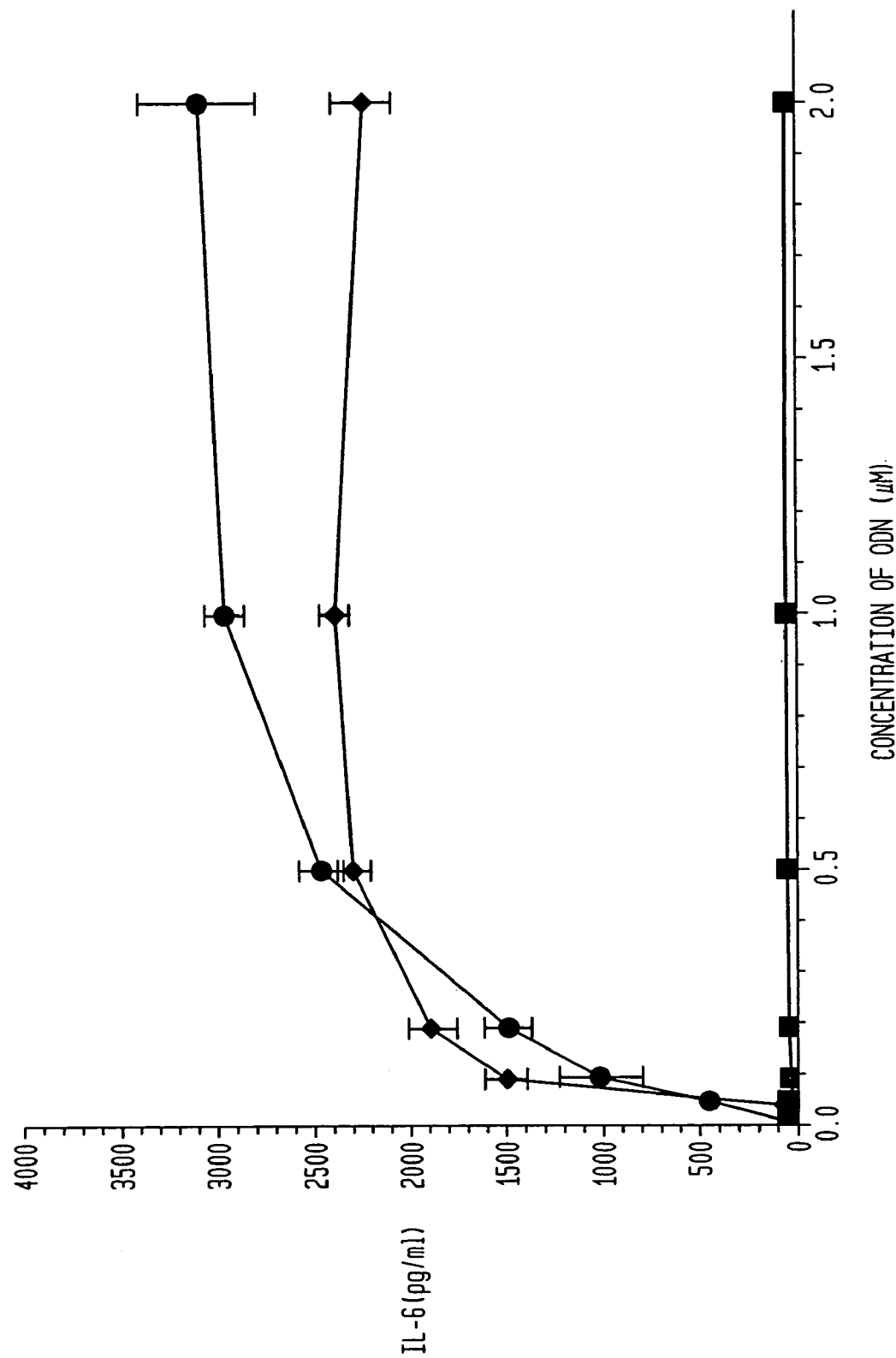

Bacterial DNA and CpG ODN induced IL-6 production in T cell depleted murine spleen cells in a dose-dependent manner, but vertebrate DNA and non-CpG ODN did not (FIG. 1). IL-6 production plateaued at approximately 50 µg/ml of bacterial DNA or 40 µM of CpG O-ODN. The maximum levels of IL-6 induced by bacterial DNA and CpG ODN were 1-1.5 ng/ml and 2-4 ng/ml respectively. These levels were significantly greater than those seen-after stimulation by LPS (0.35 ng/ml) (FIG. 1A). To evaluate whether CpG ODN with a nuclease-resistant DNA backbone would also induce IL-6 production, S-ODN were added to T cell depleted murine spleen cells. CpG S-ODN also induced IL-6 production in a dose-dependent manner to approximately the same level as CpG O-ODN while non-CpG S-ODN failed to induce IL-6 (FIG. 1C). CpG S-ODN at a concentration of 0.05 µM could induce maximal IL-6 production in these cells. This result indicated that the nuclease-resistant DNA backbone modification retains the sequence specific ability of CpG DNA to induce IL-6 secretion and that CpG S-ODN are more than 80-fold more potent than CpG O-ODN in this assay system.

Induction of Murine IL-6 Secretion by CpG DNA In Vivo

To evaluate the ability of bacterial DNA and CpG S-ODN to induce Il-6 secretion in vivo, BALB/c mice were injected iv. with 100 μg of *E. coli* DNA, calf thymus DNA, or CpG or non-stimulatory S-ODN and bled 2 hr after stimulation. The level of IL-6 in the sera from the *E. coli* DNA injected group was approximately 13 ng/ml while IL-6 was not detected in the sera from calf thymus DNA or PBS injected groups (Table 4). CpG S-ODN also induced IL-6 secretion in vivo. The IL-6 level in the sera from CpG S-ODN injected groups was approximately 20 ng/ml. In contrast, IL-6 was not detected in the sera from non-stimulatory S-ODN stimulated group (Table 4).

TABLE 4

Secretion of Murine IL-6 induced by CpG DNA stimulation in vivo.

| Stimulant | IL-6 (pg/ml) |
|---|---|
| PBS | <50 |
| *E. coli* DNA | 13858 ± 3143 |
| Calf Thymus DNA | <50 |
| CpG S-ODN | 20715 ± 606 |
| non-CpG S-ODN | <50 |

Mice (2 mice/group) were i.v. injected with 100 μl of PBS, 200 μg of *E. coli* DNA or calf thymus DNA, or 500 μg of CpG S-ODN or non-CpG control S-ODN. Mice were bled 2 hr after injection and 1:10 dilution of each serum was analyzed by IL-6 ELISA. Sensitivity limit of IL-6 ELISA was 5 pg/ml. Sequences of the CpG S-ODN is 5'GCATGACGTTGAGCT3' (SEQ. ID. No: 6) and of the non-stimulatory S-ODN is 5'GCTAGATGTTAGCGT3' (SEQ. ID. No: 4). Note that although there is a CpG in sequence 48, it is too close to the 3' end to effect stimulation, as explained herein. Data represent mean ± SD of duplicates. The experiment was done at least twice with similar results.

Kinetics of Murine Il-6 Secretion after Stimulation by CpG Motifs In Vivo

Figure 2:
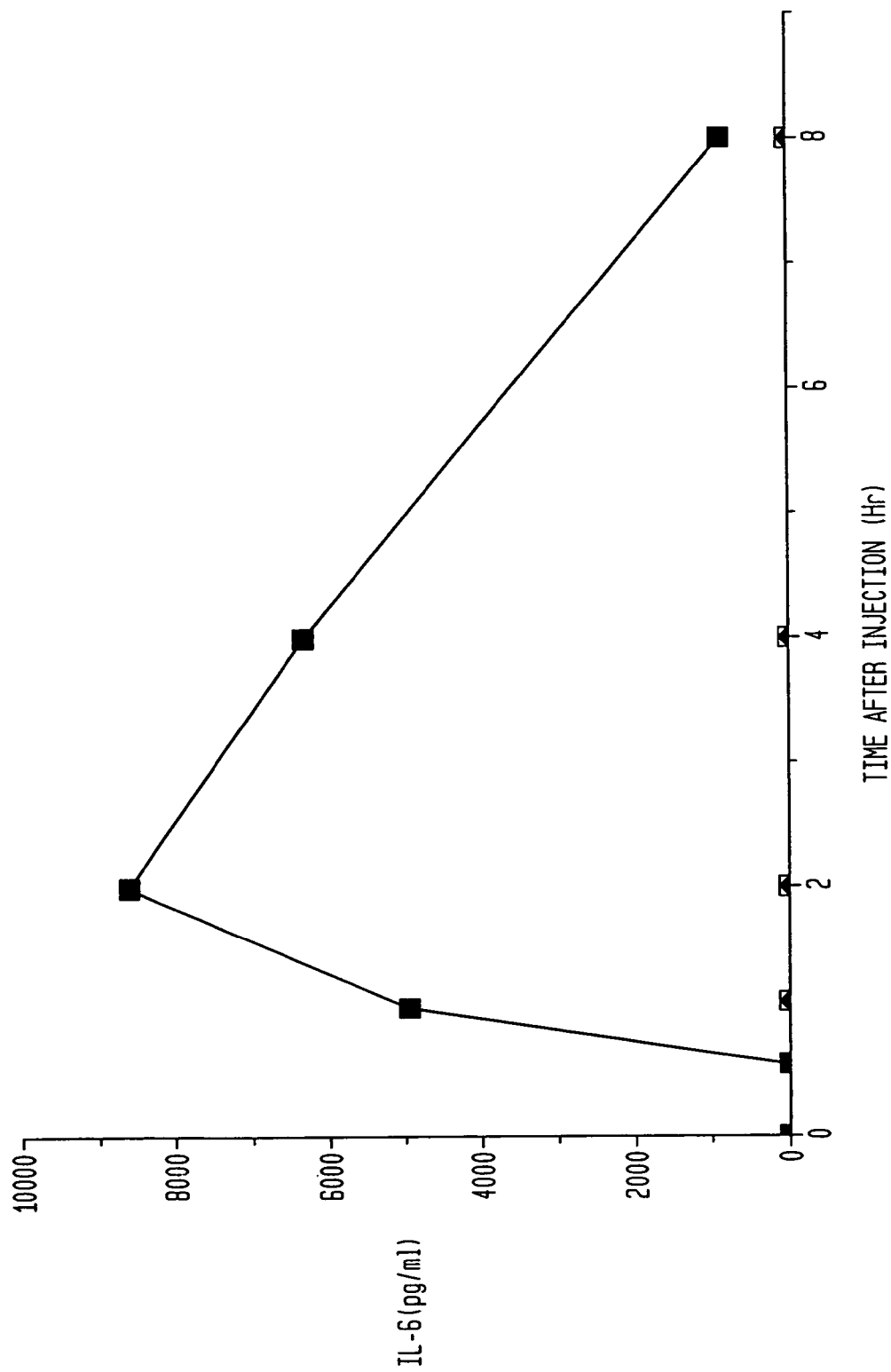

To evaluate the kinetics of induction of IL-6 secretion by CpG DNA n vivo, BALB/c mice were injected iv. with CpG or control non-CpG S-ODN. Serum IL-6 levels were significantly increased within 1 hr and peaked at 2 hr to a level of approximately 9 ng/ml in the CpG S-ODN injected group (FIG. 2). Il-6 protein in sera rapidly decreased after 4 hr and returned to basal level by 12 hr after stimulation. In contrast to CpG DNA stimulated groups, no significant increase of IL-6 was observed in the sera from the non-stimulatory S-ODN or PBS injected groups (FIG. 2).

Tissue Distribution and Kinetics of IL-6, mRNA Expression Induced by CpG Motifs In Vivo As shown in FIG. 2, the level of serum IL-6 increased rapidly after CpG DNA stimulation. To investigate the possible tissue origin of this serum IL-6, and the kinetics of IL-6 gene expression in vivo after CpG DNA stimulation, BALB/c mice were injected iv with CpG or non-CpG S-ODN and RNA was extracted from liver, spleen, thymus, and bone marrow at various time points after stimulation. As shown in FIG. 3A, the level of IL-6 mRNA in liver, spleen, and thymus was increased within 30 min. after injection of CpG S-ODN. The liver IL-6 mRNA peaked at 2 hr post-injection and rapidly decreased and reached basal level 8 hr after stimulation (FIG. 3A). Splenic IL-6 mRNA peaked at 2 hr after stimulation and then gradually decreased (FIG. 3A). Thymus IL-6 mRNA peaked at 1 hr post-injection and then gradually decreased (FIG. 3A). IL-6 mRNA was significantly increased in bone marrow within 1 hr after CpG S-ODN injection but then returned to basal level. In response to CpG S-ODN, liver, spleen and thymus showed more substantial increases in IL-6 mRNA expression than the bone marrow.

Patterns of Murine Cytokine Expression Induced by CpG DNA

In vivo or in whole spleen cells, no significant increase in the protein levels of the following interleukins: IL-2, IL-3, IL-4, IL-5, or IL-10 was detected within the first six hours (Klinman, D. M. et al., (1996) *Proc. Natl. Acad. Sci. USA* 93:2879-2883). However, the level of TNF-α is increased within 30 minutes and the level of IL-6 increased strikingly within 2 hours in the serum of mice injected with CpG ODN. Increased expression of IL-12 and interferon gamma (IFN-γ) mRNA by spleen cells was also detected within the first two hours

TABLE 5

| ODN | Sequence (5'-3') | $IL-6_1$ | $TNF-_{\alpha 1}$ | $IFN-_{\gamma 1}$ | GM-CSF | IL-12 |
|---|---|---|---|---|---|---|
| 512 SEQ ID NO: 28 | TCCATGTCGGTCCTGATGCT | 500 | 140 | 15.6 | 70 | 250 |
| 1637 SEQ ID NO: 33 | ......C............ | 550 | 16 | 7.8 | 15.6 | 16 |
| 1615 SEQ ID NO: 34 | ......G............ | 600 | 145 | 7.8 | 45 | 145 |
| 1614 SEQ ID NO: 35 | ......A............ | 550 | 31 | 0 | 50 | 31 |
| 1636 SEQ ID NO: 36 | ........A.......... | 325 | 250 | 35 | 40 | 250 |
| 1634 SEQ ID NO: 37 | ........C.......... | 300 | 400 | 40 | 85 | 400 |
| 1619 SEQ ID NO: 38 | ........T.......... | 275 | 450 | 200 | 80 | 450 |
| 1618 SEQ ID NO: 7 | ......A..T......... | 300 | 60 | 15.6 | 15.6 | 62 |
| 1639 SEQ ID NO: 3 | .....AA..T......... | 625 | 220 | 15.6 | 40 | 220 |

TABLE 5-continued

| ODN | Sequence (5'-3') | IL-6₁ | TNF-α1 | IFN-γ1 | GM-CSF | IL-12 |
|---|---|---|---|---|---|---|
| 1707 SEQ ID NO: 39 | ......A...TC......... | 300 | 70 | 17 | 0 | 70 |
| 1708 SEQ ID NO: 40 | .....CA...TG......... | 270 | 10 | 17 | ND | 10 | dots indicate identity; CpG dinucleotides are underlined
[1]measured by ELISA using Quantikine kits from R&D Systems (pg/ml) Cells were cultured in 10% autologous serum with the indicated oligodeoxynucleotides (12 µg/ml) for 4 hr in the case of TNF-α or 24 hr for the other cytokines before supernatant harvest and assay. Data are presented as the level of cytokine above that in wells with no added oligodeoxynucleotide.

CpG DNA Induces Cytokine Secretion by Human PBMC, Specifically Monocytes

The same panels of ODN used for studying mouse cytokine expression were used to determine whether human cells also are induced by CpG motifs to express cytokine (or proliferate), and to identify the CpG motif(s) responsible. Oligonucleotide 1619 (GTCGTT; SEQ. ID. NO: 57) was the best inducer of TNF-α and IFN-γ secretion, and was closely followed by a nearly identical motif in oligonucleotide 1634 (GTCGCT; SEQ. ID. NO: 58) (Table 5). The motifs in oligodeoxynucleotides 1637 and 1614 (GCCGGT; SEQ. ID. NO: 109) and (GACGGT; SEQ. ID. NO: 110) led to strong IL-6 secretion with relatively little induction of other cytokines. Thus, it appears that human lymphocytes, like murine lymphocytes, secrete cytokines differentially in response to CpG dinucleotides, depending on the surrounding bases. Moreover, the motifs that stimulate murine cells best differ from those that are most effective with human cells. Certain CpG oligodeoxynucleotides are poor at activating human cells (oligodeoxynucleotides 1707, 1708, which contain the palindrome forming sequences GACGTC (SEQ. ID. NO: 111) and CACGTG (SEQ. ID. NO: 112) respectively).

The cells responding to the DNA appear to be monocytes, since the cytokine secretion is abolished by treatment of the cells with L-leucyl-L-leucine methyl ester (L-LME), which is selectively toxic to monocytes (but also to cytotoxic T lymphocytes and NK cells), and does not affect B cell Ig secretion (Table 6). The cells surviving L-LME treatment had >95% viability by trypan blue exclusion, indicating that the lack of a cytokine response among these cells did not simply reflect a nonspecific death of all cell types. Cytokine secretion in response to E. coli (EC) DNA requires unmethylated CpG motifs, since it is abolished by methylation of the EC DNA (next to the bottom row, Table 6). LPS contamination of the DNA cannot explain the results since the level of contamination was identical in the native and methylated DNA, and since addition of twice the highest amount of contaminating LPS had no effect (not shown).

TABLE 6

CpG DNA induces cytokine secretion by human PBMC

| DNA | TNF-α (pg/ml)[1] | IL-6 (pg/ml) | IFN-γ (pg/ml) | RANTES (pg/ml) |
|---|---|---|---|---|
| EC DNA (50 µg/ml) | 900 | 12,000 | 700 | 1560 |
| EC DNA (5 µg/ml) | 850 | 11,000 | 400 | 750 |
| EC DNA (0.5 µg/ml) | 500 | ND | 200 | 0 |
| EC DNA (0.05 µg/ml) | 62.5 | 10,000 | 15.6 | 0 |
| EC DNA (50 µg/ml) + L-LME₂ | 0 | ND | ND | ND |
| EC DNA (10 µg/ml) Methyl.₃ | 0 | 5 | ND | ND |
| CT DNA (50 µg/ml) | 0 | 600 | 0 | 0 |

[1]Levels of all cytokines were determined by ELISA using Quantikine kits from R&D Systems as described in the previous table. Results are representative using PBMC from different donors.
₂Cells were pretreated for 15 min. with L-leucyl-L-leucine methyl ester (M-LME) to determine whether the cytokine production under these conditions was from monocytes (or other L-LME-sensitive cells).
₃EC DNA was methylated using 2 U/µg DNA of CpG methylase (New England Biolabs) according to the manufacturer's directions, and methylation confirmed by digestion with Hpa-II and Msp-I. As a negative control, samples were included containing twice the maximal amount of LPS contained in the highest concentration of EC DNA which failed to induce detectable cytokine production under these experimental conditions.
ND = not done The loss of cytokine production in the PBMC treated with L-LME suggested that monocytes may be responsible for cytokine production in response to CpG DNA. To test this hypothesis more directly, the effects of CpG DNA on highly purified human monocytes and macrophages was tested. As hypothesized, CpG DNA directly activated production of the cytokines IL-6, GM-CSF, and TNF-α by human macrophages, whereas non-CpG DNA did not (Table 7).

TABLE 7

CpG DNA induces cytokine expression in purified human macrophages

| | IL-6 (pg/ml) | GM-CSF (pg/ml) | TNF-α (pg/ml) |
|---|---|---|---|
| Cells alone | 0 | 0 | 0 |
| CT DNA (50 µg/ml) | 0 | 0 | 0 |
| EC DNA (50 µg/ml) | 2000 | 15.6 | 1000 |

Figure 4A:
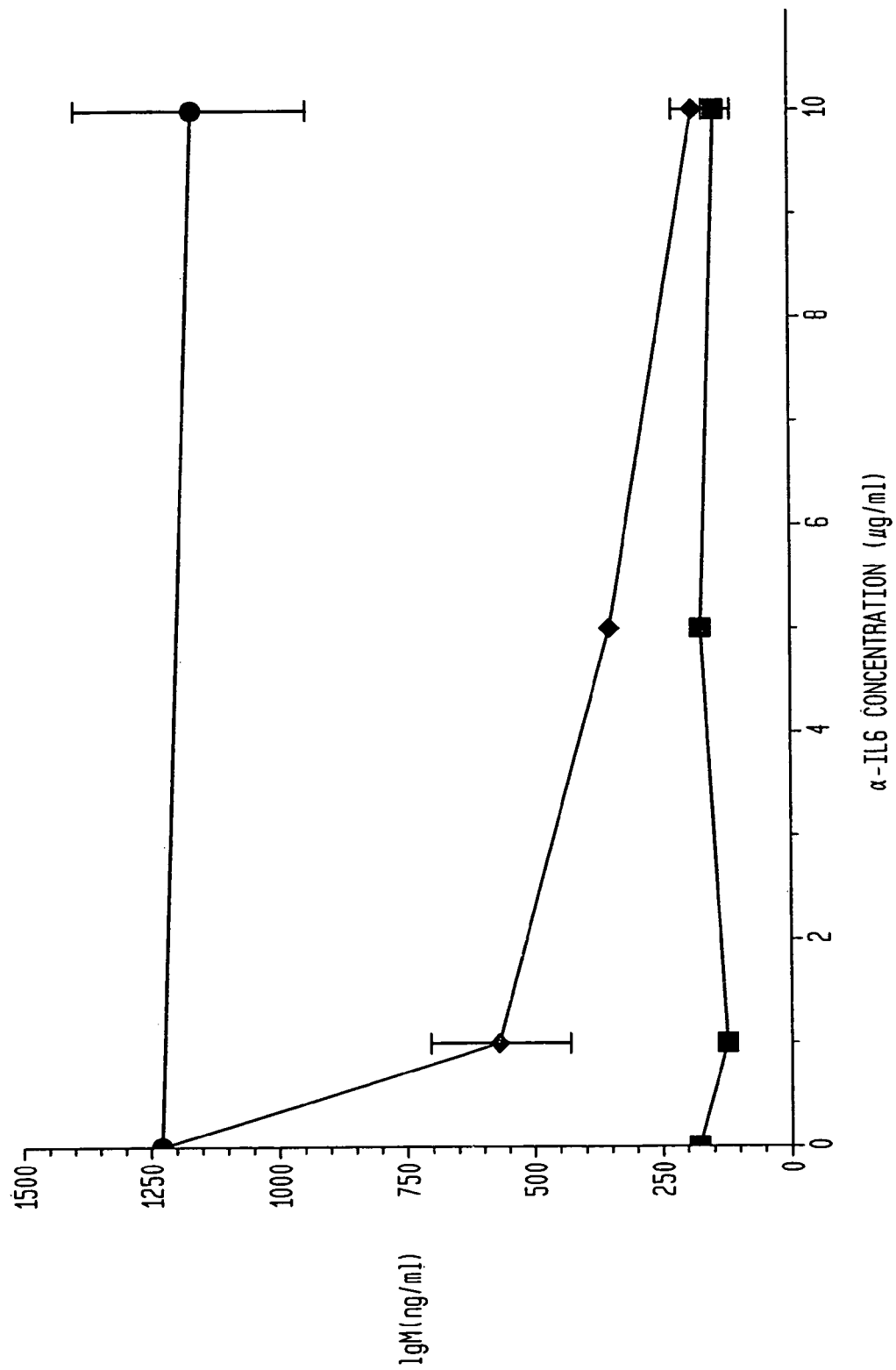
Figure 4B:
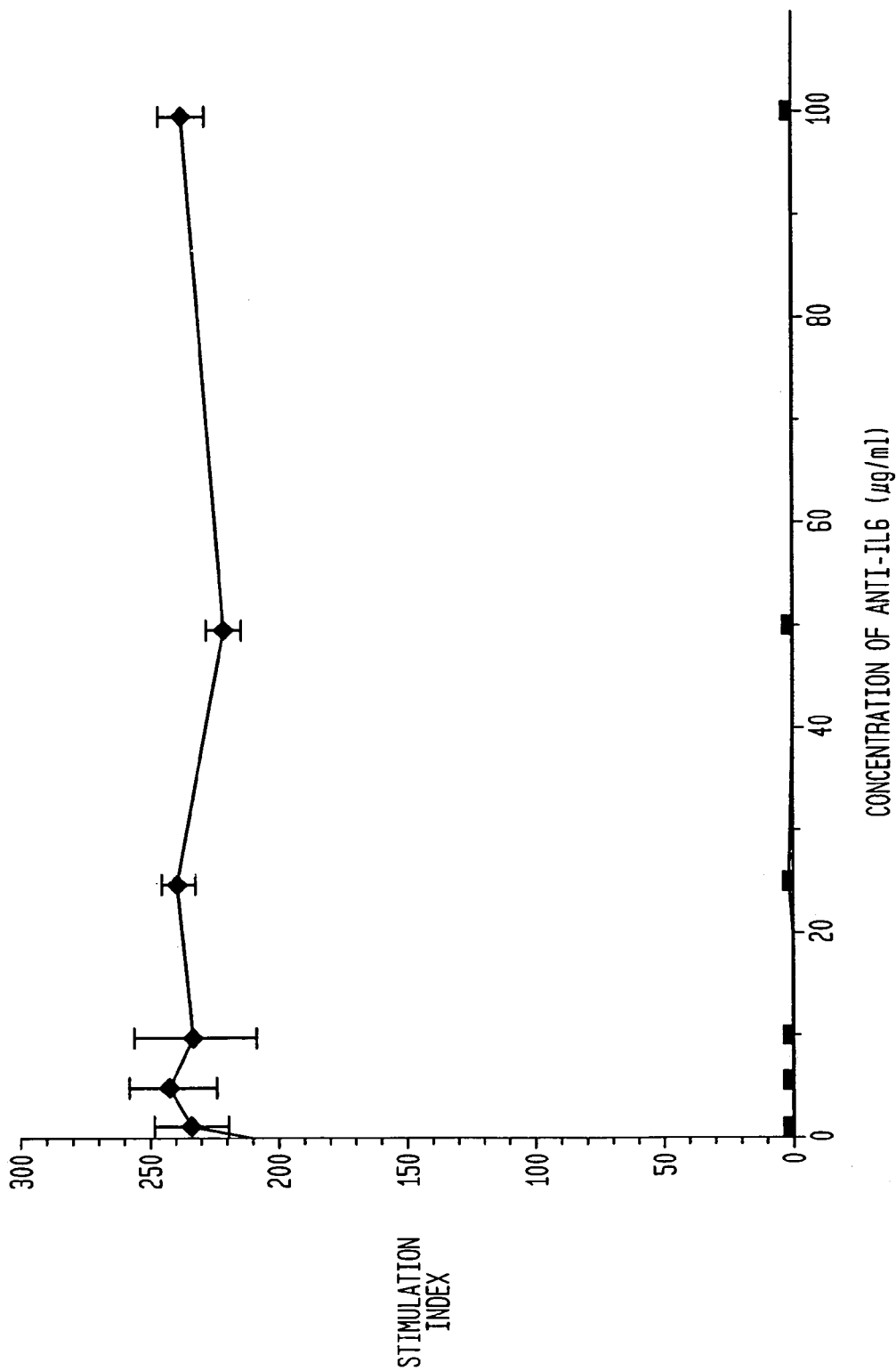

Biological Role of IL-6 in inducing Murine IgM Production in Response to CpG Motifs The kinetic studies described above revealed that induction of IL-6 secretion, which occurs within 1 hr post CpG stimulation, precedes IgM secretion. Since the optimal CpG motif for ODN inducing secretion of IL-6 is the same as that for IgM (Table 2), whether the CpG motifs independently induce IgM and IL-6 production or whether the IgM production is dependent on prior IL-6 secretion was examined. The addition of neutralizing anti-IL-6 antibodies inhibited in vitro IgM production mediated by CpG ODN in a dose-dependent manner but a control antibody did not (FIG. 4A). In contrast, anti-IL-6 addition did not affect either the basal level or the CpG-induced B cell proliferation (FIG. 4B).

Increased Transcriptional Activity of the Il-6 Promoter in Response to CpG DNA

Figure 5:
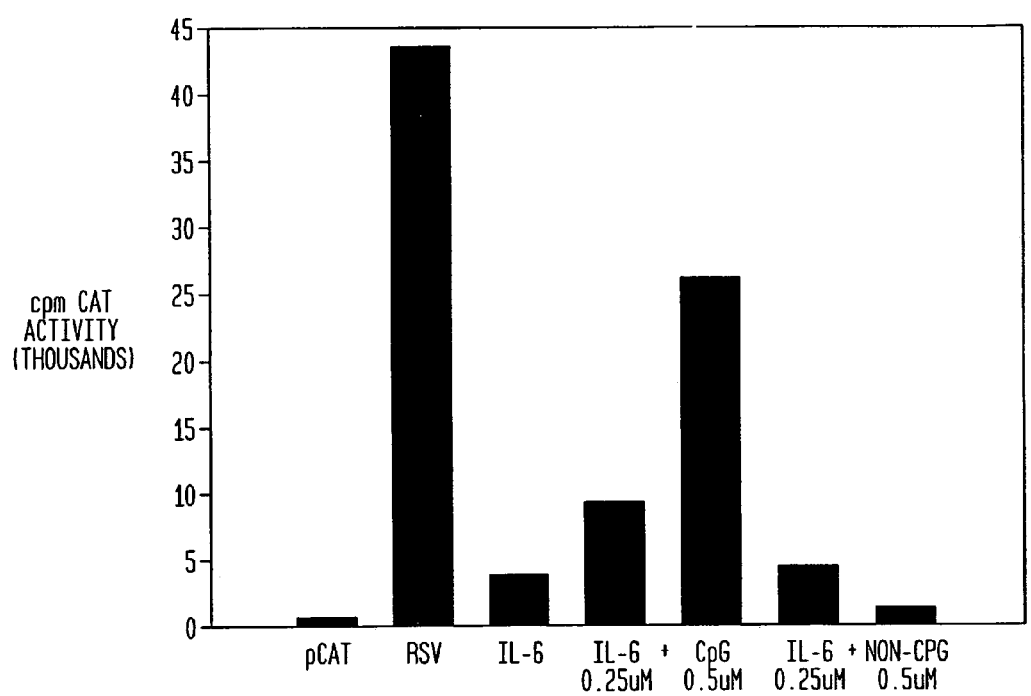

The increased level of IL-6 mRNA and protein after CpG DNA stimulation could result from transcriptional or post-transcriptional regulation. To determine if the transcriptional activity of the IL-6 promoter was unregulated in B cells cultured with CpG ODN, a murine B cell line, WEHI-231, which produces IL-6 in response to CpG DNA, was transfected with an IL-6 promoter-CAT construct (pIL-6/CAT) (Pottrats, S. T. et al., 17B-estradiol) inhibits expression of a human interleukin-6-promoter-reporter constructs by a receptor-dependent mechanism. *J. Clin. Invest.* 93:944). CAT assays were performed after stimulation with various concentrations of CpG or non-CpG ODN. As shown in FIG. 5, CpG ODN induced increased CAT activity in dose-dependent manner while non-CPG ODN failed to induce CAT activity. This confirms that CpG induces the transcriptional activity of the IL-6 promoter.

Dependence of B cell Activation by CpG ODN on the Number of 5' and 3' Phosphorothioate Internucleotide Linkages To determine whether partial sulfur modification of the ODN backbone would be sufficient to enhance B cell activation, the effects of a series of ODN with the same sequence, but with differing numbers of S internucleotide linkages at the 5' end of ODN were required to provide optimal protection of the ODN from degradation by intracellular exo- and endo-nucleases. Only chimeric ODN containing two 5' phosphorothioate-modified linkages, and a variable number of 3' modified linkages were therefore examined.

The lymphocyte stimulating effects of these ODN were tested at three concentrations (3.3, 10, and 30 µM) by measuring the total levels of RNA synthesis (by $^3$H uridine incorporation) or DNA synthesis (by $^3$H thymidine incorporation) in treated spleen cell cultures (Example 10). O-ODN (0/0 phosphorothioate modifications) bearing a CpG motif caused no spleen cell stimulation unless added to the cultures at concentrations of at least 10 µM (Example 10). However, when this sequence was modified with two S linkages at the 5' end and at least three S linkages at the 3' end, significant stimulation was seen at a dose of 3.3 µM. At this low dose, the level of stimulation showed a progressive increase as the number of 3' modified bases was increased, until this reached or exceeded six, at which point the stimulation index began to decline. In general, the optimal number of 3' S linkages for spleen cell stimulation was five. Of all three concentrations tested in these experiments, the S-ODN was less stimulatory than the optimal chimeric compounds.

Dependent of GpG-Mediated Lymphocyte Activation on the Type of Backbone Modification Phosphorothioate modified ODN (S-ODN) are far more nuclease resistant than phosphodiester modified ODN (O-ODN). Thus, the increased immune stimulation caused by S-ODN and S-O-ODN (i.e., chimeric phosphorothioate ODN in which the central linkages are phosphodiester, but the two 5' and five 3' linkages are phosphorothioate modified) compared to O-ODN may result from the nuclease resistance of the former. To determine the role of ODN nuclease resistance in immune stimulation by CpG ODN, the stimulatory effects of chimeric ODN in which the 5' and 3' ends were rendered nuclease resistant with either methylphosphonate (MP-), methylphosphorothioate (MPS-), phosphorothioate (S-), or phosphorodithioate ($S_2$-) internucleotide linkages were tested (Example 10). These studies showed that despite their nuclease resistance, MP-O-ODN were actually less immune stimulatory than O-ODN. However, combining the MP and S modifications by replacing both nonbridging O molecules with 5' and 3' MPS internucleotide linkages restored immune stimulation to a slightly higher level than that triggered by O-ODN.

S-O-ODN were far more stimulatory than O-ODN, and were even more stimulatory than S-ODN, at least at concentrations above 3.3 µM. At concentrations below 3 µM, the S-ODN with the 3M sequence was more potent than the corresponding S-O-ODN, while the S-ODN with the 3D sequence was less potent than the corresponding S-O-ODN (Example 10). In comparing the stimulatory CpG motifs of these two sequences, it was noted that the 3D sequence is a perfect match for the stimulatory motif in that the CpG is flanked by two 5' purines and two 3' pyrimidines. However, the bases immediately flanking the CpG in ODN 3D are not optimal; it has a 5' pyrimidine and a 3' purine. Based on further testing, it was found that the sequence requirement for immune stimulation is more stringent for S-ODN than for S-O- or O-ODN. S-ODN with poor matches to the optimal CpG motif cause little or no lymphocyte activation (e.g., Sequence 3D). However, S-ODN with good matches to the motif, most critically at the positions immediately flanking the CpG, are more potent than the corresponding S-O-ODN (e.g., Sequence 3M, Sequences 4 and 6), even though at higher concentrations (greater than 3 µM) the peak effect from the S-O-ODN is greater (Example 10).

$S_2$-O-ODN were remarkably stimulatory, and caused substantially greater lymphocyte activation than the corresponding S-ODN or S-O-ODN at every tested concentration.

The increased B cell stimulation seen with CpG ODN bearing S or $S_2$ substitutions could result from any or all of the following effects: nuclease resistance, increased cellular uptake, increased protein binding, and altered intracellular localization. However, nuclease resistance cannot be the only explanation, since the MP-O-ODN were actually less stimulatory than the O-ODN with CpG motifs. Prior studies have shown that ODN uptake by lymphocytes is markedly affected by the backbone chemistry (Zhao, et al. (1993) Comparison of cellular binding and uptake of antisense phosphodiester, phosphorothioate, and mixed phosphorothioate and methylphosphonate oligonucleotides. (Antisense Research and Development 3, 53-66; Zhao et al., (1994) Stage specific oligonucleotide uptake in murine bone marrow B cell precursors. Blood 84, 3660-3666). The highest cell membrane binding and uptake was seen with S-ODN, followed by S-O-ODN, O-ODN, and MP-ODN. This differential uptake correlates with the degree of immune stimulation.

Unmethylated CpG Containing Oligos have NK Cell Stimulatory Activity

Experiments were conducted to determine whether CpG containing oligonucleotides stimulated the activity of natural killer (NK) cells in addition to B cells. As shown in Table 8, to a marked induction of NK activity among spleen cells cultured with CpG ODN 1 and 3Dd was observed. In contrast, there was relatively on induction in effectors that had been treated with non-CpG control ODN.

TABLE 8

Induction Of NK Activity By CpG Oligodeoxynucleotides (ODN)

| | % YAC-1 Specific Lysis* | | % 2C11 Specific Lysis | |
|---|---|---|---|---|
| | Effector: | Target | Effector: | Target |
| ODN | 50:1 | 100:1 | 50:1 | 100:1 |
| None | −1.1 | −1.4 | 15.3 | 16.6 |
| 1 | 16.1 | 24.5 | 38.7 | 47.2 |
| 3Dd | 17.1 | 27.0 | 37.0 | 40.0 |
| non-CpG ODN | −1.6 | −1.7 | 14.8 | 15.4 |

Induction of NK Activity by DNA Containing CpG Motifs, but not by Non-CpG DNA.

Bacterial DNA cultured for 18 hrs at 37° C. and then assayed for killing of K562 (human) or Yac-1 (mouse) target cells induced NK lytic activity in both mouse spleen cells depleted of B cells and human PBMC, but vertebrate DNA may be a consequence of its increased level of unmethylated CpG dinucleotides, the activating properties of more than 50 synthetic ODN containing unmethylated, methylated, or no CpG dinucleotides was tested. The results, summarized in Table 9, demonstrate that synthetic ODN can stimulate significant NK activity, as long as they contain at least one unmethylated CpG dinucleotide. No difference was observed in the stimulatory effects of ODN in which the CpG was within a palindrome (such as ODN 1585, which contains the palindrome AACGTT; SEQ. ID. NO: 105) from those ODN without palindromes (such as 1613 ro 1619), with the caveat that optimal stimulation was generally seem with ODN in which the CpG was flanked by two 5' purines or a 5' GpT dinucleotide and two 3' pyrimidines. Kinetic experiments demonstrated that NK activity peaked around 18 hrs. after addition of the ODN. The data indicates that the murine NK response is dependent on the prior activation of monocytes by CpG DNA, leading to the production of IL-12, TNF-α, and IFN-α/b (Example 11).

Identification of Phosphorothioate ODN with Optimal CpG Motifs for Activation of Human NK Cells.

To have clinical utility, ODN must be administered to a subject in a form that protects them against nuclease degradation. Methods to accomplish this with phosphodiester ODN are well known in the art and include encapsulation in lipids or delivery systems such as nanoparticles. This protection can also be achieved using chemical substitutions to the DNA such as modified DNA backbones including those in which the internucleotide linkages are nuclease resistant. Some modifications may confer additional desirable properties such as increasing cellular uptake. For example, the phosphodiester linkage can be modified via replacement of one of the nonbridging oxygen atoms with a sulfur, which constitutes phosphorothioate DNA. Phosphorothioate ODN have enhanced cellular uptake (Krieg et al., Antisense Res. Dev. 6:133, 1996.) and improved B cell stimulation if they also have a CpG motif. Since NK activation correlates strongly with in vivo adjuvant effects, the identification of phosphorothioate ODN that will activate human NK cells is very important.

TABLE 9

Induction of NK Activity by DNA Containing CpG Motifs but not by Non-CpG DNA

| DNA or Cytokine Added | | | Mouse Cells | Human Cells |
|---|---|---|---|---|
| | | Expt. 1 | | |
| None | | | 0.00 | 0.00 |
| IL-2 | | | 16.68 | 15.82 |
| E. Coli. DNA | | | 7.23 | 5.05 |
| Calf thymus DNA | | | 0.00 | 0.00 |
| | | Expt. 2 | | |
| None | | | 0.00 | 3.28 |
| 1585 ggGGTCAA<u>CG</u>TTGAGggggg | (SEQ ID No. 12) | | 7.38 | 17.98 |
| 1629 --------------gtc------------- | (SEQ ID No. 41) | | 0.00 | 4.4 |
| | | Expt. 3 | | |
| None | | | 0.00 | |
| 1613 GCTAGA<u>CG</u>TTAGTGT | (SEQ ID No. 42) | | 5.22 | |
| 1769 --------------Z----------- | (SEQ ID No. 117) | | 0.02 | ND |
| 1619 TCCATGT<u>CG</u>TTCCTGATGCT | (SEQ ID No. 38) | | 3.35 | |
| 1765 --------------Z------------------ | (SEQ ID No. 44) | | 0.11 | |

CpG dinucleotides in ODN sequences are indicated by underlying; Z indicates methylcytosine. Lower case letters indicate nuclease resistant phosphorothioate modified internucleotide linkages which, in titration experiments, were more than 20 times as potent as non-modified ODN, depending on the flanking bases. Poly G ends (g) were used in some ODN, because they significantly increase the level of ODN uptake.

Figure 6:
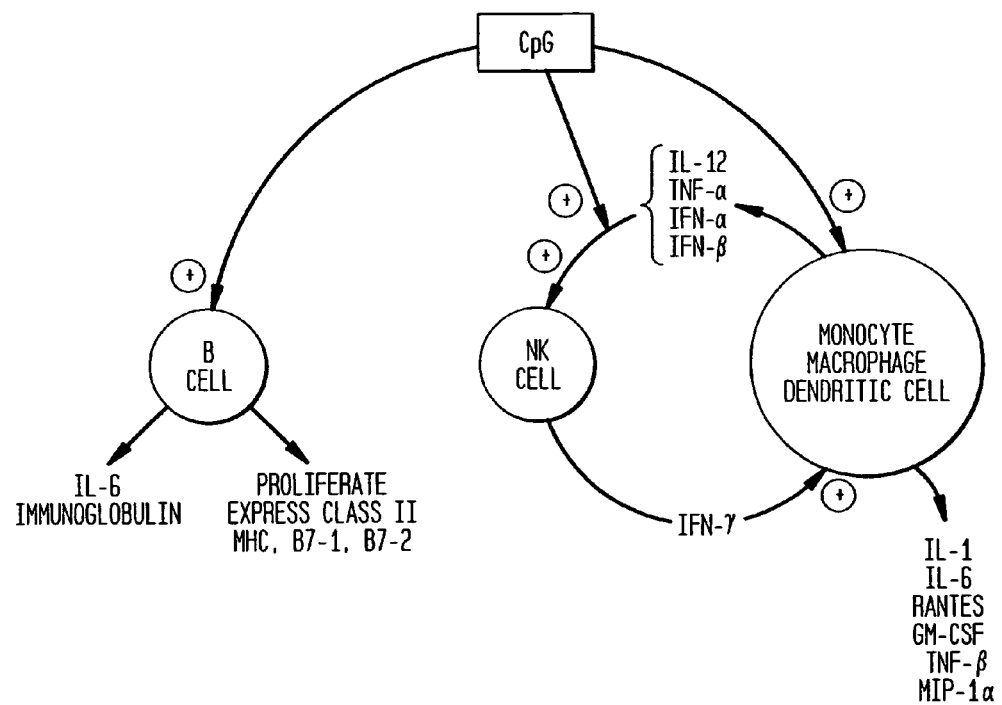

From all of these studies, a more complete understanding of the immune effects of CpG DNA has been developed, which is summarized in FIG. 6.

Immune activation by CpG motifs may depend on bases flanking the CpG, and the number of spacing of the CpGs present within an ODN. Although a single CpG in an ideal base context can be a very strong and useful immune activator, superior effects can be seen with ODN containing several CpGs with the appropriate spacing and flanking bases. For activation of murine B cells, the optimal CpG motif is TGACGTT (SEQ. ID. NO: 108); residues 10-17 of Seq. ID. No 70.

The following studies where conducted to identify optimal ODN sequences for stimulation of human cells by examining the effects of changing the number, spacing, and flanking bases of CpG dinucleotides.

The effects of different phosphorothioate ODNs—containing CpG dinucleotides in various base contexts—on human NK activation (Table 10) were examined. ODN 1840, which contained 2 copies of the TGTCGTT (SEQ. ID. NO: 102) residues 14-20 of SEQ. ID. NO: 47 motif, had significant NK lytic activity (Table 10). To further identify additional ODNs optimal for NK activation, approximately one hundred ODN containing different numbers and spacing of CpG motifs, were tested with ODN 1982 serving as a control. The results are shown in Table 11.

Effective ODNs began with a TC or TG at the 5' end, however, this requirement was not mandatory. ODNs with internal CpG motifs (e.g., ODN 1840) are generally less potent stimulators than those in which a GTCGCT (SEQ. ID. NO: 58) motif immediately follows the 5' TC (e.g., ODN 1967 and 1968). ODN 1968, which has a second GTCGTT (SEQ. ID. NO: 57) motif in its 3' half, was consistently more stimulatory than ODN 1967, which lacks this second motif. ODN 1967, however, was slightly more potent than ODN 1968 in experiments 1 and 3, but not in experiment 2. ODN 2005, which has a third GTCGTT (SEQ. ID. NO: 57) motif, inducing slightly higher NK activity on average than 1968. However, ODN 2006, in which the spacing between the GTCGTT (SEQ. ID. NO: 57) motifs was increased by the addition of two Ts between each motif, was superior to ODN 2005 and to ODN 2007, in which only one of the motifs had the additional of the spacing two Ts. The minimal acceptable spacing between CpG motifs is one nucleotide as long as the ODN has two pyrimidines (preferably T) at the 3' end (e.g., ODN 2015). Surprisingly, joining two GTCGTT (SEQ. ID. NO: 57) motifs end to end with a 5' T also created a reasonably strong inducer of NK activity (e.g., ODN 2016). The choice of thymine (T) separating consecutive CpG dinucleotides is not absolute, since ODN 2002 induced appreciable NK activation despite the fact that adenine (A) separated its CpGs (i.e., CGACGTT; SEQ. ID. NO: 113). It should also be noted that ODNs containing no CpG (e.g., ODN 1982), runs of CpGs, or CpGs in bad sequence contents (e. Q. ODN 2010) had no stimulatory effect on NK activation.

TABLE 10

| ODN cells alone | Sequence (5'-3') | LU 0.01 | |
|---|---|---|---|
| 1754 | ACCATGGACGATCTGTTTCCCCTC | 0.02 | SEQ ID NO: 59 |
| 1758 | TCTCCCAGCGTGCGCCAT | 0.05 | SEQ ID NO: 45 |
| 1761 | TACCGCGTGCGACCCTCT | 0.05 | SEQ ID NO: 60 |
| 1776 | ACCATGGACGAACTGTTTCCCCTC | 0.03 | SEQ ID NO: 61 |
| 1777 | ACCATGGACGAGCTGTTTCCCCTC | 0.05 | SEQ ID NO: 62 |

TABLE 10-continued

| ODN cells alone | Sequence (5'-3') | LU 0.01 | |
|---|---|---|---|
| 1778 | ACCATGGACGACCTGTTTCCCCTC | 0.01 | SEQ ID NO: 63 |
| 1779 | ACCATGGACGTACTGTTTCCCCTC | 0.02 | SEQ ID NO: 64 |
| 1780 | ACCATGGACGGTCTGTTTCCCCTC | 0.29 | SEQ ID NO: 65 |
| 1781 | ACCATGGACGTTCTGTTTCCCCTC | 0.38 | SEQ ID NO: 66 |
| 1823 | GCATGACGTTGAGCT | 0.08 | SEQ ID NO: 6 |
| 1824 | CACGTTGAGGGGCAT | 0.01 | SEQ ID NO: 67 |
| 1825 | CTGCTGAGACTGGAG | 0.01 | SEQ ID NO: 68 |
| 1828 | TCAGCGTGCGCC | 0.01 | SEQ ID NO: 69 |
| 1829 | ATGACGTTCCTGACGTT | 0.42 | SEQ ID NO: 70 |
| 1830[2] | RANDOM SEQUENCE | 0.25 | |
| 1834 | TCTCCCAGCGGGCGCAT | 0.00 | SEQ ID NO: 71 |
| 1836 | TCTCCCAGCGCGCGCCAT | 0.46 | SEQ ID NO: 72 |
| 1840 | TCCATGTCGTTCCTGTCGTT | 2.70 | SEQ ID NO: 73 |
| 1841 | TCCATAGCGTTCCTAGCGTT | 1.45 | SEQ ID NO: 74 |
| 1842 | TCGTCGCTGTCTCCGCTTCTT | 0.06 | SEQ ID NO: 75 |
| 1851 | TCCTGACGTTCCTGACGTT | 2.32 | SEQ ID NO: 76 |

[1]Lytic units (LU) were measured as described (8). Briefly, PBMC were collected from normal donors and spun over Ficoll, then cultured with or without the indicated ODN (which were added to cultures at 6 μg/ml) for 24 hr. Then their ability to lyse $^{51}$Cr-labeled K562 cells was determined. The results shown are typical of those obtained with several different normal human donors.
[2]This oligo mixture contained a random selection of all 4 bases at each position.

TABLE 11

Induction of NK LU by Phosphorothioate CpG ODN with Good Motifs

| ODN[1] cells alone | sequence (5'-3') | SEQ ID NO: | expt. 1 0.00 | expt. 2 1.26 | expt. 3 0.46 |
|---|---|---|---|---|---|
| 1840 | TCCATGTCGTTCCTGTCGTT | 73 | 2.33 | ND | ND |
| 1960 | TCCTGTCGTTCCTGTCGTT | 77 | ND | 0.48 | 8.99 |
| 1961 | TCCATGTCGTTTTTGTCGTT | 78 | 4.03 | 1.23 | 5.08 |
| 1962 | TCCTGTCGTTCCTTGTCGTT | 52 | ND | 1.60 | 5.74 |
| 1963 | TCCTTGTCGTTCCTGTCGTT | 121 | 3.42 | ND | ND |
| 1965 | TCCTGTCGTTTTTTGTCGTT | 53 | 0.46 | 0.42 | 3.48 |
| 1966 | TCGTCGCTGTCTCCGCTTCTT | 75 | 2.62 | ND | ND |
| 1967 | TCGTCGCTGTCTGCCCTTCTT | 54 | 5.82 | 1.64 | 8.32 |
| 1968 | TCGTCGCTGTTGTCGTTTCTT | 55 | 3.77 | 5.26 | 6.12 |
| 1979[2] | TCCATGTZGTTCCTGTZGTT | 122 | 1.32 | ND | ND |
| 1982 | TCCAGGACTTCTCTCAGGTT | 79 | 0.05 | ND | 0.98 |
| 1990 | TCCATGCGTGCGTGCGTTTT | 80 | 2.10 | ND | ND |
| 1991 | TCCATGCGTTGCGTTGCGTT | 81 | 0.89 | ND | ND |
| 2002 | TCCACGACGTTTTCGACGTT | 82 | 4.02 | 1.31 | 9.79 |
| 2005 | TCGTCGTTGTCGTTGTCGTT | 47 | ND | 4.22 | 12.75 |

TABLE 11-continued

Induction of NK LU by Phosphorothioate CpG ODN with Good Motifs

| ODN[1] | cells alone | sequence (5'-3') | SEQ ID NO: | expt. 1 0.00 | expt. 2 1.26 | expt. 3 0.46 |
|---|---|---|---|---|---|---|
| 2006 | | TCGTCGTTTTGTCGTTTTGTCGT | 123 | ND | 6.17 | 12.82 |
| 2007 | | TCGTCGTTGTCGTTTTGTCGTT | 49 | ND | 2.68 | 9.66 |
| 2008 | | GCGTGCGTTGTCGTTGTCGTT | 56 | ND | 1.37 | 8.15 |
| 2010 | | GCGGCGGGCGGCGCGCGCCC | 83 | ND | 0.01 | 0.05 |
| 2012 | | TGTCGTTTGTCGTTTGTCGTT | 48 | ND | 2.02 | 11.61 |
| 2013 | | TGTCGTTGTCGTTGTCGTTGTCGTT | 84 | ND | 0.56 | 5.22 |
| 2014 | | TGTCGTTGTCGTTGTCGTT | 50 | ND | 5.74 | 10.89 |
| 2015 | | TCGTCGTCGTCGTT | 51 | ND | 4.53 | 10.13 |
| 2016 | | TGTCGTTGTCGTT | 85 | ND | 6.54 | 8.06 |

[1]PBMC essentially as described herein. Results are representative of 6 separate experiments; each experiment represents a different donor.
[2]This is the methylated version of ODN 1840;
Z = 5-methyl cytosine LU is lytic units;
ND = not done;
CpG dinucleotides are underlined for clarity.

Identification of Phosphorothioate ODN with Optimal CpG Motifs for Activation of Human B Cell Proliferation.

The ability of a CpG ODN to induce B cell proliferation is a good measure of its adjuvant potential. Indeed, ODN with strong adjuvant effects generally also induce B cell proliferation. To determine whether the optimal CpG ODN for inducing B cell proliferation are the same as those for inducing NK cell activity, similar panels of ODN (Table 12) were tested. The most consistent stimulation appeared with ODN 2006 (Table 12).

TABLE 12

Induction of human B cell proliferation by Phosphorothioate CpG ODN

| | | | Stimulation Index[1] | | | | | |
|---|---|---|---|---|---|---|---|---|
| ODN | sequence (5'-3') | SEQ ID NO: | expt. 1 | expt. 2 | expt. 3 | expt. 4 | expt. 5 | expt. 6 |
| 1840 | TCCATGTCGTTCCTGTCGTT | 73 | 4 | ND | ND | ND | ND | 34 |
| 1841 | TCCATAGCGTTCCTAGCGTT | 74 | 3 | ND | ND | ND | ND | ND |
| 1960 | TCCTGTCGTTCCTGTCGTT | 77 | ND | 2.0 | 2.0 | 3.6 | ND | ND |
| 1961 | TCCATGTCGTTTTTGTCGTT | 78 | 2 | 3.9 | 1.9 | 3.7 | ND | 37 |
| 1962 | TCCTGTCGTTCCTTGTCGTT | 52 | ND | 3.8 | 1.9 | 3.9 | 5.4 | 35 |
| 1963 | TCCTTGTCGTTCCTGTCGTT | 121 | 3 | ND | ND | ND | ND | ND |
| 1965 | TCCTGTCGTTTTTTGTCGTT | 53 | 4 | 3.7 | 2.4 | 4.7 | 6.0 | 43 |
| 1967 | TCGTCGCTGTCTGCCCTTCTT | 54 | ND | 4.4 | 2.0 | 4.5 | 5.0 | 36 |
| 1963 | TCGTCGCTGTTGTCGTTTCTT | 55 | ND | 4.0 | 2.0 | 4.9 | 8.7 | 38 |
| 1982 | TCCAGGACTTCTCTCAGGTT | 79 | 3 | 1.8 | 1.3 | 3.1 | 3.2 | 12 |
| 2002 | TCCACGACGTTTTCGACGTT | 86 | ND | 2.7 | 1.4 | 4.4 | ND | 14 |
| 2005 | TCGTCGTTGTCGTTGTCGTT | 47 | 5 | 3.2 | 1.2 | 3.0 | 7.9 | 37 |
| 2006 | TCGTCGTTTTGTCGTTTTGTCGTT | 46 | 4 | 4.5 | 2.2 | 5.8 | 8.3 | 40 |
| 2007 | TCGTCGTTGTCGTTTTGTCGTT | 49 | 3 | 4.0 | 4.2 | 4.1 | ND | 22 |
| 2008 | GCGTGCGTTGTCGTTGTCGTT | 56 | ND | 3.0 | 2.4 | 1.6 | ND | 12 |
| 2010 | GCGGCGGGCGGCGCGCGCCC | 33 | ND | 1.6 | 1.9 | 3.2 | ND | ND |
| 2012 | TGTCGTTTGTCGTTTGTCGTT | 48 | 2 | 2.8 | 0 | 3.2 | ND | 33 |

TABLE 12-continued

Induction of human B cell proliferation by Phosphorothioate CpG ODN

| | | | Stimulation Index[1] | | | | | |
|---|---|---|---|---|---|---|---|---|
| ODN | sequence (5'-3') | SEQ ID NO: | expt. 1 | expt. 2 | expt. 3 | expt. 4 | expt. 5 | expt. 6 |
| 2013 | TGTCGTTGTCGTTGTCGTTGTCGTT | 84 | 3 | 2.3 | 3.1 | 2.8 | ND | 7 |
| 2014 | TGTCGTTGTCGTTGTCGTT | 50 | 3 | 2.5 | 4.0 | 3.1 | 6.7 | 14 |
| 2015 | TCGTCGTCGTCGTT | 51 | 5 | 1.8 | 2.6 | 4.5 | 9.4 | 1 |
| 2016 | TGTCGTTGTCGTT | 85 | ND | 1.1 | 1.7 | 2.7 | 7.3 | 1 |

[1]Cells = human spleen cells stored at −70° C. after surgical harvest or PBMC collected from normal donors and spun over Ficoll. Cells were cultured in 96 well U-bottom microtiter plates with or without the indicated ODN (which were added to cultures at 6 µml). N = 12 experiments. Cells were cultured for 4-7 days, pulsed with 1 µCi of $^3$H thymidine for 18 hr. before harvest and scintillation counting. Stimulation index = the ratio of cpm in wells without ODN to that in wells that had been stimulated throughout the culture period with the indicated ODN (there were no further additions of ODN after the cultures were set up). ND = not done.

Identification of Phosphorothioate ODN that Induce Human IL-12 Secretion

The ability of a CpG ODN to induce IL-12 secretion is a good measure of its adjuvant potential, especially in terms of its ability to induce a Th1 immune response, which is highly dependent on IL-12. Therefore, the ability of a panel of phosphorothioate ODN to induce OIL-12 secretion from human PBMC in vitro (Table 13) was examined. These experiments showed that in some human PBMC, most CpG ODN could induce IL-12 secretion (e.g., expt. 1). However, other donors responded to just a few CpG ODN (E.g., expt. 2). ODN 2006 was a consistent inducer of IL12 secretion from most subjects (Table 13).

TABLE 13

Induction of human IL-12 secretion by Phosphorothioate CpG ODN

| | | SEQ ID | IL-12 (pg/ml) | |
|---|---|---|---|---|
| ODN[1] | sequence (5'-3') | NO: | expt. 1 | expt. 2 |
| cells alone | | | 0 | 0 |
| 1962 | TCCTGTCGTTCCTTGTCGTT | 52 | 19 | 0 |
| 1965 | TCCTGTCGTTTTTGTCGTT | 53 | 36 | 0 |
| 1967 | TCGTCGCTGTCTGCCCTTCTT | 119 | 41 | 0 |
| 1968 | TCGTCGCTGTTGTCGTTTCTT | 120 | 24 | 0 |
| 2005 | TCGTCGTTGTCGTTGTCGTT | 47 | 25 | 0 |
| 2006 | TCGTCGTTTTGTCGTTTTGTCGTT | 46 | 29 | 15 |
| 2014 | TGTCGTTGTCGTTGTCGTT | 50 | 28 | 0 |
| 2015 | TCGTCGTCGTCGTT | 51 | 14 | 0 |
| 2016 | TGTCGTTGTCGTT | 85 | 3 | 0 |

[1]PBMC were collected from normal donors and spun over Ficoll, then cultured at 10[6] cells/well in 96 well microtiter plates with or without the indicated ODN which were added to cultures at µg/ml. Supernatants were collected at 24 hr and tested for IL-12 levels by ELISA as described methods. A standard curve was run in each experiment, which represents a different donor.

Identification of B Cell and Monocyte/NK Cell-Specific Oligonucleotides

As shown in FIG. 6, CpG DNA can directly activate highly purified B cells and monocytic cells. There are many similarities in the mechanism through which CpG DNA activates these cell types. For example, both require NFkB activation as explained further below.

In further studies of different immune effects of CpG DNA, it was found that there is more than one type of CpG motif. Specifically, olio 1668, with the best mouse B cell motif, is a strong inducer of both B cell and natural killer (NK) cell activation, while olio 1758 is a weak B cell activator, but still induces excellent NK responses (Table 14).

TABLE 14

Different CpG motifs stimulate optimal murine B cell and NK activation

| ODN | Sequence | B cell activation | NK activation[2] |
|---|---|---|---|
| 1668 | TCCATGACGTTCCTGATGCT (SEQ. ID. NO 7) | 42,849 | 2.52 |
| 1758 | TCTCCCAGCGTGCGCCAT (SEQ. ID. NO. 45) | 1,747 | 6.66 |
| NONE | | 367 | 0.00 |

CpG dinucleotides are underlined; oligonucleotides were synthesized with phosphorothioate modified backbones to improve their nuclease resistance. [1]Measured by $^3$H thymidine incorporation after 48 hr culture with oligodeoxynucleotides at a 200 nM concentration as described in Example 1.
[2]Measured in lytic units.

Teleological Basis of Immunostimulatory, Nucleic Acids

Vertebrate DNA is highly methylated and CpG dinucleotides are under represented. However, the stimulatory CpG motif is common in microbial genomic DNA, but quite rare in vertebrate DNA. In addition, bacterial DNA has been reported to induce B cell proliferation and immunoglobulin (Ig) production, while mammalian DNA does not (Messina, J. P. et al., *J. Immunol.* 147:1759 (1991)). Experiments further described in Example 3, in which methylation of bacterial DNA with CpG methylase was found to abolish mitogenicity, demonstrates that the difference in CpG status is the cause of B cell stimulation by bacterial DNA. This data supports the following conclusion: that unmethylated CpG dinucleotides present within bacterial DNA are responsible for the stimulatory effects of bacterial DNA.

Teleologically, it appears likely that lymphocyte activation by the CpG motif represents an immune defense mechanism that can thereby distinguish bacterial from host DNA. Host DNA, which would commonly be present in many anatomic regions and areas of inflammation due to apoptosis (cell death), would generally induce little or mo lymphocyte activation due to CpG suppression and methylation. However, the presence of bacterial DNA containing unmethylated CpG motifs can cause lymphocyte activation precisely in infected anatomic regions, where it is beneficial. This novel activation pathway provides a rapid alternative to T cell dependent antigen specific B cell activation. Since the CpG pathway synergizes with B cell activation through the antigen receptor, B cells bearing antigen receptor specific for bacterial antigens would receive on e activation signal through cell membrane Ig and a second signal from bacterial DNA, and would therefore tend to be preferentially activated. The interrelationship of this pathway with other pathways of B cell activation provide a physiologic mechanism employing a polyclonal antigen to induce antigen-specific responses.

However, it is likely that B cell activation would not be totally nonspecific. B cells bearing antigen receptors specific for bacterial products could receive one activation signal through cell membrane Ig, and a second from bacterial DNA, thereby more vigorously triggering antigen specific immune responses. As with other immune defense mechanisms, the response to bacterial DNA could have undesirable consequences in some settings. For example, autoimmune responses to self antigens would also tend to be preferentially triggered by bacterial infections, since autoantigens could also provide a second activation signal to autoreactive B cells triggered by bacterial DNA. Indeed the induction of autoimmunity by bacterial infections is a common clinical observance. For example, the autoimmune disease systemic lupus erythematosus, which is: i) characterized by the production of anti-DNA antibodies; ii) induced by drugs which inhibit DNA methyltransferase (Cornaccia, E. J. et al., *J. Clin. Invest.* 92:38 (1993)); and iii) associated with reduced DNA methylation (Richardson, B., L. et al., *Arth. Rheum* 35:647 (1992)), is likely triggered at least in part by activation of DNA-specific B cells through stimulatory signals provided by CpG motifs, as well as by binding of bacterial DNA to antigen receptors.

Further, sepsis, which is characterized by high morbidity and mortality due to massive and nonspecific activation of the immune system may be initiated by bacterial DNA and other products released from dying bacteria that reach concentrations sufficient to directly activate many lymphocytes. Further evidence of the role of CpG DNA in the sepsis syndrome is described in Cowdery, J., et. al., (1996) the *Journal of Immunology* 156:4570-4575.

Unlike antigens that trigger B cells through their surface Ig receptor, CpG-ODN did not induce any detectable $Ca^{2+}$ flux, changes in protein tyrosine phosphorylation, or IP 3 generation. Flow cytometry with FITC-conjugated ODN with or without a CpG motif was performed as described in Zhao, Q et al., (*Antisense Research and Development* 3:53-66 (1993)), and showed equivalent membrane binding, cellular uptake, efflux, and intracellular localization. This suggests that there may not be cell membrane proteins specific for CpG ODN. Rather than acting through the cell membrane, that data suggests that unmethylated CpG containing oligonucleotides require cell uptake for activity: ODN covalently linked to a solid Teflon support were nonstimulatory, as were biotinylated ODN immobilized on either avidin beads or avidin coated petri dishes. CpG ODN conjugated to either FITC or biotin retained full mitogenic properties, indicated no stearic hindrance.

Figure 7:
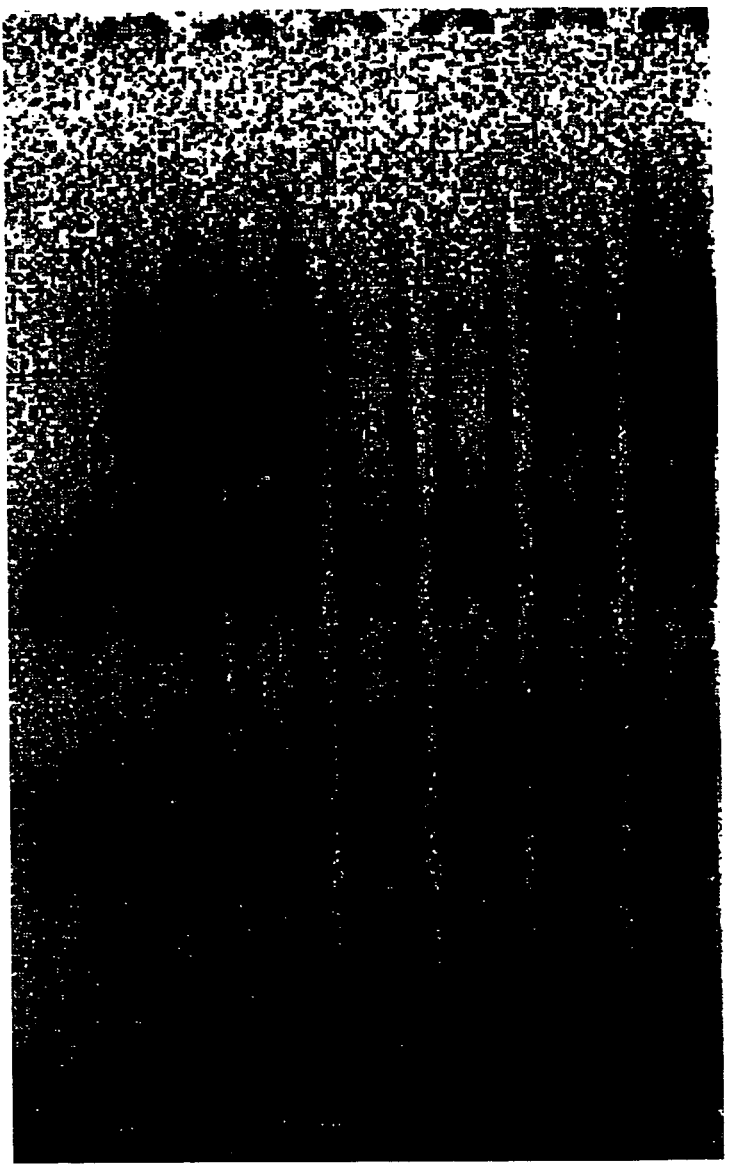

Recent data indicate the involvement of the transcription factor NFkB as a direct or indirect mediator of the CpG effect. For example, within 15 minutes of treating B cells or monocytes with CpG DNA, the level of NFkB binding activity is increased (FIG. 7). However, it is not increased by DNA that does not contain CpG motifs. In addition, it was found that two different inhibitors of NFkB activation, PDTC and gliotoxin, completely block the lymphocyte stimulation by CpG DNA as measured by B cell proliferation or monocytic cell cytokine secretion, suggesting that NFkB activation is required for both cell types.

There are several possible mechanisms through which NFkB can be activated. These include through activation of various protein kinases, or through the generation of reactive oxygen species. No evidence for protein kinase activation induced immediately after CpG DNA treatment of B cells or monocytic cells have been found, and inhibitors of protein kinase A, protein kinase C, and protein tyrosine kinases had no effects on the CpG induced activation. k However, CpG DNA causes a rapid induction of the production of reactive oxygen species in both B cells and monocytic cells, as detected by the sensitive fluorescent dye dihydrorhodamine 123 as described in Royall, J. A., and Ischiropoulos, H. (*Archives of Biochemistry and Biophysics* 302:348-355 (1993)). Moreover, inhibitors of the generation of these reactive oxygen species completely block the induction of NFkB and the later induction of cell proliferation and cytokine secretion by CpG DNA.

Work backwards, the next question was how CpG DNA leads to the generation of reactive oxygen species so quickly. Previous studies by the inventors demonstrated that oligonucleotides and plasmid or bacterial DNA are taken up by cells into endosomes. These endosomes rapidly become acidified inside the cell. To determine whether this acidification step may be important in the mechanism through which CpG DNA activates reactive oxygen species, the acidification step was blocked with specific inhibitors of endosome acidification including chloroquine, monensin, and bafilomycin, which work through different mechanisms. FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. as expected, this level of reactive oxygen species was greatly increased to 80% in the cells treated for 20 minutes with PMA and ionomycin, a positive control (Panel B). The cells treated with the CpG oligo also showed an increase in the level of reactive oxygen species such that more than 50% of the cells became positive (Panel D). However, cells treated with an oligonucleotide with the identical sequence except that the CpG was switched did not show this significant increase in the level of reactive oxygen species (Panel E).

Figure 8B:
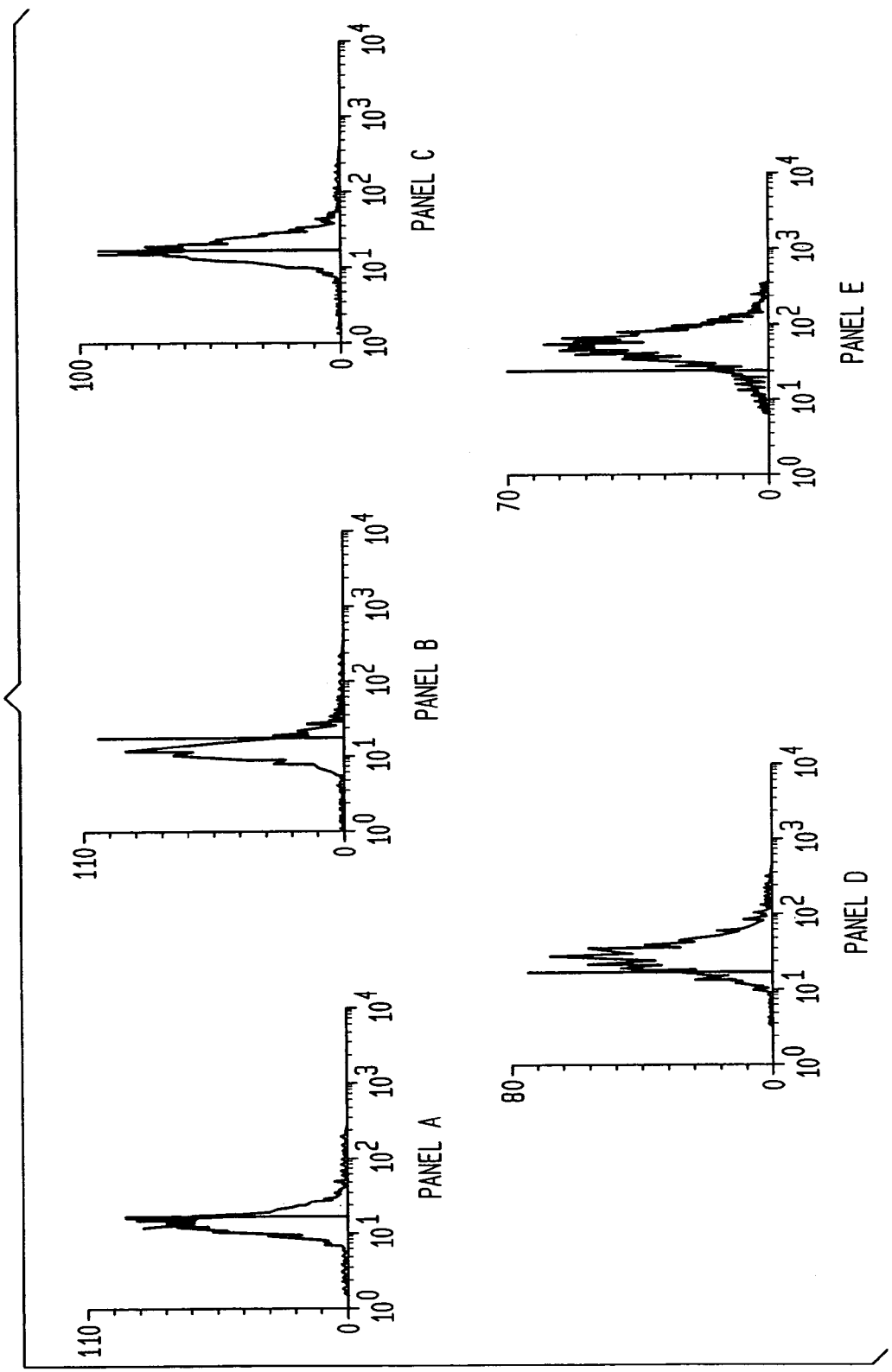

In the presence of chloroquine, the results are very different (FIG. 8B). Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in the cells treated with PMA and ionomycin (Panel E). This demonstrates that unlike the PMA plus ionomycin, the generation of reactive oxygen species following treatment of B cells with CpG DNA requires that the DNA undergo an acidification step in the endosomes. This is a completely novel mechanism of leukocyte activation. Chloroquine, monensin, and bafilomycin also appear to block the activation of NFkB by CpG DNA as well as the subsequent proliferation and induction of cytokine secretion.

Chronic Immune Activation by CpG DNA and Autoimmune Disorders

B cell activation by CpG DNA synergizes with signals through the B cell receptor. This raises the possibility that DNA-specific B cells may be activated by the concurrent binding of bacterial DNA to their antigen receptor, and by the co-stimulatory CpG-mediated signals. In addition, CpG DNA induces B cells to become resistant to apoptosis, a mechanism thought to be important for preventing immune responses to self antigens, such as DNA. Indeed, exposure to bDNA can trigger anti-DNA Ab production. Given this potential ability of CpG DNA to promote autoimmunity, it is therefore noteworthy that patients with the autoimmune disease systemic lupus erythematosus have persistently elevated levels of circulating plasma DNA which is enriched in hypomethylated CpGs. These findings suggest a possible role for chronic immune activation by CpG DNA in lupus etiopathogenesis.

A class of medications effective in the treatment of lupus is antimalarial drugs, such as chloroquine. While the therapeutic mechanism of these drugs has been unclear, they are known to inhibit endosomal acidification. Leukocyte activation by CpG DNA is not medicated through binding to a cell surface receptor, but requires cell uptake, which occurs via bases were switched to disrupt the CpGs. Supershift experiments using specific antibodies indicated that the activated NFκB complexes included the p50 and p65 components. Not unexpectedly, NFκB activation in LPS- or CpG-treated cells was accompanied by the degradation of IκBα and IκBβ. However, inhibitors of endosomal acidification selectively blocked all of the CpG-induced but none of the LPS-induced cellular activation events. The very low concentration of chloroquine (<10 μM) that has been determined to inhibit CpG-mediated leukocyte activation is noteworthy since it is well below that required for antimalarial activity and other reported immune effects (e.g., 100-1000 μM). These experiments support the role of a pH-dependent signaling mechanism in mediating the stimulatory effects of CpG DNA.

TABLE 15

Specific blockade of CpG-induced TNF-α and IL-12 expression by inhibitors of endosomal acidification or NFKB activation

| | | | Inhibitors: | | | | | | | |
|---|---|---|---|---|---|---|---|---|---|---|
| | Medium | | Bafilomycin (250 nM) | | Chloroquine (2.5 μg/ml) | | Monensin (10 μM) | NAC (50 mM) | TPCK (50 μM) | Gliotoxin (0.1 μg/ml) | Bisgliotoxin (0.1 μg/ml) |
| activators | TNF-α | IL-12 | TNF-α | IL-12 | TNF-α | IL-12 | TNF-α | IL-12 | TNF-α | TNF-α | TNF-α | TNT-α |
| Medium | 37 | 147 | 46 | 102 | 27 | 20 | 22 | 73 | 10 | 24 | 17 | 41 |
| CpG ODN | 455 | 17,114 | 71 | 116 | 28 | 6 | 49 | 777 | 54 | 23 | 31 | 441 |
| LPS | 901 | 22,485 | 1370 | 4051 | 1025 | 12418 | 491 | 4796 | 417 | 46 | 178 | 1120 |

Table 15 legend IL-12 and TNF-α assays: The murine monocyte cell line J774 ($1 \times 10^5$ cells/ml for IL-12 or $1 \times 10^6$ cells/ml for TNF-α), were cultured with or without the indicated inhibitors at the concentrations shown for 2 hr and then stimulated with the CpG oligodeoxynucleotide (ODN) 1826 (TCCATGACGTTCCTGACGTT SEQ ID NO: 10) at 2 μM or LPS (10 μg ml) for 4 hr (TNF-α or 24 hr (IL-12) at which time the supernatant was harvested. ELISA for IL-12 or TNT-α (pg/ml) was performed on the supernatants essentially as described (A. K. Krieg, A.-K. Yi, S. Matson, T. J. Waldschmidt, G. A. Bishop, R. Teasdale, G. Koretzky and D. Klinman, Nature 374, 546 (1995); Yi, A.-K., D. M. Klinman, T. L. Martin, S. Matson and A. M. Krieg, J. Immunol., 157, 5394-5402 (1996); Krieg, A. M, J. Lab. Clin. Med., 128, 128-133 (1996). Cells cultured with ODN that lacked CpG motifs did not induce cytokine secretion. Similar specific inhibition of CpG responses was seen with IL-6 assays, and in experiments using primary spleen cells or the B cell lines CH12.LX and WEHI-231. 2.5 μg/ml of chloroquine is equivalent to <5 μM. Other inhibitors of NF-κB activation including PDTC and calpain inhibitors I and II gave similar results to the inhibitors shown. The results shown are representative of those obtained in ten different experiments.

adsorptive endocytosis into an acidified chloroquine-sensitive intracellular compartment. This suggested the hypothesis that leukocyte activation by CpG DNA may occur in association with acidified endosomes, and might even be pH dependent. To test this hypothesis specific inhibitors of DNA acidification were applied to determine whether B cells or monocytes could respond to CpG DNA if endosomal acidification was prevented.

The earliest leukocyte activation event that was detected in response to CpG DNA is the production of reactive oxygen species (ROS), which is induced within five minutes in primary spleen cells and both B and monocyte cell lines. Inhibitors of endosomal acidification including chloroquine, bafilomycin A, and monensin, which have different mechanisms of action, blocked the CpG-induced generation of ROS, but had no effect on ROS generation mediated by PMA, or ligation of CD40 or IgM. These studies show that ROS generation is a common event in leukocyte activation through diverse pathways. This ROS generation is generally independent of endosomal acidification, which is required only for the ROS response to CpG DNA. ROS generation in response to CpG is not inhibited by the NFκB inhibitor gliotoxin, confirming that it is not secondary to NFκB activation.

To determine whether endosomal acidification of CpG DNA was also required for its other immune stimulatory effects were performed. Both LPS and CpG DNA induce similar rapid NFκB activation, increases in proto-oncogene mRNA levels, and cytokine secretion. Activation of NFκB by DNA depended on CpG motifs since it was not induced by bDNA treated with CpG methylase, nor by ODN in which Excessive immune activation by CpG motifs may contribute to the pathogenesis of the autoimmune disease systemic lupus erythematosus, which is associated with elevated levels of circulating hypomethylated CpG DNA. Chloroquine and related antimalarial compounds are effective therapeutic agents for the treatment of systemic lupus erythematosus and some other autoimmune diseases, although their mechanism of action has been obscure. Our demonstration of the ability of extremely low concentrations of chloroquine to specifically inhibit CpG-mediated leukocyte activation suggests a possible new mechanism for its beneficial effect. It is noteworthy that lupus recurrences frequently are thought to be triggered by microbial infection. Levels of bDNA present in infected tissues can be sufficient to induce a local inflammatory response. Together with the likely role of CpG DNA as a mediator of the sepsis syndrome and other diseases our studies suggest possible new therapeutic applications for the antimalarial drugs that act as inhibitors of endosomal acidification.

CpG-induced ROS generation could be an incidental consequence of cell activation, or a signal that mediates this activation. The ROS scavenger N-acetyl-L-cysteine (NAC) blocks CpG-induced NFκB activation, cytokine production, and B cell proliferation, suggesting a casual role for ROS generation in these pathways. These data are compatible with previous evidence supporting a role for ROS in the activation of NFκB. WEHI-231 B cells ($5 \times 10^5$ cells/ml) were precultured for 30 minutes with or without chloroquine (5 μg/ml [<10 μM]) or gliotoxin (0.2 μg/ml). Cell aliquots were then cultured as above for 10 minutes in RPMI medium with or without a CpG ODN (1826) or non-CpG ODN (1911) at 1 μM or phorbol myristate acetate (PMA) plus ionomycin (iono). Cells were then stained with dihydrorhodamine-123 and analyzed for intracellular ROS production by flow cytometry as described (A. K. Krieg, A.-K. Yi, S. Matson, T. J. Waldschmidt, G. A. Bishop, R. Teasdale, G. Koretzky and D. Klinman, *Nature* 374, 546 (1995); Yi, A.-K., D. M. Klinman, T. L. Martin, S. Matson and A. M. Krieg, *J. Immunol.*, 157, 5394-5402 (1996); Krieg, A. M, *J. Lab. Clin. Med.*, 128, 128-133 (1996)). J1774 cells, a monocytic line, showed similar pH-dependent CpG induced ROS responses. In contrast, CpG DNA did not induce the generation of extracellular ROS, nor any detectable neutrophil ROS. The concentrations of chloroquine (and those used with the other inhibitors of endosomal acidification) prevented acidification of the internalized CpG DNA using fluorescein conjugated ODN as described by Tonkinson, et al., (*Nucl. Acids Res.* 22, 4268 (1994); A. M. Krieg, In: *Delivery Strategies for Antisense Oligonucleotide Therapeutics*. Editor, S. Akhtar, CRC Press, Inc., pp. 177 (1995)). At higher concentrations than those required to inhibit endosomal acidification, nonspecific inhibitory effects were observed. Each experiment was performed at least three times with similar results.

While NFκB is known to be an important regulator of gene expression, it's role in the transcriptional response to CpG DNA was uncertain. To determine whether this NFκB activation was required for the CpG mediated induction of gene expression cells were activated with CpG DNA in the presence or absence of pyrrolidine dithiocarbamate (PDTC), an inhibitor of IκB phosphorylation. These inhibitors of NFκB activation completely blocked the CpG-induced expression of protooncogene and cytokine mRNA and protein, demonstrating the essential role of NFκB as a mediator of these events. None of the inhibitors reduced cell viability under the experimental conditions used in these studies. A J774, a murine monocyte cell line, was cultured in the presence of calf thymus (CT), *E. Coli* (EC), or methylated *E. Coli* (mEC) DNA (methylated with CpG methylase as $^{described}$) at 5 μg/ml or a CpG oligodeoxynucleotide (ODN 1826; Table 15) or a non-CpG ODN (ODN 1745; TCCATGAGCTTCCTGAGTCT, SEQ. ID. NO: 8) at 0.75 μM for 1 hr, following which the cells were lysed and nuclear extracts prepared. A double stranded ODN containing a consensus NFκB site was 5' radiolabeled and used as a probe for EMSA essentially as described (J. D. Dignam, R. M. Lebovitz and R. G. Roeder, *Nucleic Acids Res.* 11, 1475 (1983); M. Briskin, M. Damore, R. Law, G. Lee, P. W. Kincade, C. H. Sibley, M. Kuehl and R. Wall, *Mol. Cell. Biol.* 10, 422 (1990)). The position of the p50/p65 heterodimer was determined by supershifting with specific Ab to p65 and p50 (Santa Cruz Biotechnology, Santa Cruz, Calif.). Chloroquine inhibition of CpG-induced but not LPS-induced NFκB activation was established using J774 cells. The cells were precultured for 2 hr in the presence or absence of chloroquine (20 μg/ml) and then stimulated as above for 1 hr with either EC DNA, CpG ODN, non-CpG ODN or LPS (1 μg/ml). Similar chloroquine sensitive CpG-induced activation of NFκB was seen in a B cell line, WEHI-231 and primary spleen cells. These experiments were performed three times over a range of chloroquine concentrations form 2.5 to 20 μg/ml with similar results.

It was also established that CpG-stimulated mRNA expression requires endosomal acidification and NFκB activation in B cells and monocytes. J774 cells ($2 \times 10^6$ cells/ml) were cultured for 2 hr in the presence or absence of chloroquine (2.5 μg/ml [<5 μM]) or N-tosyl-L-phenylalanine chlorometryl ketone (TPCK: 50 μM), a serine/threonine protease inhibitor that prevents IκB proteolysis and thus blocks NFκB activation. Cells were then stimulated with the addition of *E. Coli* DNA (EC: 50 μg/ml), calf thymus DNA (CT: 50 μg/ml), LPS (10 μg/ml), CpG ODN (1826; 1 μM), or control non CpG ODN (1911; 1 μM) for 3 hr. WEHI-231 B cells ($5 \times 10^5$ cells/ml) were cultured in the presence or absence of gliotoxin (0.1 μg/ml) or bisgliotoxin (0.1 μg/ml) for 2 hrs and then stimulated with a CpG ODN (1826), or control non-CpG ODN (1911; TCCAGGACTTTCCTCAGGTT; SEQ. ID. NO. 97) at 0.5 μM for 8 hr. In both cases, cells were harvested and RNA was prepared using RNAzol following the manufacturer's protocol. Multi-probe RNASE protection assay was performed as described (A.-K. Yi, P. Hornbeck, D. E. Lafrenz and A. M. Krieg, *J. Immunol.*, 157, 4918-4925 (1996). Comparable amounts of RNA were loaded into each lane by using ribosomal mRNA as a loading control (L32). These experiments were performed three times with similar results.

The results indicate that leukocytes respond to CpG DNA through a novel pathway involving the pH-dependent generation of intracellular ROS. The pH dependent step may be the transport or processing of the CpG DNA, the ROS generation, or some other event. ROS are widely thought to be second messengers in signaling pathways in diverse cell types, but have not previously been shown to mediate a stimulatory signal in B cells.

Presumably, there is a protein in or near the endosomes that specifically recognizes DNA containing CpG motifs and leads to the generation of reactive oxygen species. To detect any protein in the cell cytoplasm that may specifically bind CpG DNA, electrophoretic mobility shift assays (EMSA) were used with 5' radioactively labeled oligonucleotides with or without CpG motifs. A band was found that appears to represent a protein binding specifically to single stranded oligonucleotides that have CpG motifs, but not to oligonucleotides that lack CpG motifs or to oligonucleotides in which the CpG motif has been methylated. This binding activity is blocked if excess of oligonucleotides that contain the NFκB binding site was added. This suggests that an NFκB or related protein is a component of a protein or protein complex that binds the stimulatory CpG oligonucleotides.

No activation of CREB/ATF proteins was found at time points where NFκB was strongly activated. These data therefore do not provide proof the NFκB proteins actually bind to the CpG nucleic acids, but rather that the proteins are required in some way for the CpG activity. It is possible that a CREB/ATF or related protein may interact in some way with NFκB proteins or other proteins thus explaining the remarkable similarity in the binding motifs for CREB proteins and the optimal CpG motif. It remains possible that the oligos bind to a CREB/ATF or related protein, and that this leads to NFκB activation.

Alternatively, it is very possible that the CpG nucleic acids may bind to one of the TRAF proteins that bind to the cytoplasmic region of CD40 and mediate NFκB activation when CD40 is cross-linked. Examples of such TRAF proteins include TRAF-2 and TRAF-5.

Method for Making Immunostimulatory Nucleic Acids

For use in the instant invention, nucleic acids can be synthesized de novo using any of a number of procedures well known in the art. For example, the b-cyanoethyl phosphoramidite method (S. L. Beaucage and M. H. Caruthers, (1981) *Tet. Let.* 22:1859); nucleoside H-phosphonate method (Garegg et al., (1986) *Tet. Let.* 27:4051-4054; Froehler et al., (1986) *Nucl. Acid. Res* 14:5399-5407; Garegg eg al., (1986) *Tet. Let.* 27:4055-4058, Gaffney et al., (1988) *Tet. Let.* 29:2619-2622). These chemistries can be performed by a variety of automated oligonucleotide synthesizers available in the market. Alternatively, oligonucleotides can be prepared from existing nucleic acid sequences (e.g. genomic or cDNA)

using known techniques, such as those employing restriction enzymes, exonucleases or endonucleases.

For use in vivo, nucleic acids are preferably relatively resistant to degradation (e.g. via endo- and exo-nucleases). Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made e.g. as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. And Peyman, A. (1990) *Chem. Rev.* 90:544; Goodchild, J. (1990) *Bioconjugate Chem.* 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (e.g. B-cell, monocytic cell and natural killer (NK) cell) surfaces and/or increased cellular uptake by target cells to form a "nucleic acid delivery complex". Nucleic acids can be ionically, or covalently associated with appropriate molecules using techniques which are well known in the art. A variety of coupling or crosslinking agents can be sued e.g. Protein A, carbodiimide, and N-succinimidyl-3-(2-pyridyldithio) propionate (SPDP). Nucleic acids can alternatively be encapsulated in liposomes or virosomes using well-known techniques.

Therapeutic Uses of Immunostimulatory Nucleic Acid Molecules

Based on their immunostimulatory properties, nucleic acid molecules containing at least one unmethylated CpG dinucleotide can be administered to a subject in vivo to treat an "immune system deficiency". Alternatively, nucleic acid molecules containing at least one unmethylated CpG dinucleotide can be contacted with lymphocytes (e.g. B cells, monocytic cells or NK cells) obtained from a subject having an immune system deficiency ex vivo and activated lymphocytes can then be re-implanted in the subject.

As reported herein, in response to unmethylated CpG containing nucleic acid molecules, an increased number of spleen cells secrete IL-6, IL-12, IFNγ, IFN-α, IFN-β, IL-1, IL-3, IL-10, TNF-α, TNF-β, GM-CSF, RANTES, and probably others. The increased IL-6 expression was found to occur in B cells, CD4$^+$T cells and monocytic cells.

Immunostimulatory nucleic acid molecules can also be administered to a subject in conjunction with a vaccine to boost a subject's immune system and thereby effect a better response from the vaccine. Preferably the immunostimulatory nucleic acid molecule is administered slightly before or at the same time as the vaccine. A conventional adjuvant may optionally be administered in conjunction with the vaccine, which is minimally comprised of an antigen, as the conventional adjuvant may further improve the vaccination by enhancing antigen absorption.

When the vaccine is a DNA vaccine at least two components determine its efficacy. First, the antigen encoded by the vaccine determines the specificity of the immune response.

Second, if the backbone of the plasmid contains CpG motifs, its functions as an adjuvant for the vaccine. Thus, CpG DNA acts as an effective "danger signal" and causes the immune system to respond vigorously to new antigens in the area. This mode of action presumably results primarily from the stimulatory local effects of CpG DNA on dendritic cells and other "professional" antigen presenting cells, as well as from the co-stimulatory effects on B cells.

Immunostimulatory oligonucleotides and unmethylated CpG containing vaccines, which directly activate lymphocytes and co-stimulate an antigen-specific response, are fundamentally different from conventional adjuvants (e.g. aluminum precipates), which are inert when injected alone and are thought to work through absorbing the antigen and thereby presenting it more effectively to immune cells. Further conventional adjuvants only work for certain antigens, only induce an antibody (humoral) immune response (Th2), and are very poor at inducing cellular immune responses (Th1). For many pathogens, the humoral response contributes little to protection, and can even be detrimental.

In addition, an immunostimulatory oligonucleotide can be administered prior to along with or after administration of a chemotherapy or immunotherapy to increase the responsiveness of the malignant cells to subsequent chemotherapy or immunotherapy or to speed the recovery of the bone marrow through induction of restorative cytokines such as GM-CSF. CpG nucleic acids also increase natural killer cell lytic activity and antibody dependent cellular cytotoxicity (ADCC). Induction of NK activity and ADCC may likewise be beneficial in cancer immunotherapy, alone or in conjunction with other treatments.

Another use of the described immunostimulatory nucleic acid molecules is in desensitization therapy for allergies, which are generally caused by IgE antibody generation against harmless allergens. The cytokines that are induced by unmethylated CpG nucleic acids are predominantly of a class called "Th1" which is most marked; by a cellular immune response and is associated with Il-12 and IFN-γ. The other major type of immune response is termed a Th2 immune response, which is associated with more of an antibody immune response and with the production of IL-4, Il-5 and IL-10. In general, it appears that allergic diseases are mediated by Th2 type immune responses and autoimmune diseases by Th1 immune response. Based on the ability of the immunostimulatory nucleic acid molecules to shift the immune response in a subject from a Th2 (which is associated with production of IgE antibodies and allergy) to a Th1 response (which is protective against allergic reactions), an effective dose of an immunostimulatory nucleic acid (or a vector containing a nucleic acid) alone or in conjunction with an allergen can be administered to a subject to treat or prevent an allergy.

Nucleic acids containing unmethylated CpG motifs may also have significant therapeutic utility in the treatment of asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines.

As described in detail in the following Example 12, oligonucleotides containing an unmethylated CpG motif (I, e,. TCCATGACGTTCCTGACGTT; SEQ ID NO. 10) but not a control oligonucleotide (TCCATGAGCTTCCTGAGTCT; SEQ ID NO. 8) prevented the development of an inflammatory cellular infiltrate and eosinophilia in a murine model of asthma. Furthermore, the suppression of eosinophilic inflammation was associated with a suppression of a Th2 response and induction of a Th1 response.

For use in therapy, an effective amount of an appropriate immunostimulatory nucleic acid molecule alone or formulated as a delivery complex can be administered to a subject by any mode allowing the oligonucleotide to be taken up by the appropriate target cells (e.g., B-cells and monocytic cells). Preferred routes of administration include oral and transdermal (e.g., via a patch). Examples of other routes of administration include injection (subcutaneous, intravenous, parenteral, intraperitoneal, intrathecal, etc.). The injection can be in a bolus or a continuous infusion.

A nucleic acid alone or as a nucleic acid delivery complex can be administered in conjunction with a pharmaceutically acceptable carrier. As used herein, the phrase "pharmaceutically acceptable carrier" is intended to include substances that can be coadministered with a nucleic acid or a nucleic acid delivery complex and allows the nucleic acid to perform its indicated function. Examples of such carriers include solutions, solvents, dispersion media, delay agents, emulsions and the like. The use of such media for pharmaceutically active substances are well known in the art. Any other conventional carrier suitable for use with the nucleic acids falls within the scope of the instant invention.

The term "effective amount" of a nucleic acid molecule refers to the amount necessary or sufficient to realize a desired biologic effect. For example, an effective amount of a nucleic acid containing at least one unmethylated CpG for treating an immune system deficiency could be that amount necessary to eliminate a tumor, cancer, or bacterial, viral or fungal infection. An effective amount for use as a vaccine adjuvant could be the amount useful for boosting a subjects immune response to a vaccine. An "effective amount" for treating asthma can be that amount; useful for redirecting a Th2 type of immune response that is associated with asthma to a Th1 type of response. The effective amount for any particular application can vary depending on such factors as the disease or condition being treated, the particular nucleic acid being administered (e.g. the number of unmethylated CpG motifs or their location in the nucleic acid), the size of the subject, or the severity of the disease or condition. One of ordinary skill in the art can empirically determine the effective amount of a particular oligonucleotide without necessitating undue experimentation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Effects of ODNs on B Cell Total RNA Synthesis and Cell Cycle

B cells were purified from spleens obtained from 6-12 week old specific pathogen free DBA/2 or BXSB mice (bred in the University of Iowa animal care facility; no substantial strain differences were noted) that were depleted of T cells with anti-Thy-1.2 and complement and centrifugation over lymphocyte M (Cedarlane Laboratories, Hornby, Ontario, Canada) ("B cells"). B cells contained fewer than 1% $CD4^+$ or $CD8^+$ cells. $8\times10^4$ B cells were dispensed in triplicate into 96 well microtiter plates in 100 µl RPMI containing 10% FBS (heat inactivated to 65° C. for 30 min.), 50 µM 2-mercaptoethanol, 100 U/ml penicillin, 100 ug/ml streptomycin, and 2 mM L-glutamate. 20 µM ODN were added at the start of culture for 20 h at 37° C., cells pulsed with 1 µCi of $^3H$ uridine, and harvested and counted 4 hr later. Ig secreting B cells were enumerated using the ALISA spot assay after culture of whole spleen cells with ODN at 20 µM for 48 hr. Data, reported in Table 1, represents the stimulation index compared to cell cultured without ODN. $^3H$ thymidine incorporation assays showed similar results, but with some nonspecific inhibition by thymidine released from degraded ODN (Matson. S and A. M. Krieg (1992) Nonspecific suppression of $^3H$-thymidine incorporation by control oligonucleotides. Antisense Research and Development 2:325).

Example 2

Effects of ODN on Production of IgM from B Cells

Single cell suspensions form the spleens of freshly killed mice were treated with anti-Thy1, anti-CD4, and anti-CD8 and complement by the method of Leibson et al., *J. Exp. Med.* 154:1681 (1981)). Resting B cells (<02% T cell contamination) were isolated from the 63-70% band of a discontinuous Percoll gradient by the procedure of DeFranco et al, *J. Exp. Med.* 155:1523 (1982). These were cultured as described above in 30 µg/ml LPS for 48 hr. The number of B cells actively secreting IgM was maximal at this time point, as determined by ELIspot assay (Klinman, D. M. et al. *J. Immunol.* 144:506 (1990)). In that assay, B cells were incubated for 6 hrs on anti-Ig coated microtiter plates. The Ig they produced (>99% IgM) was detected using phosphatase-labeled anti-Ig (Southern Biotechnology Associated, Birmingham, Ala.). The antibodies produced by individual B cells were visualized by addition of BCIP (Sigma Chemical Co., St. Louis Mo.) which forms an insoluble blue precipitate in the presence of phosphatase. The dilution of cells producing 20-40 spots/well was used to determine the total number of antibody-secreting B cells/sample. All assays were performed in triplicate (data reported in Table 1). In some experiments, culture supernatants were assayed for IgM by ELISA, and showed similar increased in response to CpG-ODN.

Example 3

B Cell Stimulation by Bacterial DNA

DBA/2 B cells were cultured with no DNA or 50 µg/ml of a (*Micrococcus lysodeikticus*; b) NZB/N mouse spleen; and c) NSF/N mouse spleen genomic DNAs for 48 hours, then pulsed with $^3H$ thymidine for 4 hours prior to cell harvest. Duplicate DNA samples were digested with DNASE I for 30 minutes at 37 C prior to addition to cell cultures. *E coli* DNA also induced an 8.8 fold increase in the number of IgM secreting B cells by 48 hours using the ELISAspot assay.

DBA/2 B cells were cultured with either no additive, 50 µg/ml LPS or the ODN 1; 1a; 4; or 4a at 20 uM. Cells were cultured and harvested at 4, 8, 24 and 48 hours. BXSB cells were cultured as in Example 1 with 5, 10, 20, 40 or 80 µM of ODN 1; 1a; 4; or 4a or LPS. In this experiment, wells with no ODN had 3833 cpm. Each experiment was performed at least three times with similar results. Standard deviations of the triplicate wells were <5%.

Example 4

Effects of ODN on Natural Killer (NK) Activity $10\times10^6$ C57BL/6 spleen cells were cultured in two ml RPMI (supplemented as described for Example 1) with or without 40 μM CpG or non-CpG ODN for forty-eight hours. Cells were washed, and then used as effector cells in a short term $^{51}$Cr release assay with YAC-1 and 2C11, two NK sensitive target cell lines (Ballas, Z. K. et al. (1993) *j. IMMUNOL.* 150:17). Effector cells were added at various concentrations to $10^{4}$ $^{51}$Cr-labeled target cells in V-bottom microtiter plates in 0.2 ml, and incubated in 5% $CO_2$ for 4 hr. At 37° C. Plates were then centrifuged, and an aliquot of the supernatant counted for radioactivity. Percent specific lysis was determined by calculating the ratio of the $^{51}$Cr released in the presence of effector cells minus the $^{51}$Cr released when the target cells are cultured alone, over the total counts released after cell lysis in 2% acetic acid minus the $^{51}$Cr cpm released when the cells are cultured alone.

Example 5

In Vivo Studies with CpG Phosphorothioate ODN

Mice were weighted and injected IP with 0.25 ml of sterile PBS or the indicated phosphorothioate ODN dissolved in PBS. Twenty four hours later, spleen cells were harvested, washed, and stained for flow cytometry using phycoerythrin conjugated 6B2 to gate on B cells in conjunction with biotin conjugated anti Ly-6A/E or anti-Ia$^d$ (Pharmingen, San Diego, Calif.) or anti-Bla-1 (Hardy, R. R. et al., *J. Exp. Med.* 159: 1169 (1984). Two mice were studied for each condition and analyzed individually.

Example 6

Titration of Phosphorothioate ODN for B Cell Stimulation

B cells were cultured with phosphorothioate ODN with the sequence of control ODN 1a or the CpG ODN 1d and 3 Db and then either pulsed after 20 hr with $^3$H uridine or after 44 hr with $^3$H thymidine before harvesting and determining cpm.

Example 7

Rescue of B Cells from Apoptosis

WEHI-231 cells ($5\times10^4$/well) were cultured for 1 hr. At 37 C in the presence or absence of LPS or the control ODN 1a or the CpG ODN 1d and 3 Db before addition of anti-IgM (1 μ/ml). Cells were cultured for a further 20 hr. Before a 4 hr. Pulse with 2 μCi/well $^3$H thymidine. In this experiment, cells with no ODN or anti-IgM gave $90.4\times10^3$ cpm of $^3$H thymidine incorporation by addition of anti-IgM. The phosphodiester ODN shown in Table 1 gave similar protection, though some nonspecific suppression due to ODN degradation. Each experiment was repeated at least 3 times with similar results.

Example 8

In Vivo Induction of Murine IL-6

DBA/2 female mice (2 mos. old) were injected IP with 500 g CpG or control phosphorothioate ODN. At various time points after injection, the mice were bled. Two mice were studied for each time point. IL-6 was measured by Elisa, and IL-6 concentration was calculated by comparison to a standard curve generate using recombinant IL-6. The sensitivity of the assay was 10 pg/ml. Levels were undetectable after 8 hrs.

Example 9

Systemic Induction of Murine IL-6 Transcription

Mice and cell lines. DBA/2, BALB/c, and C3H/HeJ mice at 5-10 wk of age were used as a source of lymphocytes. All mice were obtained from The Jackson Laboratory (Bar Harbor, Me.), and bred and maintained under specific pathogen-free conditions in the University of Iowa Animal Care Unit. The mouse B cell line CH12.LX was kindly provided by Dr. G. Bishop (University of Iowa, Iowa City).

Cell preparation. Mice were killed by cervical dislocation. Single cell suspensions were prepared aseptically from the spleens from mice. T cell depleted mouse splenocytes were prepared by using anti-Thy-1.2 and complement and centrifugation over lymphocyte M (Cedarlane Laboratories, Hornby, Ontario, Canada) as described (Krieg, A. M. et al., (1989) A role for endogenous retroviral sequences in the regulation of lymphocyte activation. *J. Immunol* 143:2448).

ODN and DNA. Phosphodiester oligonucleotides (O-ODN) and the backbone modified phosphorothioate oligonucleotides (S-ODN) were obtained from the DNA Core facility at the University of Iowa or from Operon Technologies (Alameda, Calif.). *E. Coli* DNA (Strain B) and calf thymus DNA were purchased from Sigma (St. Louis, Mo.). All DNA and ODN were purified by extraction with phenol:chloroform:isoamyl alcohol (25:24:1) and/or ethanol precipitation. *E. Coli* and calf thymus DNA were single stranded prior to use by boiling for 10 min. followed by cooling on ice for 5 min. For some experiments, *E. Coli* and calf thymus DNA were digested with DNase 1 (2 U/μg of DNA) at 37° C. for 2 hr in 1×SSC with 5 mM MgCl2. To methylate the cytosine in CpG dinucleotide in *E. Coli* DNA, *E. Coli* DNA was treated with CpG methylase (M. SsI; 2 U/μg of DNA) in NEBuffer 2 supplemented with 160 μM S-adenosyl methionine and incubated overnight at 37° C. Methylated DNA was purified as above. Efficiency of methylation was confirmed by Hpa II digestion followed by analysis by gel electrophoresis. All enzymes were purchased from New England Biolabs (Beverly, Mass.). LPS level in ODN was less than 12.5 ng/mg and *E. Coli* and calf thymus DNA contained less than 2.5 ng of LPS/mg of DNA by *Limulus* assay.

Cell Culture. All cells were cultured at 37° C. in a 5% $CO_2$ humidifier incubator maintained in RPMI-1640 supplemented with 10% (v/v) heat inactivated fetal calf serum (FCS), 1.5 mM L-glutamine, 50 μg/ml), CpG or non-CpG phosphodiester ODN (O-ODN) (20 μM), phosphorothioate ODN (S-ODN) (0.5 μM), or *E. coli* or calf thymus DNA (50 μg/ml) at 37° C. for 24 hr. (for IL-6 production) or 5 days (for IgM production). Concentrations of stimulants were chosen based on preliminary studies with titrations. In some cases, cells were treated with CpG O-ODN along with various concentrations (1-10 μg/ml) of neutralizing rat IgG1 antibody against murine IL-6 (hybridoma MP5-20F3) or control rat IgG1 mAb to *E. Coli* β-galactosidase (hybridoma GL 113; ATCC, 10801 University Boulevard, Manassas Va. 20110-2209) (20) for 5 days. At the end of incubation, culture supernatant fractions were analyzed by ELISA as below.

In vivo induction of IL-6 and IgM. BALB/c mice were injected intravenously (iv) with PBS, calf thymus DNA (200 μg/100 μl PBS/mouse), *E. coli* DNA (200 μg/100 μl PBS/ mouse), or CpG or non-CpG S-ODN (200 µg/100 µl PBS/mouse). Mice (two/group) were bled by retroorbital puncture and sacrificed by cervical dislocation at various time points. Liver, spleen, thymus, and bone marrow were removed by RNA was prepared from those organs using RNAzol B (Tel-Test, Friendswood, Tex.) according to the manufactures protocol.

ELISA. Flat-bottomed Immun 1 plates (Dynatech Laboratories, Inc., Chantilly, Va.) were coated with 100 µl/well of anti-mouse IL-6 mAb (MP5-20F3) (2 µg/ml) or anti-mouse IgM µ-chain specific (5 µg/ml; Sigma, St. Louis, Mo.) in carbonate-bicarbonate, pH 9.6 buffer (15 nM $Na_2CO_3$, 35 mM $NaHCO_3$) overnight at 4° C. The plates were then washed with TPBS (0.5 mM $MgCl_2O6H_2O$, 2.68 mM KCl, 1.47 mM $KH_2PO_4$, 0.14 M NaCl, 6.6 mM $K_2HPO_4$, 0.5% Tween 20) and blocked with 10% FCS and TPBS for 2 hr at room temperature and then washed again. Culture supernatants, mouse sera, recombinant mouse IL-6 (Pharmigen, San Diego, Calif.) or purified mouse IgM (Calbiochem, San Diego, Calif.) were appropriately diluted in 10% FCS and incubated in triplicate wells for 6 hr at room temperature. The plates were washed and 100 µl/well of biotinylated rat anti-mouse IL-6 monoclonal antibodies (MP5-32C11, Pharmingen, San Diego, Calif.) (1 µg/ml in 10% FCS) or biotinylated anti-mouse Ig (Sigma, St. Louis, Mo.) were added and incubated for 45 min. at room temperature following washes with TPBS. Horseradish peroxidase (HRP) conjugated avidin (Bio-rad Laboratories, Hercules, Calif.) at 1:4000 dilution in 10% FCS (100 µl/well) was added and incubated at room temperature for 30 min. The plates were washed and developed with o-phenylenediamine dihydrochloride (OPD; Sigma, St. Louis Mo.) 0.05 M phosphate-citrate buffer, pH 5.0, for 30 min. The reaction was stopped with 0.67 N $H_2SO_4$ and plates were read on a microplate reader (Cambridge Technology, Inc., Watertown, Mass.) at 490-600 nm. The results are shown in FIGS. 1 and 2.

Figure 3:
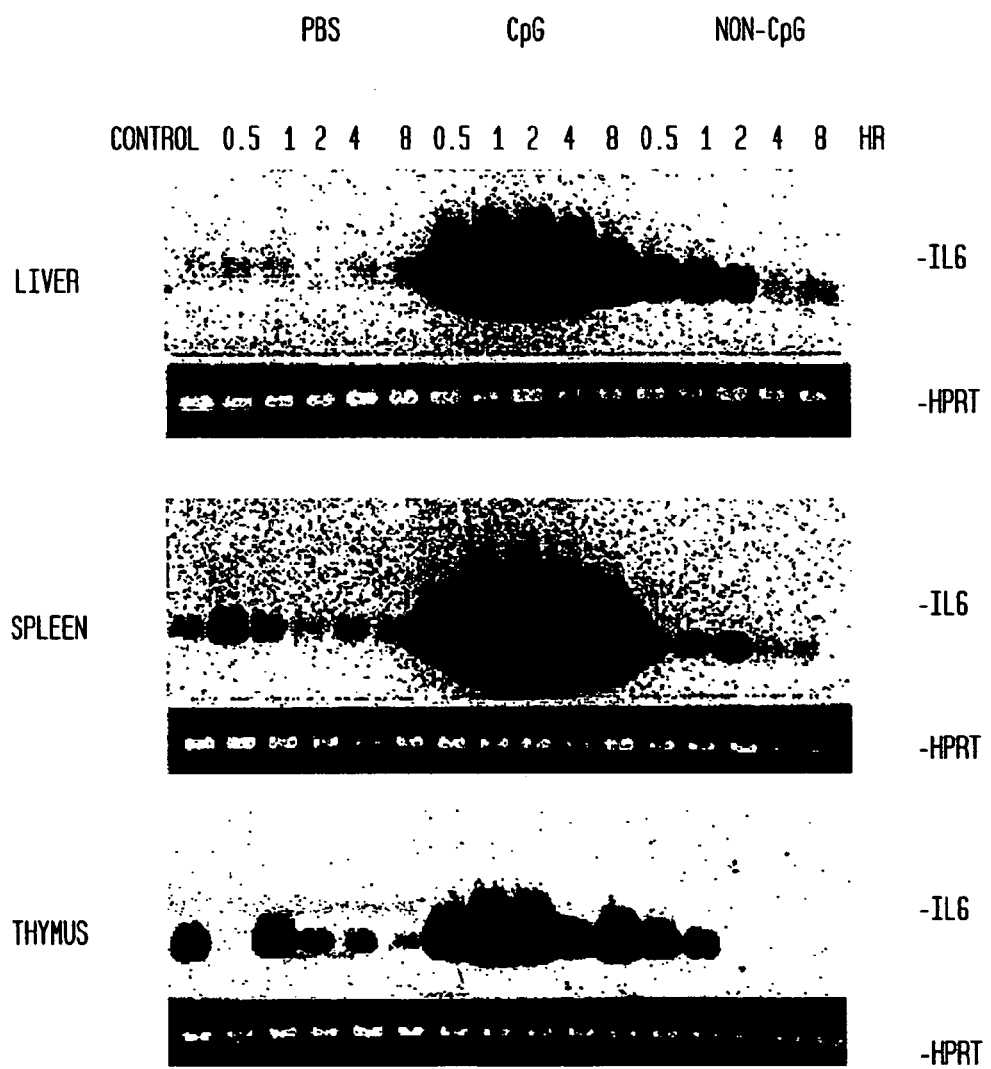

RT-PCR A sense primer, an antisense primer, and an internal oligonucleotide probe for IL-6 were synthesized using published sequences (Montgomery, R. A. and M. S. Dallman (1991), Analysis for cytokine gene expression during fetal thymic ontogeny using the polymerase chain reaction (*J. Immunol.*) 147:554). cDNA synthesis and IL-6 PCR was done essentially as described by Montgomery and Dallman (Montgomery, R. A. And M. S. Dallman (1991), Analysis of cytokine gene expression during fetal thymic ontogeny using the polymerase chain reaction (*J. Immunol.*) 147:554) using RT-PCR reagents from Perkin-Elmer Corp. (Hayward, Calif.). Samples were analyzed after 30 cycles of amplification by gel electrophoresis followed by unblot analysis (stoye, J. P. et al., (1991) DNA hybridization in dried gels with fragmented probes: an improvement over blotting techniques, *Techniques* 3:123). Briefly, the gel was hybridized at room temperature for 30 min. in denaturation buffer (0.05 M NaOH, 1.5M NaCl) followed by incubation for 30 min. In renaturation buffer (1.5 M NaCl, 1 M Tris, pH 8) and a 30 min. Wash in double distilled water. The gel was dried and prehybridized at 47° C. for 2 hr. Hybridization buffer (5×SSPE, 0.1% SDS) containing 10 µg/ml denatured salmon sperm DNA. The gel was hybridized with $2 \times 10^6$ cpm/ml g-[$^{32}$P] ATP end-labeled internal oligonucleotide probe for IL-6 (5'CATTTCCACGATTTCCCA3') SEQ ID. NO: 118) overnight at 47° C., washed 4 times (2×SSC, 0.2% SDS) at room temperature and autoradiographed. The results are shown in FIG. 3.

Cell Proliferation assay. DBA/2 mice spleen B cells ($5 \times 10^4$ cells/100 µl/well) were treated with media, CpG or non-CpG S-ODN (0.5 µM) or O-ODN (20 µM) for 24 hr at 37° C. Cells were pulsed for the last four hr. With either [$^3$H] Thymidine or [$^3$H] Uridine (1 µCi/well). Amounts of [$^3$H] incorporated were measured using Liquid Scintillation Analyzer (Packard Instrument Co., Downers Grove, Ill.).

Transfections and CAT assays. WEHI-231 cells ($10^7$ cells) were electroporated with 20 µg of control or human IL-6 promoter-CAT construct (kindly provided by S. Manolagas, Univ. of Arkansas) (Pottratz, S. T. Et al., (1994) 17B-estradiol inhibits expression of human interleukin-6 promotor-reporter constructs by a receptor-dependent mechanism. *J. Clin. Invest.* 93:944) at 250 mV and 960 µF. Cells were stimulated with various concentrations of CpG or non-CpG ODN after electroporation. Chloramphenicol acetyltransferase (CAT) activity was measured by a solution assay (Seed, B. and J. Y. Sheen (1988) A single phase-extraction assay for chloramphenicol acetyl transferase activity. *Gene* 76:271) 16 hr. after transfection. The results are presented in FIG. 5.

Example 10

Oligodeoxynucleotide Modifications Determine the Magnitude of B Cell Stimulation by CpG Motifs ODN were synthesized on an Applied Biosystems Inc. (Foster City, Calif.) model 380A, 380B, or 394 DNA synthesizer using standard procedures (Beacage and Caruthers (1981) Deoxynucleoside phosphoramidites—A new class of key intermediates for deoxypolynucleotide synthesis. Tetrahedon Letters 22, 1859-1862.). Phosphodiester ODN were synthesized using standard beta-cyanoethyl phosphoramidite chemistry. Phosphorothioate linkages were introduced by oxidizing the phosphite linkage with elemental sulfur instead of the standard iodine oxidation. The four common nucleoside phosphoramidites were purchased from Applied Biosystems. All phosphodiester and thioate containing ODN were protected by treatment with concentrated ammonia at 55° C. for 12 hours. The ODN were purified by gel exclusion chromatography and lyophilized to dryness prior to use. Phosphorodithioate linkages were introduced by using deoxynucleoside S-(b-benzoylmercaptoethyl)pyrrolidino thiophosphoramidites (Wiesler, W. T. et al.,(1993) In Methods in Molecular Biology: Protocols for Oligonucleotides and Analogs-Synthesis and Properties, Agrawal, S. (Ed.), Humana Press, 191-206.). Dithioate containing ODN were deprotected by treatment with concentrated ammonia at 55° C. for 12 hours followed by reverse phase HPLC purification.

In order to synthesize oligomers containing methylphosphonothioates or methylphosphonates as well as phosphodiesters at any desired internucleotide linkage, two different synthetic cycles were used. The major synthetic differences in two cycles are the coupling reagent where dialkylaminomethylnucleoside phosphines are used and the oxidation reagents in the case of methylphosphonothioates. In order to synthesize either derivative, the condensation time has been increased for the dialkylaminomethylnucleoside phosphines due to the slower kinetics of coupling (Jager and Engels, (1984) Synthesis of deoxynucleoside methylphosphonates via a phosphonamidite approach. Tetrahedron Letters 24, 1437-1440). After the coupling step has been completed, the methylphosphnodiester is treated with the sulfurizing reagent (5% elemental sulfur, 100 millimolar N,N-diamethylaminopyridine in carbon disulfide/pyridine/triethylamine), four consecutive times for 450 seconds each to produce methylphosphonothioates. To produce methylphosphonate linkages, the methylphosphinodiester is treated with standard oxidizing reagent (0.1 M iodine in tetrahydrofuran/2,6-lutidine/water).

The silica gel bound oligomer was treated with distilled pyridine/concentrated ammonia, 1:1, (v/v) for four days at 4 degrees centigrade. The supernatant was dried in vacuo, dissolved in water and chromatographed on a G50/50 Sephadex column.

As used herein, O-ODN refers to ODN which are phosphodiester; S-ODN are completely phosphorothioate modified; S-O=ODN are chimeric ODN in which the central linkages are phosphodiester, but the two 5' and five 3' linkages are phosphorothioate modified; $2_2$-O-ODN are chimeric ODN in which the central linkages are phosphodiester, but the two 5' and five 3' linkages are phosphorodithioate modified; and MP-O-ODN are chimeric ODN in which the central linkages are phosphodiester, but the two 5' and five 3' linkages are methylphosphonate modified. The ODN sequences studied (with CpG dinucleotides indicated by underlining) include:

3D (5" GAGAACGCTGGACCTTCCAT), (SEQ. ID. NO. 20);

3M (5' TCCATGTCGGTCCTGATGCT), (SEQ. ID. NO. 28);

5 (5' GGCGTTATTCCTGACTCGCC), (SEQ. ID. NO. 99); and 6 (5' CCTACGTTGTATGCGCCCAGCT), (SEQ. ID NO. 100).

These sequences are representative of literally hundreds of CpG and non-CpG ODN that have been tested in the course of these studies.

Mice. DBA/2, or BXSB mice obtained from The Jackson Laboratory (Bar Harbor, Me.), and maintained under specific pathogen-free conditions were used as a source of lymphocytes at 5-10 wk of age with essentially identical results.

Cell proliferation assay. For cell proliferation assays, mouse spleen cells ($5 \times 10^4$ cells/100 µl/well) were cultured at 37° C. in a 5% $CO_2$ humidified incubator in RPMI-1640 supplemented with 10% (v/v) heat inactivated fetal calf serum (heated to 65° C. for experiments with O-ODN, or 56° C. for experiments using only modified ODN), 1.5 µM L-glutamine, 50 µM 2-mercaptoethanol, 100 U/ml penicillin and 100 µg/ml streptomycin for 24 hr or 48 hr as indicated. 1 µCi of $^3$H uridine or thymidine (as indicated) was added to each well, and the cells harvested after an additional 4 hours of culture. Filters were counted by scintillation counting. Standard deviations of the triplicate wells were <5%. The results are presented in FIGS. 6-8.

Example 11

Induction of NK Activity

Phosphodiester ODN were purchased form Operon Technologies (Alameda, Calif.). Phosphorothioate ODN were purchased from the DNA core facility, University of Iowa, or from The Midland Certified Reagent Company (Midland Tex.). *E. coli* (strain B) DNA and calf thymus DNA were purchased from Sigma (St. Louis, Mo.). All DNA and ODN were purified by extraction with phenol:chloroform:isoamyl alcohol (25:24:1) and/or ethanol precipitation. The LPS level in ODN was less than 12.5 ng/mg and *E. coli* and calf thymus DNA contained less than 2.5 ng of LPS/mg of DNA by *Limulus* assay.

Virus-free, 4-6 week old, DBA/2, C57BL/6 (B6) and congenitally thymic BALB/C mice were obtained on contract through the Veterans Affairs from the National Cancer Institute (Bethesda, Md.). C57BL/6 SCID mice were bred in the SPF barrier facility at the University of Iowa Animal Care Unit.

Human peripheral monucluclear blood leukocytes (PBMC) were obtained as previously described (Ballas, Z. K. et al., (1990) *J. Allergy Clin. Immunol.* 85:453; Ballas, Z. K. And W. Rasmussen (1990). *J. Immunol.* 145:1039; Ballas, Z. K. and W. Rasmussen (1993) *J. Immunol.* 150; 17). Human or murine cells were cultured at $5 \times 10^6$/well, at 37° C. in a 5% $CO_2$ humidified atmosphere in 24-well plates (Ballas, Z. K. Et al., (1990) *J. Allergy Clin. Immunol.* 85:453; Ballas, Z. K. And W. Rasmussen (1990) *J. Immunol* 145:1039; and Ballas, Z. K. and W. Rasmussen (1193) *J. Immunol,* 150:17), with medium alone or with CpG or non-CpG ODN at the indicated concentrations, or with *E. coli* or calf thymus (50 µg/ml) at 37° C. for 24 hr. All cultures were harvested at 18 hr. and the cells were used as effectors in a standard 4 hr. $^{51}$Cr-release assay against K562 (human) or YAC-1 (mouse) target cells as previously described. For calculation of lytic units (LU), 1 LU was defined as the number of cells needed to effect 30% specific lysis. Where indicated, neutralizing antibodies against IFN-β (Lee Biomolecular, San Diego, Calif.) or IL-12 (C15.1, C15.6, C17.8, and C17.15; provided by Dr. Giorgio Trinchieri, The Winstar Institute, Philadelphia, Pa.) or their isotype controls were added at the initiation of cultures to a concentration of 10 µg/ml. For anti-IL-12 additional, 10 µg of each of the 4 MAB (or isotype controls) were added simultaneously. Recombinant human IL-2 was used at a concentration of 100 U/ml.

Example 12

Prevention of the Development of an Inflammatory Cellular

Infiltrate and Eosinophilia in a Murine Model of Asthma 6-8 week old C56BL/6 mice (from The Jackson Laboratory, Bar Harbor, Me.) were immunized with 5,000 *Schistosoma mansoni* eggs by intraperitoneal (i.p.) injection on days 0 and 7. *Schistosoma mansoni* eggs contain an antigen (*Schistosoma mansoni* egg antigen (SEA)) that induces a Th2 immune response (e.g. production of IgE antibody). IgE antibody production is known to be an important cause of asthma.

The immunized mice were then treated with oligonucleotides (30 µg in 200 µl saline by i.p. injection), which either contained an unmethylated CpG motif (i.e., TCCATGA CGTTCCTGACGTT; SEQ ID NO. 10) or did the (i.e., control, TCCATGAGCTTCCTGAGTCT; SEQ ID NO. 8). Soluble SeEA (10 µg in 25 µl of saline) was administered by intranasal instillation on days 14 and 21. Saline was used as a control.

Mice were sacrificed at various times after airway challenge. Whole lung lavage was performed to harvest airway and alveolar inflammatory cells. Cytokine levels were measured from lavage fluid by ELISA. RNA was isolated from whole lung for Northern analysis and RT-PCR studies using CsCl gradients. Lungs were inflated and perfused with 4% paraformaldehyde for histologic examination.

Figure 9:
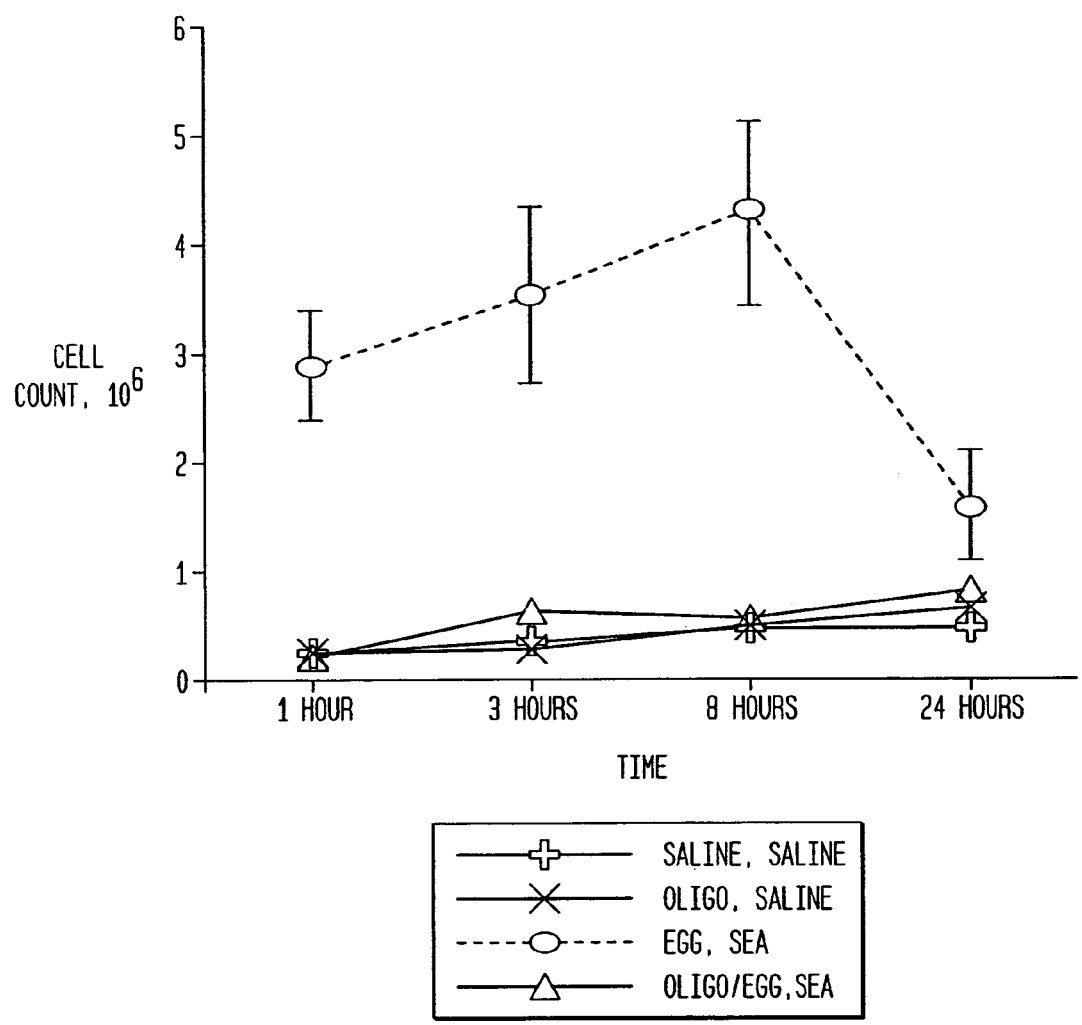

FIG. 9 shows that when the mice are initially injected with the eggs i.p., and then inhale the egg antigen (open circle), many inflammatory cells are present in the lungs. However, when the mice are initially given a nucleic acid containing an unmethylated CpG motif along with the eggs, the inflammatory cells in the lung are not increased by subsequent inhalation of the egg antigen (open triangles).

Figure 10:
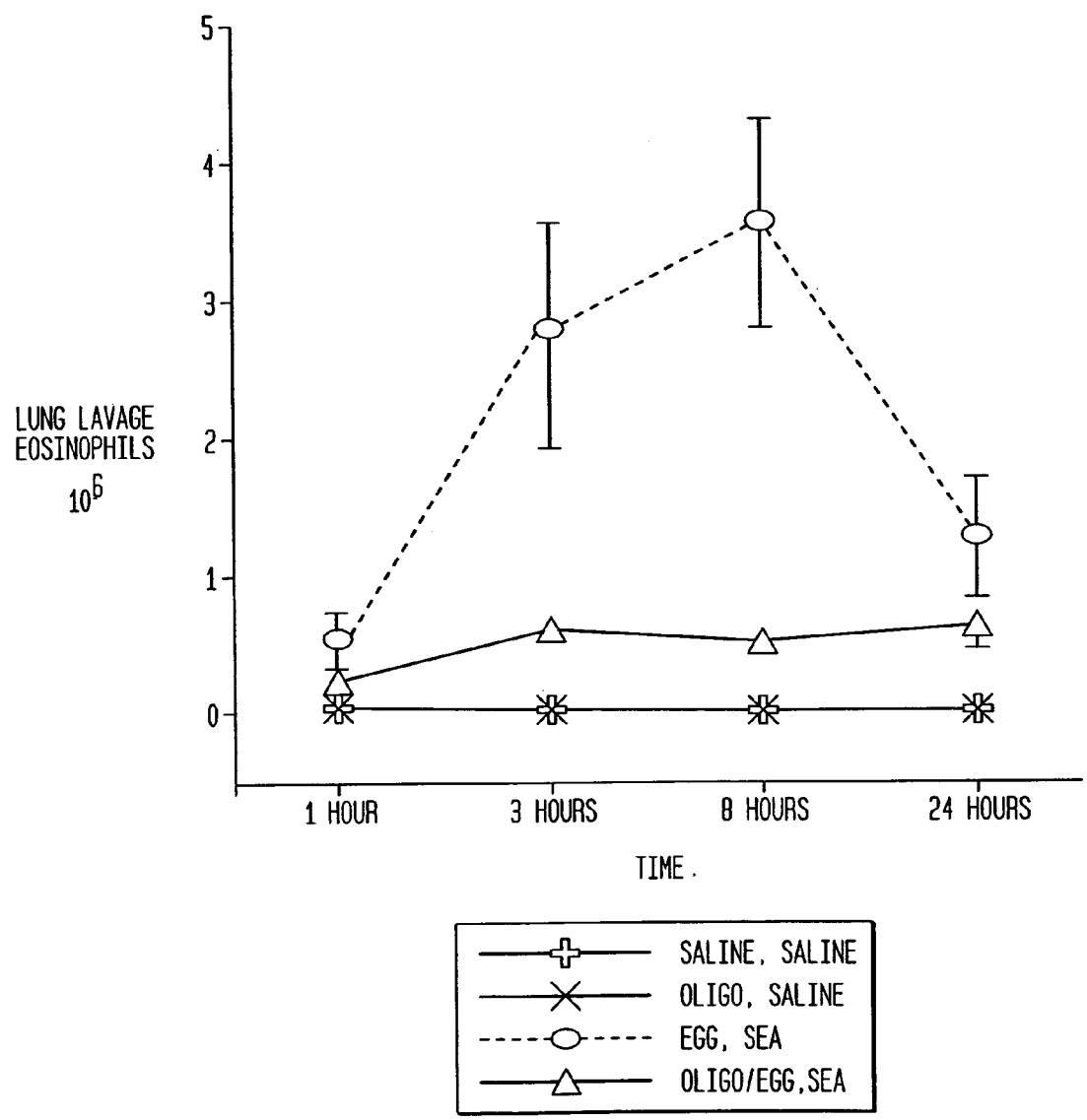

FIG. 10 shows that the same results are obtained only when eosinophils present in the lung lavage are measured. Eosinophils are the type of inflammatory cell most closely associated with asthma.

Figure 11:
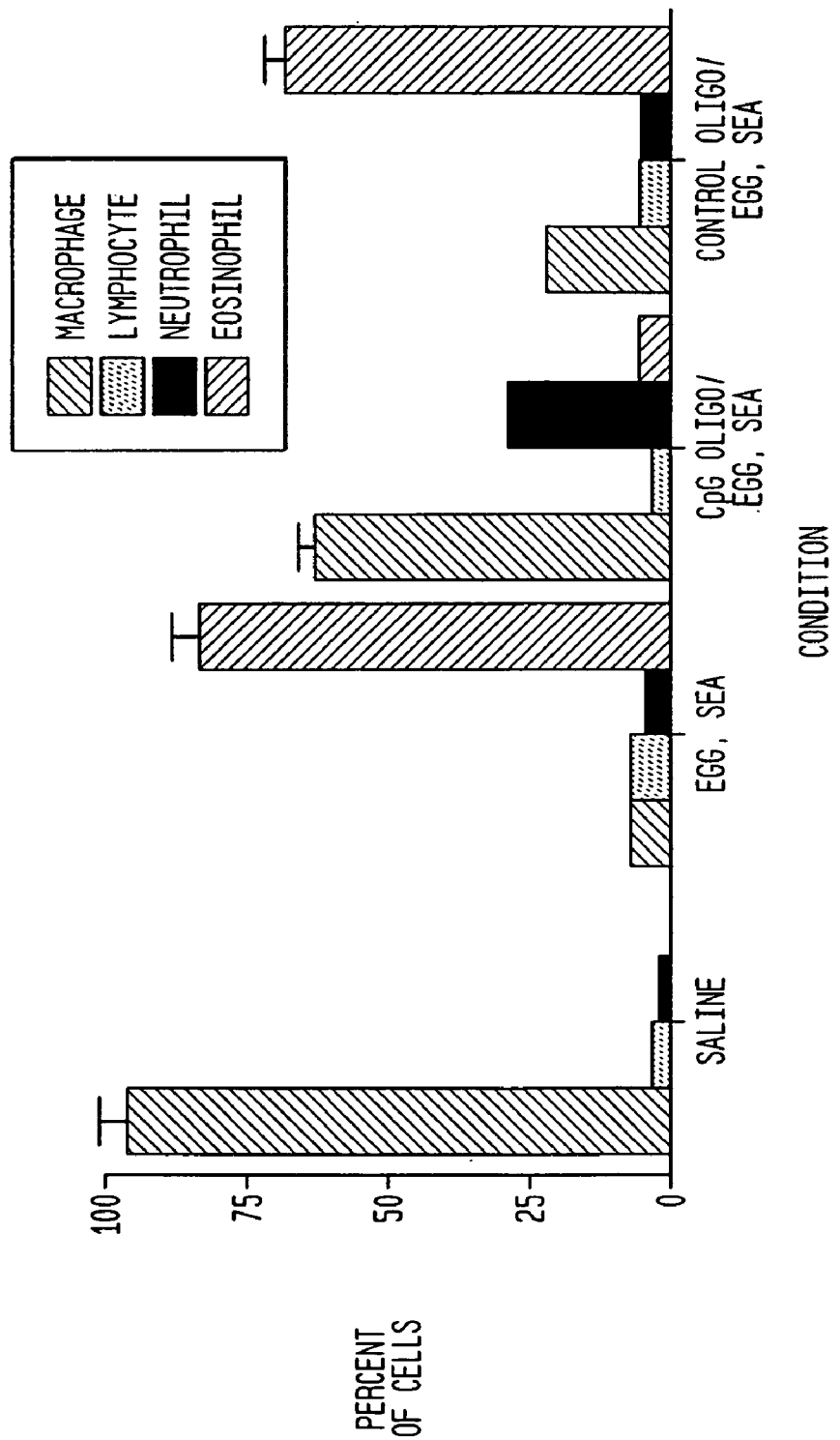

FIG. 11 shows that when the mice are treated with a control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

Figure 12:
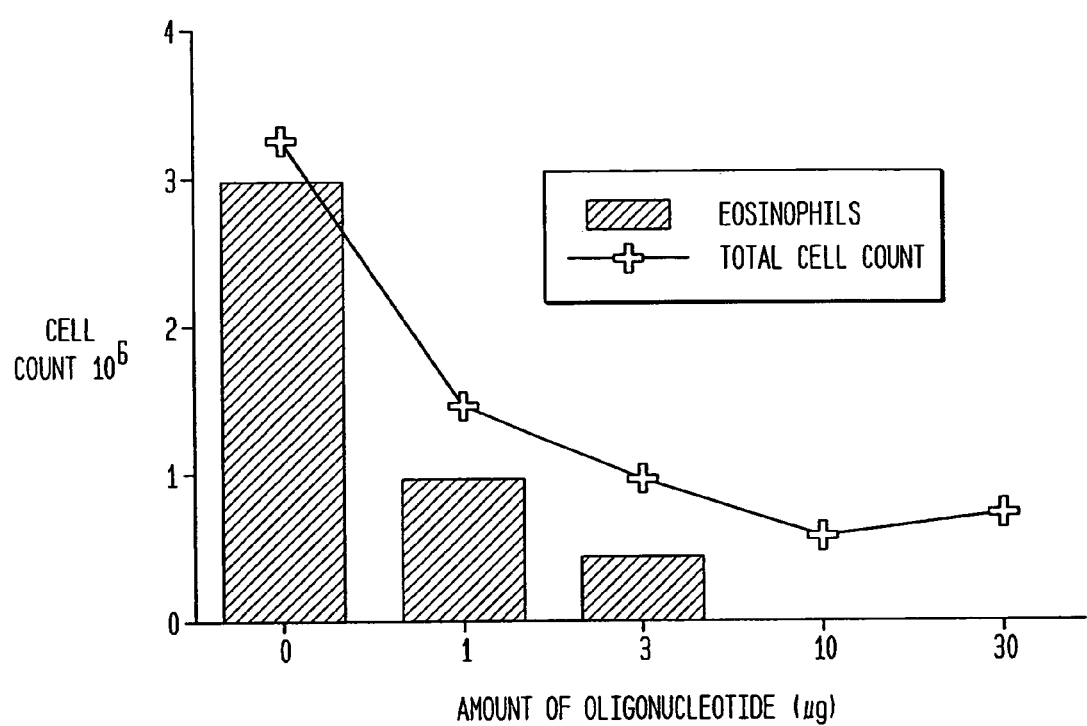
FIG. 12 is a bar graph plotting eosinophil count in response to injection of various amounts of the protective oligo SEQ ID NO: 10.

FIG. 12 shows that very low doses of oligonucleotide (<10 μg) can give this protection.

Figure 13:
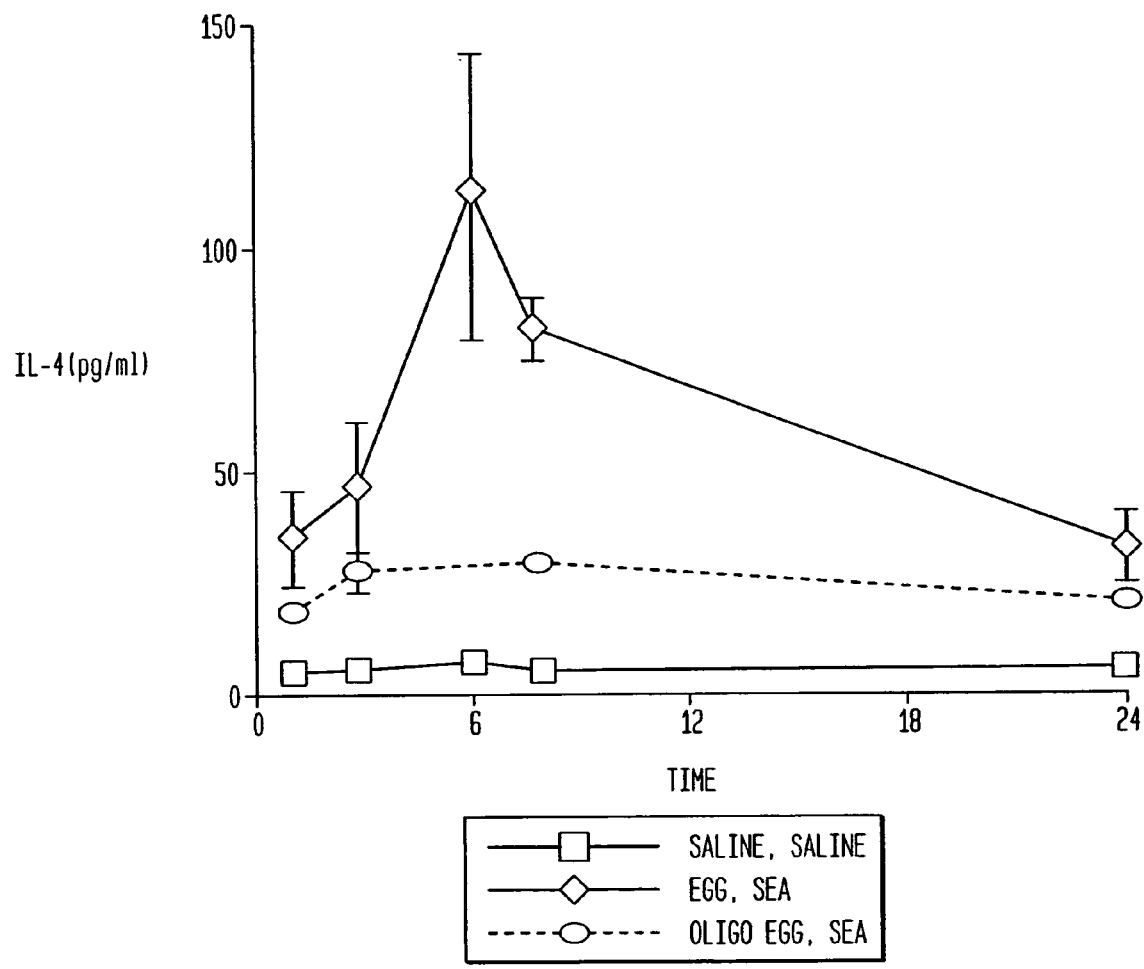
FIG. 13 is a graph plotting interleukin 4 (IL-4) production (pg/ml) in mice over time in response to injection of egg, then SEA (open diamond); egg and SEQ ID NO: 10, then SEA (open circle); or saline, then saline (open square). The graph shows that the resultant inflammatory response correlates with the levels of the Th2 cytokine IL-4 in the lung.

FIG. 13 shows that the resultant inflammatory response correlates with the levels of the Th2 cytokine IL-4 in the lung.

Figure 14:
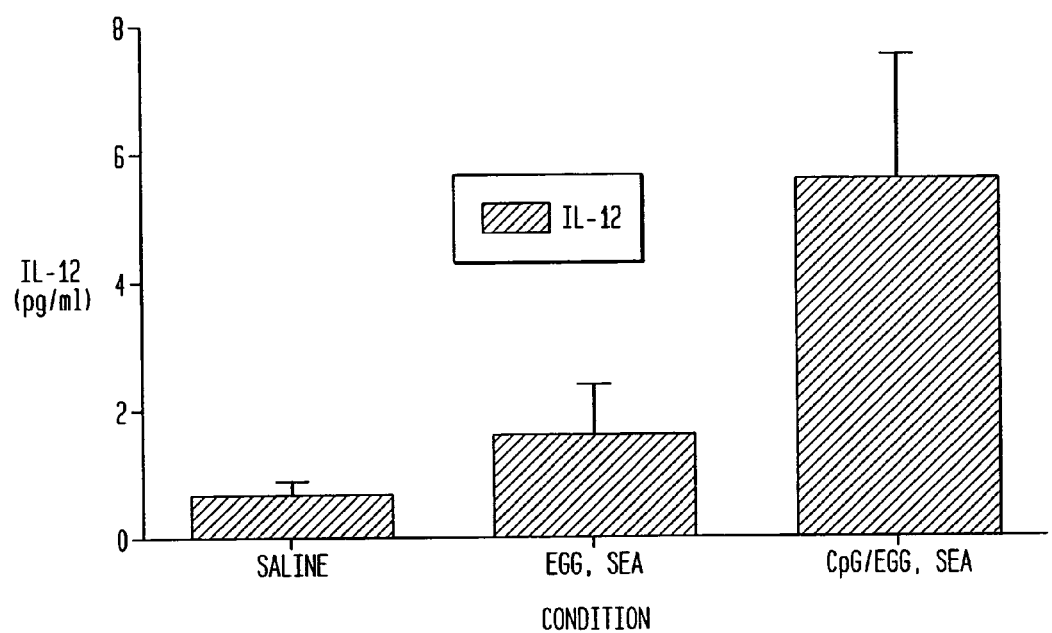
FIG. 14 is a bar graph plotting interleukin 12 (IL-12) production (pg/ml) in mice over time in response to injection of saline; egg, then SEA; or SEQ ID NO. 10 and egg, then SEA. The graph shows that administration of an oligonucleotide containing an unmethylated CpG motif can actually redirect the cytokine response of the lung to production of IL-12, indicating a Th1 type of immune response.

FIG. 14 shows that administration of an oligonucleotide containing an unmethylated CpG motif can actually redirect the cytokine response of the lung to production of Il-12, indicating the Th1 type of immune response.

Figure 15:
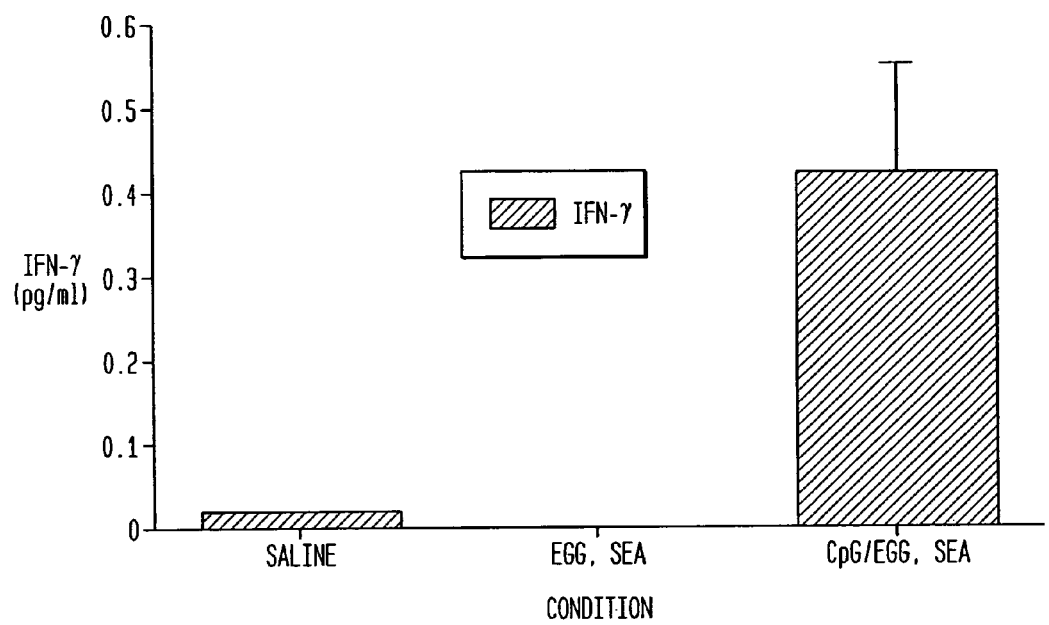
FIG. 15 is a bar graph plotting interferon gamma (IFN-γ) production (pg/ml) in mice over time in response to injection of saline; egg, then saline; or SEQ ID NO: 10 and egg, then SEA. The graph shows that administration of an oligonucleotide containing an unmethylated CpG motif can also redirect the cytokine response of the lung to production of IFN-g, indicating a Th1 type of immune response.

FIG. 15 shows that administration of an oligonucleotide containing an unmethylated CpG motif can also redirect the cytokine response of the lung to production of IFN-γ, indicating a Th1 type of immune response.

Example 13

CpG Oligonucleotides Induce Human PBMC to Secrete Cytokines

Human PBMC were prepared from whole blood by standard centrifugation over Ficoll hypaque. Cells ($5 \times 10^5$/ml) were cultured in 10% autologous serum in 95 well microtiter plates with CpG or control oligodeoxynucleotides (24 μg/ml for phosphodiester oligonucleotides; 6 g/ml for nuclease resistant phosphorothioate oligonucleotides) for 4 hr in the case of TNF-α or 24 hr. For the other cytokines before supernatant harvest and assay, measured by ELISA using Quantikine kits or reagents from R&D Systems (pg/ml) or cytokine ELISA kits from Biosource (for IL-12 assay). Assays were performed as per the manufacturer's instructions. Data are presented in Table 6 as the level of cytokine above that in wells with no added oligodeoxynucleotide.

Those skilled in the art will recognize, or be able to ascertain using no more than routine experimentation, many equivalents of the specific embodiments of the invention described herein. Such equivalents are intended to be encompassed by the following claims.

We claim:

1. A method for treating asthma in a subject, comprising administering to an asthmatic subject an effective amount for treating asthma in the subject of an immunostimulatory nucleic acid, having a sequence including at least the following formula:

$$5'X_1X_2CGX_3X_4 3'$$

wherein C is unmethylated, wherein $X_1X_2$ and $X_3X_4$ are nucleotides, wherein at least one internucleotide linkage has a phosphate backbone modification.

2. The method of claim 1, wherein the $5'X_1X_2CGX_3X_4 3'$ sequence is a non-palindromic sequence.

3. A method for treating asthma in a subject, comprising administering to an asthmatic subject an effective amount for treating asthma in the subject of an immunostimulatory nucleic acid, having a sequence including at least the following formula:

$$5'X_1X_2CGX_3X_4 3'$$

wherein C is unmethylated, wherein $X_1X_2$ and $X_3X_4$ are nucleotides, wherein the nucleic acid has a length of 8 to 100 nucleotides.

4. The method of claim 1, wherein the phosphate backbone modification is a phosphorothioate modification.

5. The method of claim 1, wherein the nucleic acid backbone includes the phosphate backbone modification on the 3' side of the nucleic acid.

6. The method of claim 1, wherein the phosphate backbone modification is a phosphorodithioate modification.

7. The method of claim 1, wherein $X_1X_2$ are GpA and $X_3X_4$ are TpT.

8. The method of claim 1, wherein $X_1$ and $X_2$ are purines and $X_3$ and $X_4$ are pyrimidines.

9. The method of claim 1, wherein $X_1X_2$ are GpA and $X_3$ and $X_4$ are pyrimidines.

10. The method of claim 1, wherein the immunostimulatory nucleic acid is 8 to 40 nucleotides in length.

11. The method of claim 1, wherein the immunostimulatory nucleic acid is an isolated immunostimulatory nucleic acid.

12. The method of claim 1, wherein the immunostimulatory nucleic acid comprises the following nucleotide sequence TCCATGACGTTCCTGACGTT (SEQ ID NO. 10).

13. The method of claim 1, wherein the immunostimulatory nucleic acid comprises a nucleotide sequence selected from the group of the following nucleotide sequences TCCATAACGTTCCTGATGCT (SEQ ID NO:3), TCCATGTCGTTCCTGATGCT (SEQ ID NO:38), and TCCATGACGTTCCTGATGCT (SEQ ID NO:7).

14. A method for treating asthma in a subject, comprising administering to an asthmatic subject an effective amount for treating asthma in a subject of an immunostimulatory nucleic acid, wherein the immunostimulatory nucleic acid is 8-40 nucleotides in length, includes a 5'TC and comprises a nucleotide sequence GTCGTT (SEQ. ID. NO: 57) wherein C is unmethylated.

15. The method of claim 14, wherein the nucleic acid has a phosphodiester backbone.

16. The method of claim 14, wherein the nucleic acid has a chimeric phosphodiester-phosphorothioate backbone.

17. The method of claim 14, wherein the immunostimulatory nucleic acid comprises the following nucleotide sequence GGGGTCAACGTTGAGGGGGG (SEQ ID NO:12).

18. A method for treating asthma in a subject, comprising administering to an asthmatic subject an effective amount for treating asthma in the subject of a nucleic acid, having a sequence including at least the following formula:

$$5'X_1X_2CGX_3X_43'$$

wherein C is unmethylated, wherein $X_1X_2$ and $X_3X_4$ are nucleotides, wherein at least one internucleotide linkage has a phosphate backbone modification and wherein the nucleic acid has a length of 8 to 40 nucleotides.

19. A method for treating asthma in a subject, comprising orally administering to an asthmatic subject an effective amount for treating asthma in the subject of a nucleic acid having a sequence including at least the following formula:

$$5'X_1X_2CGX_3X_43'$$

wherein C is unmethylated, and wherein $X_1X_2$ and $X_3X_4$ are nucleotides, wherein at least one internucleotide linkage has a phosphate backbone modification.

20. A method for treating asthma in a subject, comprising administering to an asthmatic subject an effective amount for treating asthma in the subject of a nucleic acid having a sequence including at least the following formula:

$$5'X_1X_2CGX_3X_43'$$

wherein C is unmethylated, wherein $X_1X_2$ and $X_3X_4$ are nucleotides wherein at least one internucleotide linkage has a phosphate backbone modification, and wherein the nucleic acid is administered by a route selected from the group consisting of transdermal and subcutaneous.

21. A method for treating asthma in a subject, comprising administering to an asthmatic subject an effective amount for treating asthma in the subject of a nucleic acid having a sequence including at least the following formula:

$$5'X_1X_2CGX_3X_43'$$

wherein C is unmethylated, wherein $X_1X_2$ and $X_3X_4$ are nucleotides, wherein the nucleic acid has a length of 8 to 100 nucleotides, and wherein the nucleic acid is administered in a formulation selected from the group consisting of a nucleic acid delivery complex, a liposome, a virosome, and a nanoparticle.

22. The method of claim 1, wherein the nucleic acid is administered by a route selected from the group consisting of oral, transdermal, and subcutaneous.

23. The method of claim 1, wherein the nucleic acid is delivered in a formulation selected from the group consisting of a nucleic acid delivery complex, a liposome, a virosome, and a nanoparticle.

24. The method of claim 3, wherein at least one internucleotide linkage of the nucleic acid has a phosphate backbone modification.

25. The method of claim 3, wherein the phosphate backbone modification is a phosphorothioate modification.

* * * * *

UNITED STATES PATENT AND TRADEMARK OFFICE
CERTIFICATE OF CORRECTION

PATENT NO. : 7,935,675 B1
APPLICATION NO. : 09/337584
DATED : May 3, 2011
INVENTOR(S) : Arthur M. Krieg et al.

It is certified that error appears in the above-identified patent and that said Letters Patent is hereby corrected as shown below:

Please amend the Government Support section in col. 1, line 19 to read:

This invention was made with government support under grant number R29-AR42556-01 awarded by National Institutes of Health. The government has certain rights in the invention.

Signed and Sealed this
Fourteenth Day of June, 2011

David J. Kappos
*Director of the United States Patent and Trademark Office*

```
                        SEQUENCE LISTING

<160> NUMBER OF SEQ ID NOS: 123

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
atggaaggtc cagcgttctc                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
atcgacctac gtgcgttctc                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
tccataacgt tcctgatgct                                                     20

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 4
gctagatgtt agcgt                                                          15
```

```
<210> SEQ ID NO 5
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 5
gagaacgtcg accttcgat                                               19

<210> SEQ ID NO 6
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 6
gcatgacgtt gagct                                                   15

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
tccatgacgt tcctgatgct                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
tccatgagct tcctgagtct                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tccaagacgt tcctgatgct                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
tccatgacgt tcctgacgtt                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide
```

```
<400> SEQUENCE: 11
tccatgagct tcctgagtgc t                                              21

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ggggtcaacg ttgagggggg                                                20

<210> SEQ ID NO 13
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)...(7)
<223> OTHER INFORMATION: m5c

<400> SEQUENCE: 13
gctagangtt agcgt                                                     15

<210> SEQ ID NO 14
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (13)...(13)
<223> OTHER INFORMATION: m5c

<400> SEQUENCE: 14
gctagacgtt agngt                                                     15

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
atcgactctc gagcgttctc                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c
```

```
<400> SEQUENCE: 16
atngactctn gagngttctc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (3)...(3)
<223> OTHER INFORMATION: m5c

<400> SEQUENCE: 17
atngactctc gagcgttctc                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (18)...(18)
<223> OTHER INFORMATION: m5c

<400> SEQUENCE: 18
atcgactctc gagcgttntc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
atggaaggtc caacgttctc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gagaacgctg gaccttccat                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gagaacgctc gaccttccat                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 22
gagaacgctc gaccttcgat                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
gagcaagctg gaccttccat                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (6)...(6)
<223> OTHER INFORMATION: m5c

<400> SEQUENCE: 24
gagaangctg gaccttccat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (14)...(14)
<223> OTHER INFORMATION: m5c

<400> SEQUENCE: 25
gagaacgctg gacnttccat                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gagaacgatg gaccttccat                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
gagaacgctc cagcactgat                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 28
tccatgtcgg tcctgatgct                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
tccatgctgg tcctgatgct                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 30
tccatgtngg tcctgatgct                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (12)...(12)
<223> OTHER INFORMATION: m5c

<400> SEQUENCE: 31
tccatgtcgg tnctgatgct                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
tccatgtcgg tcctgctgat                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tccatgccgg tcctgatgct                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 34
tccatggcgg tcctgatgct                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
tccatgacgg tcctgatgct                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tccatgtcga tcctgatgct                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tccatgtcgc tcctgatgct                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tccatgtcgt tcctgatgct                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tccatgacgt ccctgatgct                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tccatcacgt gcctgatgct                                          20

<210> SEQ ID NO 41
<211> LENGTH: 19
```

```
<212> TYPE: DNA
<213> ORGANISM: Artificial Sequence
<220> FEATURE:
<223> OTHER INFORMATION: Synthetic Oligonucleotide

<400> SEQUENCE: 41
ggggtcagtc ttgacgggg                                                19

<210> SEQ ID NO 42
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 42
gctagacgtt agtgt                                                    15

<210> SEQ ID NO 43
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 43
gctagacntt agtgt                                                    15

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c

<400> SEQUENCE: 44
tccatgtngt tcctgatgct                                               20

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
tctcccagcg tgcgccat                                                 18

<210> SEQ ID NO 46
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
tcgtcgtttt gtcgttttgt cgtt                                          24

<210> SEQ ID NO 47
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 47
tcgtcgttgt cgttgtcgtt                                             20

<210> SEQ ID NO 48
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 48
tgtcgtttgt cgtttgtcgt t                                           21

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
tcgtcgttgt cgttttgtcg tt                                          22

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 50
tgtcgttgtc gttgtcgtt                                              19

<210> SEQ ID NO 51
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 51
tcgtcgtcgt cgtt                                                   14

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
tcctgtcgtt ccttgtcgtt                                             20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
tcctgtcgtt ttttgtcgtt                                             20
```

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
tcgtcgctgt ctgcccttct t                                    21

<210> SEQ ID NO 55
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 55
tcgtcgctgt tgtcgtttct t                                    21

<210> SEQ ID NO 56
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 56
gcgtgcgttg tcgttgtcgt t                                    21

<210> SEQ ID NO 57
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 57 gtcgtt                                                      6

<210> SEQ ID NO 58
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 58 gtcgct                                                      6

<210> SEQ ID NO 59
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 59
accatggacg atctgtttcc cctc                                 24

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 60
taccgcgtgc gaccctct                                          18

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 61
accatggacg aactgtttcc cctc                                   24

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 62
accatggacg agctgtttcc cctc                                   24

<210> SEQ ID NO 63
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 63
accatggacg acctgtttcc cctc                                   24

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 64
accatggacg tactgtttcc cctc                                   24

<210> SEQ ID NO 65
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 65
accatggacg gtctgtttcc cctc                                   24

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 66
accatggacg ttctgtttcc cctc                                   24

<210> SEQ ID NO 67
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 67
cacgttgagg ggcat                                                    15

<210> SEQ ID NO 68
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 68
ctgctgagac tggag                                                    15

<210> SEQ ID NO 69
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 69
tcagcgtgcg cc                                                       12

<210> SEQ ID NO 70
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 70
atgacgttcc tgacgtt                                                  17

<210> SEQ ID NO 71
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 71
tctcccagcg ggcgcat                                                  17

<210> SEQ ID NO 72
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 72
tctcccagcg cgcgccat                                                 18

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tccatgtcgt tcctgtcgtt                                               20
```

```
<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
tccatagcgt tcctagcgtt                                               20

<210> SEQ ID NO 75
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 75
tcgtcgctgt ctccgcttct t                                             21

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 76
tcctgacgtt cctgacgtt                                                19

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
tcctgtcgtt cctgtcgtt                                                19

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
tccatgtcgt ttttgtcgtt                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
tccaggactt ctctcaggtt                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 80
tccatgcgtg cgtgcgtttt                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
tccatgcgtt gcgttgcgtt                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
tccacgacgt tttcgacgtt                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gcggcgggcg gcgcgcgccc                                              20

<210> SEQ ID NO 84
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 84
tgtcgttgtc gttgtcgttg tcgtt                                        25

<210> SEQ ID NO 85
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 85
tgtcgttgtc gtt                                                     13

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
tccacgacgt tttcgacgtt                                              20

<210> SEQ ID NO 87
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 87
tccatgacga tcctgatgct                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
tccatgacgc tcctgatgct                                               20

<210> SEQ ID NO 89
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 89
gctagacgtt agcgt                                                    15

<210> SEQ ID NO 90
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 90 tcaacgtt                                                             8

<210> SEQ ID NO 91
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 91 tcaagctt                                                             8

<210> SEQ ID NO 92
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 92 tcagcgct                                                             8

<210> SEQ ID NO 93
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 93 tcatcgat                                                             8
```

<210> SEQ ID NO 94
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 94 tcttcgaa                                                               8

<210> SEQ ID NO 95
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 95 ccaacgtt                                                               8

<210> SEQ ID NO 96
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 96 tcaacgtc                                                               8

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
tccaggactt tcctcaggtt                                                 20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
ttcaggactt tcctcaggtt                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
ggcgttattc ctgactcgcc                                                 20

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligonucleotide

```
<400> SEQUENCE: 100
cctacgttgt atgcgcccag ct                                          22

<210> SEQ ID NO 101
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 101 tgtcgct                                                            7

<210> SEQ ID NO 102
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 102 tgtcgtt                                                            7

<210> SEQ ID NO 103
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 103 tgacgtc                                                            7

<210> SEQ ID NO 104
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 104 tgacgtca                                                           8

<210> SEQ ID NO 105
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 105 aacgtt                                                             6

<210> SEQ ID NO 106
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 106 caacgtt                                                            7

<210> SEQ ID NO 107
<211> LENGTH: 8
```

```
<212> TYPE: DNA
<213> ORGANISM: Artificial Sequence
<220> FEATURE:
<223> OTHER INFORMATION: Synthetic Oligonucleotide

<400> SEQUENCE: 107 aacgttct                                                                8

<210> SEQ ID NO 108
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 108 tgacgtt                                                                 7

<210> SEQ ID NO 109
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 109 gccggt                                                                  6

<210> SEQ ID NO 110
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 110 gacggt                                                                  6

<210> SEQ ID NO 111
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 111 gacgtc                                                                  6

<210> SEQ ID NO 112
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 112 cacgtg                                                                  6

<210> SEQ ID NO 113
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 113 cgacgtt                                                                 7
```

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
atggaaggtc cagtgttctc                                                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
atggactctc cagcgttctc                                                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (14)...(14)
<223> OTHER INFORMATION: m5c

<400> SEQUENCE: 116
atcgactctc gagngttctc                                                    20

<210> SEQ ID NO 117
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)...(7)
<223> OTHER INFORMATION: m5c

<400> SEQUENCE: 117
gctagangtt agtgt                                                         15

<210> SEQ ID NO 118
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 118
catttccacg atttccca                                                      18

<210> SEQ ID NO 119
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 119
tcgtcgctgt ctgcccttct t                                                  21

```
<210> SEQ ID NO 120
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 120
tcgtcgctgt tgtcgtttct t                                              21

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
tccttgtcgt tcctgtcgtt                                                20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (8)...(8)
<223> OTHER INFORMATION: m5c
<220> FEATURE:
<221> NAME/KEY: modified_base
<222> LOCATION: (17)...(17)
<223> OTHER INFORMATION: m5c

<400> SEQUENCE: 122
tccatgtngt tcctgtngtt                                                20

<210> SEQ ID NO 123
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 123
tcgtcgtttt gtcgttttgt cgt                                            23
```